United States Patent
Elbaz et al.

(10) Patent No.: US 12,127,814 B2
(45) Date of Patent: Oct. 29, 2024

(54) DENTAL DIAGNOSTICS HUB

(71) Applicant: Align Technology, Inc., San Jose, CA (US)

(72) Inventors: Gilad Elbaz, Tel Aviv (IL); Michael Sabina, Campbell, CA (US); Ran Katz, Hod Hasharon (IL); Avi Kopelman, Palo Alto, CA (US); Eric Kuo, San Jose, CA (US); Leon Rasovsky, Mountain View, CA (US)

(73) Assignee: Align Technology, Inc., San Jose, CA (US)

( * ) Notice: Subject to any disclaimer, the term of this patent is extended or adjusted under 35 U.S.C. 154(b) by 359 days.

(21) Appl. No.: 17/564,115

(22) Filed: Dec. 28, 2021

(65) Prior Publication Data

US 2022/0202295 A1   Jun. 30, 2022

Related U.S. Application Data

(60) Provisional application No. 63/132,406, filed on Dec. 30, 2020.

(51) Int. Cl.
*A61B 5/00* (2006.01)
*A61B 6/51* (2024.01)
*A61C 9/00* (2006.01)
*G16H 20/00* (2018.01)
*G16H 50/20* (2018.01)

(52) U.S. Cl.
CPC .......... *A61B 5/0088* (2013.01); *A61B 5/0062* (2013.01); *A61B 5/4547* (2013.01); *A61B 5/4552* (2013.01); *A61B 5/4842* (2013.01); *A61B 5/7267* (2013.01); *A61B 5/742* (2013.01); *A61B 5/7475* (2013.01); *A61B 6/512* (2024.01); *A61C 9/0053* (2013.01); *G16H 20/00* (2018.01); *G16H 50/20* (2018.01)

(58) Field of Classification Search
CPC ..... A61B 5/0088; A61B 6/512; A61B 5/0062; A61B 5/4547; A61B 5/4552; A61B 5/4842; A61B 5/7267; A61B 5/742; A61B 5/7475; A61C 9/0053; G16H 20/00; G16H 50/20
USPC ........................................................ 382/128
See application file for complete search history.

(56) References Cited

U.S. PATENT DOCUMENTS

| | | | |
|---|---|---|---|
| 6,099,314 | A | 8/2000 | Kopelman et al. |
| 6,334,772 | B1 | 1/2002 | Taub et al. |
| 6,334,853 | B1 | 1/2002 | Kopelman et al. |
| 6,463,344 | B1 | 10/2002 | Pavlovskaia et al. |
| 6,542,249 | B1 | 4/2003 | Kofman et al. |
| 6,633,789 | B1 | 10/2003 | Nikolskiy et al. |

(Continued)

FOREIGN PATENT DOCUMENTS

CN    106470595 A    3/2017

*Primary Examiner* — Michael R Neff
(74) *Attorney, Agent, or Firm* — Lowenstein Sandler LLP

(57) ABSTRACT

A method includes receiving intraoral scan data of an intraoral cavity of a patient; processing the intraoral scan data to determine, for each dental condition of a plurality of dental conditions, whether the dental condition is detected for the patient and a severity of the dental condition; and presenting indications of the plurality of dental conditions together in a graphical user interface (GUI), wherein the indications show, for each dental condition of the plurality of dental conditions, whether the dental condition was detected for the patient and the severity of the dental condition.

27 Claims, 20 Drawing Sheets

(56) References Cited

U.S. PATENT DOCUMENTS

| | | |
|---|---|---|
| 6,664,986 B1 | 12/2003 | Kopelman et al. |
| 6,697,164 B1 | 2/2004 | Babayoff et al. |
| 6,845,175 B2 | 1/2005 | Kopelman et al. |
| 6,979,196 B2 | 12/2005 | Nikolskiy et al. |
| 7,030,383 B2 | 4/2006 | Babayoff et al. |
| 7,202,466 B2 | 4/2007 | Babayoff et al. |
| 7,255,558 B2 | 8/2007 | Babayoff et al. |
| 7,286,954 B2 | 10/2007 | Kopelman et al. |
| 7,319,529 B2 | 1/2008 | Babayoff |
| 7,373,286 B2 | 5/2008 | Nikolskiy et al. |
| 7,507,088 B2 | 3/2009 | Taub et al. |
| 7,545,372 B2 | 6/2009 | Kopelman et al. |
| 7,698,068 B2 | 4/2010 | Babayoff |
| 7,916,911 B2 | 3/2011 | Kaza et al. |
| 8,108,189 B2 | 1/2012 | Chelnokov et al. |
| 8,244,028 B2 | 8/2012 | Kuo et al. |
| 8,587,582 B2 | 11/2013 | Matov et al. |
| 8,948,482 B2 | 2/2015 | Levin |
| D742,518 S | 11/2015 | Barak et al. |
| 9,192,305 B2 | 11/2015 | Levin |
| 9,261,356 B2 | 2/2016 | Lampert et al. |
| 9,261,358 B2 | 2/2016 | Atiya et al. |
| 9,299,192 B2 | 3/2016 | Kopelman |
| D760,901 S | 7/2016 | Barak et al. |
| 9,393,087 B2 | 7/2016 | Moalem |
| 9,408,679 B2 | 8/2016 | Kopelman |
| 9,431,887 B2 | 8/2016 | Boltanski |
| 9,439,568 B2 | 9/2016 | Atiya et al. |
| 9,451,873 B1 | 9/2016 | Kopelman et al. |
| D768,861 S | 10/2016 | Barak et al. |
| D771,817 S | 11/2016 | Barak et al. |
| 9,491,863 B2 | 11/2016 | Boltanski |
| D774,193 S | 12/2016 | Makmel et al. |
| 9,510,757 B2 | 12/2016 | Kopelman et al. |
| 9,626,462 B2 | 4/2017 | Somasundaram et al. |
| 9,660,418 B2 | 5/2017 | Atiya et al. |
| 9,668,829 B2 | 6/2017 | Kopelman |
| 9,675,430 B2 | 6/2017 | Verker et al. |
| 9,693,839 B2 | 7/2017 | Atiya et al. |
| 9,717,402 B2 | 8/2017 | Lampert et al. |
| 9,724,177 B2 | 8/2017 | Levin |
| 9,844,426 B2 | 12/2017 | Atiya et al. |
| 10,076,389 B2 | 9/2018 | Wu et al. |
| 10,098,714 B2 | 10/2018 | Kuo |
| 10,108,269 B2 | 10/2018 | Sabina et al. |
| 10,111,581 B2 | 10/2018 | Makmel |
| 10,111,714 B2 | 10/2018 | Kopelman et al. |
| 10,123,706 B2 | 11/2018 | Elbaz et al. |
| 10,136,972 B2 | 11/2018 | Sabina et al. |
| 10,380,212 B2 | 8/2019 | Elbaz et al. |
| 10,390,913 B2 | 8/2019 | Sabina et al. |
| 10,453,269 B2 | 10/2019 | Furst |
| 10,456,043 B2 | 10/2019 | Atiya et al. |
| 10,499,793 B2 | 12/2019 | Ozerov et al. |
| 10,504,386 B2 | 12/2019 | Levin et al. |
| 10,507,087 B2 | 12/2019 | Elbaz et al. |
| 10,517,482 B2 | 12/2019 | Sato et al. |
| 10,695,150 B2 | 6/2020 | Kopelman et al. |
| 10,708,574 B2 | 7/2020 | Furst et al. |
| 10,772,506 B2 | 9/2020 | Atiya et al. |
| 10,813,727 B2 | 10/2020 | Sabina et al. |
| 10,888,399 B2 | 1/2021 | Kopelman et al. |
| 10,952,816 B2 | 3/2021 | Kopelman |
| 10,980,613 B2 | 4/2021 | Shanjani et al. |
| 11,013,581 B2 | 5/2021 | Sabina et al. |
| D925,739 S | 7/2021 | Shalev et al. |
| 11,096,765 B2 | 8/2021 | Atiya et al. |
| 11,238,586 B2 | 2/2022 | Minchenkov et al. |
| 2016/0135925 A1* | 5/2016 | Mason .................. A61C 7/002 703/2 |
| 2018/0028065 A1* | 2/2018 | Elbaz .................. A61B 5/7435 |
| 2018/0168781 A1* | 6/2018 | Kopelman ............. A61B 34/10 |
| 2019/0029784 A1 | 1/2019 | Moalem et al. |
| 2019/0388193 A1 | 12/2019 | Saphier et al. |
| 2020/0146646 A1* | 5/2020 | Tuzoff ...................... G06T 7/11 |
| 2020/0281700 A1 | 9/2020 | Kopelman et al. |
| 2020/0281702 A1 | 9/2020 | Kopelman et al. |
| 2020/0315434 A1 | 10/2020 | Kopelman et al. |
| 2020/0349705 A1 | 11/2020 | Minchenkov et al. |
| 2020/0404243 A1 | 12/2020 | Saphier et al. |
| 2021/0030503 A1 | 2/2021 | Shalev et al. |
| 2021/0059796 A1 | 3/2021 | Weiss et al. |
| 2021/0068773 A1 | 3/2021 | Moshe et al. |
| 2021/0121049 A1 | 4/2021 | Rudnitsky et al. |
| 2021/0128281 A1 | 5/2021 | Peleg |
| 2021/0137653 A1 | 5/2021 | Saphier et al. |
| 2021/0196152 A1 | 7/2021 | Saphier et al. |
| 2021/0377374 A1* | 12/2021 | Peterson ................. A61B 1/24 |

* cited by examiner

DENTAL DIAGNOSTICS HUB

RELATED APPLICATIONS

This application claims the benefit of Provisional Application No. 63/132,406, filed Dec. 30, 2020, the entire content of which is incorporated by reference herein.

TECHNICAL FIELD

Embodiments of the present disclosure relate to the field of dental diagnostics and, in particular, to a system and method for improving the process of diagnosing dental conditions.

BACKGROUND

For a typical dental practice, a patient visits the dentist twice a year for a cleaning and an examination. A dental office may or may not generate a set of x-ray images of the patient's teeth during the patient visit. The dental hygienist additionally cleans the patient's teeth and notes any possible problem areas, which they convey to the dentist. The dentist then reviews the patient history, reviews the new x-rays (if any such x-rays were generated), and spends a few minutes examining the patient's teeth in a patient examination process. During the patient examination process, the dentist may follow a checklist of different areas to review. The examination can start with examining the patient's teeth for cavities, then reviewing existing restorations, then checking the patient's gums, then checking the patients' head, neck and mouth for pathologies or tumors, then checking the jaw joint, then checking the bite relationship and/or other orthodontic problems, and then checking any x-rays of the patient. Based on this review, the dentist makes a determination as to whether there are any dental conditions that need to be dealt with immediately and whether there are any other dental conditions that are not urgent but that should be dealt with eventually and/or that should be monitored. The dentist then needs to explain the identified dental conditions to the patient, talk to the patient about potential treatments, and convince the patient to make a decision on treatment for the patient's health. It can be challenging for the dentist to identify all problem dental conditions and convey the information about the dental conditions and their treatments to the patient in the short amount of time that the dentist has allotted for that patient. The challenge is exacerbated by the fact that information about the patient's teeth can be fragmented and siloed, requiring the dentist to open and review multiple different applications and data sources to gain a full understanding of the patient's dental health and gum health. Sometimes the necessary information may exist at another provider's office including previous dentists and/or other dental specialists. This can lead to misdiagnosis of dental conditions and also increase the amount of time that the dentist must spend with each patient.

SUMMARY

A few example implementations of the present disclosure are described.

In a first implementation, a method comprises: receiving intraoral scan data of an intraoral cavity of a patient; processing the intraoral scan data to determine, for each dental condition of a plurality of dental conditions, whether the dental condition is detected for the patient and a severity of the dental condition; and presenting indications of the plurality of dental conditions together in a graphical user interface (GUI), wherein the indications show, for each dental condition of the plurality of dental conditions, whether the dental condition was detected for the patient and the severity of the dental condition. The boundaries of the severity may be user-defined or pre-set based on industry norms.

A second implementation may further extend the first implementation. In the second implementation, processing the intraoral scan data comprises processing the intraoral scan data using a plurality of algorithms, wherein each algorithm of the plurality of algorithms is associated with a different type of dental condition.

A third implementation may further extend the first or second implementation. In the third implementation, one or more of the plurality of algorithms comprises a trained machine learning model that has been trained to receive the intraoral scan data as an input and to generate an output indicating at least one of a probability that the patient has a particular dental condition or a location of an area of interest in the intraoral cavity of the patient at which the particular dental condition was detected.

A fourth implementation may further extend the first through third implementations. In the fourth implementation, the plurality of dental conditions comprises one or more dental conditions selected from the list consisting of caries, gum recession, tooth wear, malocclusion, tooth crowding, tooth spacing, plaque, tooth stains, and tooth cracks.

A fifth implementation may further extend the first through fourth implementations. In the fifth implementation, the method further comprises: generating a three-dimensional (3D) model of one or more dental arch of the patient based on the intraoral scan data; and presenting the 3D model of the one or more dental arch of the patient together with the indications of the plurality of dental conditions in the GUI.

A sixth implementation may further extend the first through fifth implementations. In the sixth implementation, the method further comprises: generating a three-dimensional (3D) model of one or more dental arch of the patient based on the intraoral scan data; receiving a selection of a dental condition from the plurality of dental conditions; determining locations of one or more areas of interest on the one or more dental arch at which the dental condition was detected; and displaying the 3D model of the dental arch, wherein the one or more areas of interest are shown on the 3D model of the one or more dental arch at the determined locations of the one or more areas of interest.

A seventh implementation may further extend the first through sixth implementations. In the seventh implementation, the intraoral scan data comprises three-dimensional scan data, two-dimensional near infrared scan data and two-dimensional color scan data, and wherein at least two of the three-dimensional scan data, the two-dimensional near infrared scan data and the two-dimensional color scan data are processed together to determine one or more of the plurality of dental conditions.

An eighth implementation may further extend the first through seventh implementations. In the eighth implementation, the intraoral scan data was generated by an intraoral scanner, and the method further comprises: receiving at least one of a plurality of x-ray images of the oral cavity of the patient, a panoramic x-ray of the oral cavity of the patient, a cone-beam computed tomography (CBCT) scan of the oral cavity of the patient, or one or more color two-dimensional images of the oral cavity of the patient, wherein the at least one of the plurality of x-ray images, the panoramic x-ray, the CBCT scan or the one or more color two-dimensional images were generated by one or more device other than an intraoral scanner; wherein processing the intraoral scan data comprises processing the intraoral scan data together with at least one of the plurality of x-ray images, the panoramic x-ray, the CBCT scan or the one or more color two-dimensional images.

A ninth implementation may further extend the first through eighth implementations. In the ninth implementation, the intraoral scan data comprises a first time stamp associated with a current or most recent patient visit, and the method further comprises: receiving second intraoral scan data of the intraoral cavity of the patient, wherein the second intraoral scan data was generated during a prior patient visit and comprises a second time stamp that predates the first time stamp; comparing the second intraoral scan data to the intraoral scan data to determine differences therebetween; and determining, for one or more dental conditions of the plurality of dental conditions, rates of change for the one or more dental conditions; wherein the severity levels for the one or more dental conditions are determined based on current states of the one or more dental conditions and the rates of change for the one or more dental conditions.

A tenth implementation may further extend the ninth implementation. In the tenth implementation, the method further comprises performing at least one of: identifying one or more new dental conditions that were detected in the current or most recent patient visit but not in the prior patient visit; identifying one or more preexisting dental conditions that have improved between the prior patient visit and the current or most recent patient visit; identifying one or more preexisting dental conditions that have worsened between the prior patient visit and the current or most recent patient visit; or identifying one or more preexisting dental conditions that have not changed between the prior patient visit and the current or most recent patient visit.

An eleventh implementation may further extend the first through tenth implementations. In the eleventh implementation, for at least one dental condition of the plurality of dental conditions, the determination of whether the dental condition is detected is based on comparison of the severity level to a threshold, wherein responsive to determining that the severity level meets or exceeds the threshold, the dental condition is classified as having been detected, and wherein responsive to determining that the severity level is below the threshold, the dental condition is classified as not having been detected. In the eleventh implementation, the method further comprises receiving an input setting a value for the threshold.

A twelfth implementation may further extend the first through eleventh implementations. In the twelfth implementation, the method further comprises ranking the plurality of dental conditions based at least in part on severity level.

A thirteenth implementation may further extend the first through twelfth implementations. In the thirteenth implementation, the method further comprises: providing, for one or more dental conditions of the plurality of dental conditions that were detected for the patient, a prognosis of the one or more dental conditions and a recommended treatment of the one or more dental conditions; receiving a selection of one or more recommended treatments; and generating a presentation comprising the one or more selected recommended treatments and associated prognoses of the one or more selected recommended treatments.

A fourteenth implementation may further extend the thirteenth implementation. In the fourteenth implementation, the method further comprises determining a cost breakdown associated with performing the one or more recommended treatments, wherein the presentation comprises the cost breakdown.

A fifteenth implementation may further extend the thirteenth implementation. In the fifteenth implementation, the method further comprises sending the presentation to a user device of the patient.

A sixteenth implementation may further extend the first through fifteenth implementations. In the sixteenth implementation, the method further comprises: for each dental condition that was detected for the patient, performing the following comprising: determining a prognosis of the dental condition; determining, based on historical information, at least one of one or more treatments performed to treat similar dental conditions or associated treatment results; and outputting an indication of at least one of the one or more treatments performed to treat the similar dental conditions or the associated treatment results.

A seventeenth implementation may further extend the first through sixteenth implementations. In the seventeenth implementation, determining whether a dental condition is detected for the patient and a severity of the dental condition comprises assigning one of a plurality of dental condition classifiers for the dental condition, wherein the plurality of dental condition classifiers comprise a first dental condition classifier indicating that the dental condition is present, a second dental condition classifier indicating that the dental condition may be present, and a third dental condition classifier indicating that the dental condition is not present.

In an eighteenth implementation, a computer readable medium includes instructions that, when executed by a processing device, cause the processing device to perform the method of any of the first through seventeenth implementations.

In a nineteenth implementation, a system comprises a memory and a processing device operatively connected to the memory, wherein the processing device is to perform the method of any of the first through seventeenth implementations.

BRIEF DESCRIPTION OF THE DRAWINGS

The present disclosure is illustrated by way of example, and not by way of limitation, in the figures of the accompanying drawings.

DETAILED DESCRIPTION

Figure 1A:
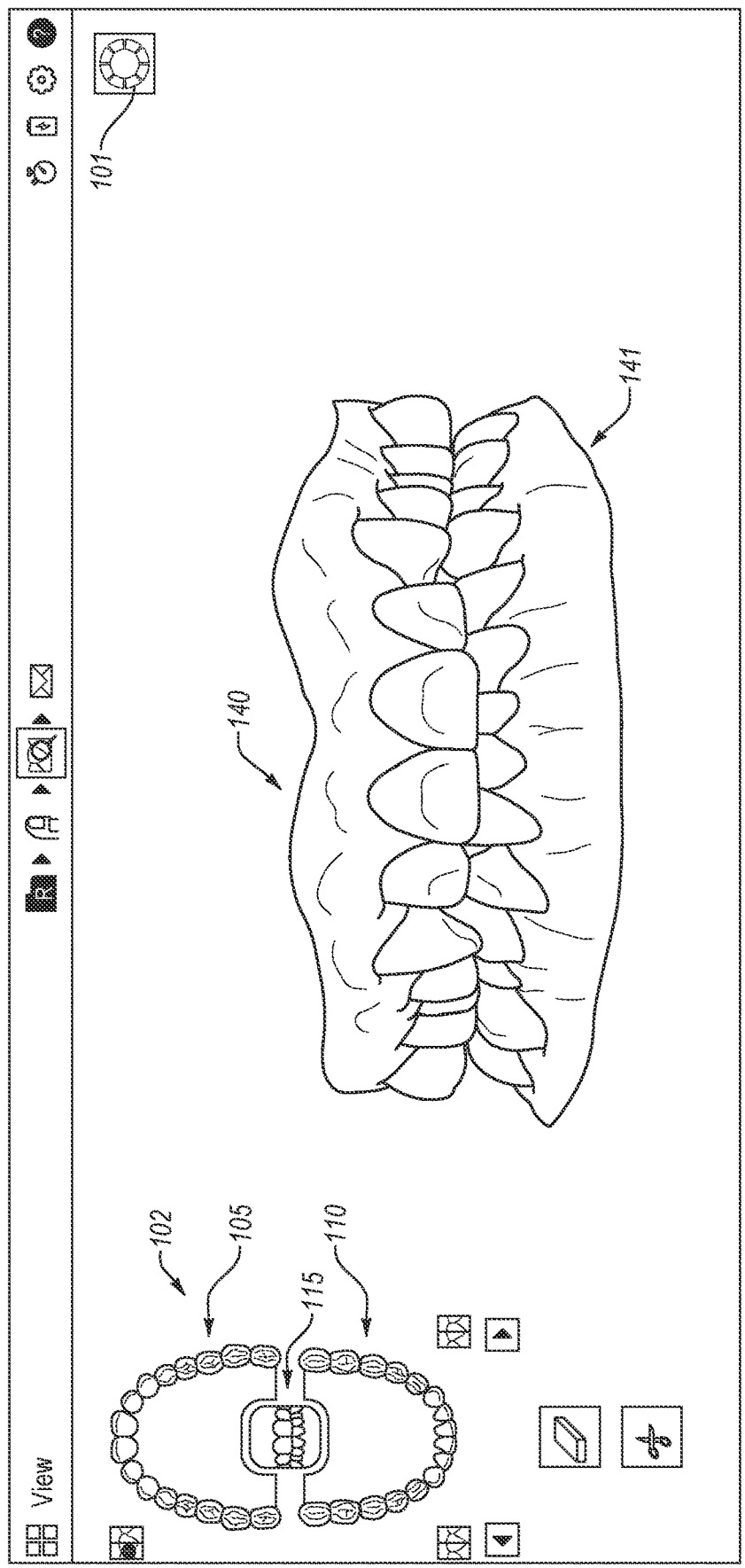
FIG. 1A illustrates a user interface of a dental diagnostics hub, in accordance with embodiments of the present disclosure.

Described herein are embodiments of a dental diagnostics hub. In embodiments, a dentist or doctor (terms used interchangeably herein) and/or their technicians may gather various information about a patient. Such information may include intraoral 3D scans of the patient's dental arches, x-rays of the patient's teeth (e.g., optionally including bite-wing x-rays of the patient's teeth, panoramic x-rays of the patient's teeth, etc.), cone-beam computed tomography (CBCT) scans of the patient's jaw, infrared images of the patient's teeth, color 2D images of the patient's teeth and/or gums, biopsy information, malocclusion information, observation notes about the patient's teeth and/or gums, and so on. The intraoral scans may be generated by an intraoral scanner, and at least some of the other data may be generated by one or more devices other than intraoral scanners. Additionally, different data may be gathered at different times. Each of the different data points may be useful for determining whether the patient has one or more types of dental conditions. The dental diagnostics hub provided in embodiments analyzes one or more of the types of data that is available for a given patient, and uses that data to assess numerous different types of dental conditions for the patient and classify or rank identified dental conditions based on severity. In embodiments, the dental diagnostics hub includes a pre-established list of clinical areas for review and systematically processes the scan data and/or other data to populate the list with actual patient data and/or analysis of the actual patient data. The dental diagnostics hub further provides a user interface that presents a unified view of each of the types of analyzed dental conditions, showing which of the types of dental conditions might be of concern and which of the types of dental conditions might not be of concern for the patient.

Traditionally, the various types of gathered information are fragmented such that each of the different types of information is stored in a separate system and accessed by a separate dentistry-related application. In order for a dentist to fully assess a patient's dental health, they generally would need to separately load and review each of the different types of data in each of the different dentistry-related applications specific to that type of data. The standard process for reviewing the data and making diagnoses involves numerous manual steps on the part of the dentist, and requires significant effort and time on the part of the dentist. Accordingly, the standard process for a dentist to perform a full analysis of a patient's dental health is highly inefficient. Moreover, once such a full analysis is made, it is generally difficult for the dentist to present the full analysis to the patient, which is again a highly manual process on the part of the dentist. What is lacking in traditional systems, and what is provided in embodiments described herein, is a way to quickly and consistently gather patient dental information in a systematic fashion and to store such information in a centralized repository. In embodiments, some of the routine steps associated with gathering and/or reviewing dental information are automated to reduce error and increase efficiency.

In embodiments, the dental diagnostics hub brings together all of the disparate types of information associated with a patient's dental health. The dental diagnostics hub further performs automated analysis for each of the different types of dental conditions. A summary result of the various automated analyses may then be shown together in a graphical user interface (GUI). The summary result of the various automated analyses may include a severity rating for each of the types of dental conditions. The summary result may identify those dental conditions having higher severity levels to call them to the attention of the dentist. The dentist may then select any of the types of dental conditions to cause the dental diagnostics hub to provide more detailed information about the selected type of dental condition for the patient.

In embodiments, the dental diagnostics hub greatly increases the speed and efficiency of diagnosing dental conditions of patients. The dental diagnostics hub enables a dentist to determine, at a single glance of the GUI for the dental diagnostics hub, all of the dental conditions that might be of concern for a patient. It enables the dentist to easily and quickly prioritize dental conditions to be addressed. Additionally, the dental diagnostics hub may compare different identified dental conditions to determine any correlations between different identified dental conditions. As a result, the dental diagnostics hub may identify some dental conditions as symptoms of other underlying root cause dental conditions. For example, the dental diagnostics hub may identify tooth crowding and caries formation that results from the tooth crowding. Additionally, the dental diagnostics hub in embodiments creates presentations of dental conditions, what will happen if those dental conditions are untreated, root causes of the patient's dental conditions, treatment plan options, and/or simulations of treatment results. Such presentations may be shown to the patient to educate the patient about the condition of their dentition and their options for treating the problems and/or leaving the problems untreated.

A dental practitioner (e.g., a dentist or dental technician) may use an intraoral scanner to perform an intraoral scan of a patient's oral cavity. An intraoral scan application running on a computing device operatively connected to the intraoral scanner may communicate with the scanner to effectuate intraoral scanning and receive intraoral scan data (also referred to as intraoral images and intraoral scans). A result of the intraoral scanning may be a sequence of intraoral scans that have been discretely generated (e.g., by pressing on a "generate scan" button of the scanner for each image) or automatically generated (e.g., by pressing a "start scanning" button and moving the intraoral scanner around the oral cavity while multiple intraoral scans are generated). An operator may start performing intraoral scanning at a first position in the oral cavity, and move the intraoral scanner within the oral cavity to various additional positions until intraoral scans have been generated for an entirety of one or more dental arches or until a particular dental site is fully scanned. In some embodiments, recording of intraoral scans may start automatically as teeth are detected or insertion into the oral cavity is detected and may automatically be paused or stopped as removal of the intraoral scanner from the oral cavity is detected.

According to an example, a user (e.g., a dental practitioner) may subject a patient to intraoral scanning. In doing so, the user may apply the intraoral scanner to one or more patient intraoral locations. The scanning may be divided into one or more segments. As an example the segments may include a lower buccal region of the patient, a lower lingual region of the patient, a upper buccal region of the patient, an upper lingual region of the patient, one or more preparation teeth of the patient (e.g., teeth of the patient to which a dental device such as a crown or an orthodontic alignment device will be applied), one or more teeth which are contacts of preparation teeth (e.g., teeth not themselves subject to a dental device but which are located next to one or more such teeth or which interface with one or more such teeth upon mouth closure), and/or patient bite (e.g., scanning performed with closure of the patient's mouth with scan being directed towards an interface area of the patient's upper and lower teeth). In one embodiment, the segments include an upper dental arch segment, a lower dental arch segment and a patient bite segment. Via such scanner application, the scanner may generate intraoral scan data. The computing device executing the intraoral scan application may receive and store the intraoral scan data. The intraoral scan data may include two-dimensional (2D) intraoral images (e.g., color 2D images), three-dimensional intraoral scans (e.g., intraoral images with depth information such as monochrome height maps), intraoral images generated using infrared or near-infrared (NIRI) light, and/or intraoral images generated using ultraviolet light. The 2D color images, 3D scans, NIRI and/or infrared images and/or ultraviolet images may be generated by an intraoral scanner capable of generating each of these types of intraoral scan data. Such intraoral scan data may be provided from the scanner to the computing device in the form of one or more points (e.g., one or more pixels and/or groups of pixels). For instance, the scanner may provide such intraoral scan data as one or more point clouds.

In embodiments, intraoral scanning may be performed on a patient's oral cavity during a visitation of a dentist's office. The intraoral scanning may be performed, for example, as part of a semi-annual or annual dental health checkup. The intraoral scanning may be a full scan of the upper and lower dental arches, and may be performed in order to gather information for performing dental diagnostics. The dental information generated from the intraoral scanning may include 3D scan data, 2D color images, NIRI and/or infrared images, and/or ultraviolet images.

In addition to performing intraoral scanning, a dental practitioner may generate one or more other types of relevant dental health information, such as x-rays of the patient's teeth (e.g., optionally including bitewing x-rays of the patient's teeth, panoramic x-rays of the patient's teeth, etc.), cone-beam computed tomography (CBCT) scans of the patient's jaw, infrared images of the patient's teeth, color 2D images of the patient's teeth and/or gums not generated by an intraoral scanner (e.g., from photos taken by a camera), biopsy information, malocclusion information, observation notes about the patient's teeth and/or gums, and so on. For example, in addition to a dental practitioner generating an intraoral scan of the oral cavity during an annual or semi-annual dentist appointment, the dental practitioner may additionally generate one or more x-rays of the patient's oral cavity during the dentist appointment. Additional types of dental information may also be gathered when the dentist deems it appropriate to generate such additional information. For example, the dentist may take biopsy samples and send them to a lab for testing and/or may generate a panoramic x-ray and/or a CBCT scan of the patient's oral cavity.

The intraoral scan application may generate a 3D model (e.g., a virtual 3D model) of the upper and/or lower dental arches of the patient from the intraoral scan data. To generate the 3D model(s) of the dental arches, the intraoral scan application may register and stitch together the intraoral scans generated from the intraoral scan session. In one embodiment, performing image registration includes capturing 3D data of various points of a surface in multiple intraoral scans, and registering the intraoral scans by computing transformations between the intraoral scans. The intraoral scans may then be integrated into a common reference frame by applying appropriate transformations to points of each registered intraoral scan.

In one embodiment, registration is performed for each pair of adjacent or overlapping intraoral scans. Registration algorithms may be carried out to register two adjacent intraoral scans for example, which essentially involves determination of the transformations which align one intraoral scan with the other. Registration may involve identifying multiple points in each intraoral scan (e.g., point clouds) of a pair of intraoral scans, surface fitting to the points of each intraoral scans, and using local searches around points to match points of the two adjacent intraoral scans. For example, the intraoral scan application may match points, edges, curvature features, spin-point features, etc. of one intraoral scan with the closest points, edges, curvature features, spin-point features, etc. interpolated on the surface of the other intraoral scan, and iteratively minimize the distance between matched points. Registration may be repeated for each adjacent and/or overlapping scans to obtain transformations (e.g., rotations around one to three axes and translations within one to three planes) to a common reference frame. Using the determined transformations, the intraoral scan application may integrate the multiple intraoral scans into a first 3D model of the lower dental arch and a second 3D model of the upper dental arch.

The intraoral scan data may further include one or more intraoral scans showing a relationship of the upper dental arch to the lower dental arch. These intraoral scans may be usable to determine a patient bite and/or to determine occlusal contact information for the patient. The patient bite may include determined relationships between teeth in the upper dental arch and teeth in the lower dental arch.

The intraoral scan application or another application may further register data from one or more other imaging modalities to the 3D model generated from the intraoral scan data. For example, processing logic may register x-ray images, CBCT scan data, ultrasound images, panoramic x-ray images, 2D color images, NIRI images, and so on to the 3D model. Each of the different imaging modalities may contribute different information about the patient's dentition. For example, NIRI images and x-ray images may identify caries and color images may be used to add accurate color data to the 3D model, which is usable to determine tooth staining. The registered intraoral data from the multiple imaging modalities may be presented together in the 3D model and/or side-by-side with one or more imaging modalities shown that reflect a zoomed in and/or highlighted section and/or orientation of the 3D model. The data from different imaging modalities may be provided as different layers, where each layer may be for a particular imaging modality. This may enable a doctor to turn on or off specific layers to visualize the dental arch with or without information from those particular imaging modalities.

FIG. 1A illustrates a user interface of a dental diagnostics hub, in accordance with embodiments of the present disclosure. A 3D model of a patient's upper dental arch 140 and a 3D model of the patient's lower dental arch 141 may be generated by an intraoral scan application and input into the dental diagnostics hub. Additionally, bite data showing the relationship of the upper dental arch 140 and the lower dental arch 141 may be input into the dental diagnostics hub. The bite relationship data may also include how the upper and lower jaw dynamically relate to each other in functional motions and not just in a static relationship relative to each other. This can be useful for diagnostic problems related to the jaw joint (e.g., temporomandibular (TMJ) disorders). Additionally, intraoral scans may have been generated of one or more preparation tooth of the patient, which may also be input to the dental diagnostics hub. The dental diagnostics hub may then present a view of the upper dental arch 140, the lower dental arch 141, the preparation teeth, and/or the relative positions of the upper and lower dental arches 140, 141 in the user interface of the dental diagnostics hub.

Via the user interface of the dental diagnostics hub, a practitioner may view one or more of the upper dental arch 140, the lower dental arch 141, a particular preparation tooth and/or the patient bite, each of which may be considered a separate scan segment or mode. The practitioner may select one or multiple scan segments to view via a scan segment selector 102. In one embodiment, as shown, the scan segment selector 102 may include an upper dental arch segment selection 105, a lower dental arch segment selection 110 and a bite segment selection 115. As illustrated, the upper dental arch segment selection 105 and the lower dental arch segment selection 110 are active, causing the 3D model of the upper dental arch 140 and the 3D model of the lower dental arch 141 to be shown. A practitioner may rotate the 3D models and/or change a zoom setting for a view of the 3D models using the GUI.

The GUI of the dental diagnostics hub may further include a diagnostics command 101. Selection of the diagnostics command 101 may cause the dental diagnostics hub to perform one or multiple different analyses of the patient's dental arches 140, 141 and/or bite. The analyses may include an analysis for identifying tooth cracks, an analysis for identifying gum recession, an analysis for identifying tooth wear, an analysis of the patient's occlusal contacts, an analysis for identifying crowding of teeth (and/or spacing of teeth) and/or other malocclusions, an analysis for identifying plaque, an analysis for identifying tooth stains, an analysis for identifying caries, and/or other analyses of the patient's dentition. Once the analyses are complete, a dental diagnostics summary may be generated and shown in the GUI of the dental diagnostics hub, as shown in FIG. 1C.

Some of the analyses that are performed to assess the patient's dental health are dental condition progression analyses that compare dental conditions of the patient at multiple different points in time. For example, one carries assessment analysis may include comparing caries at a first point in time and a second point in time to determine a change in severity of the caries between the two points in time, if any. Other time-based comparative analyses that may be performed include a time-based comparison of gum recession, a time-based comparison of tooth wear, a time-based comparison of tooth movement, a time-based comparison of tooth staining, and so on. In some embodiments, processing logic automatically selects data collected at different points in time to perform such time-based analyses. Alternatively, a user may manually select data from one or more points in time to use for performing such time-based analyses.

Figure 1B:
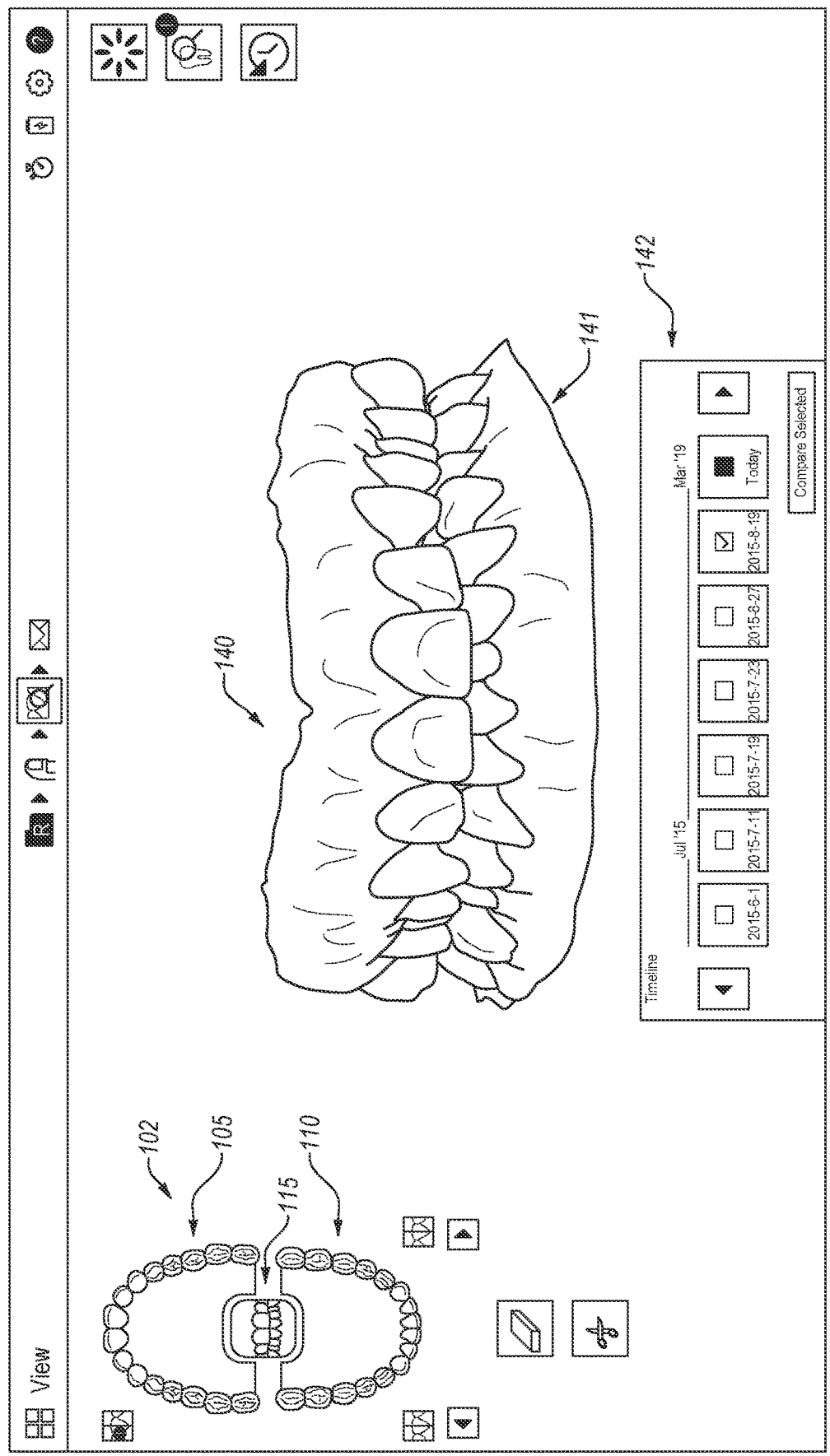
FIG. 1B illustrates a user interface of a dental diagnostics hub, showing a time-lapse feature, in accordance with embodiments of the present disclosure.
Figure 1C:
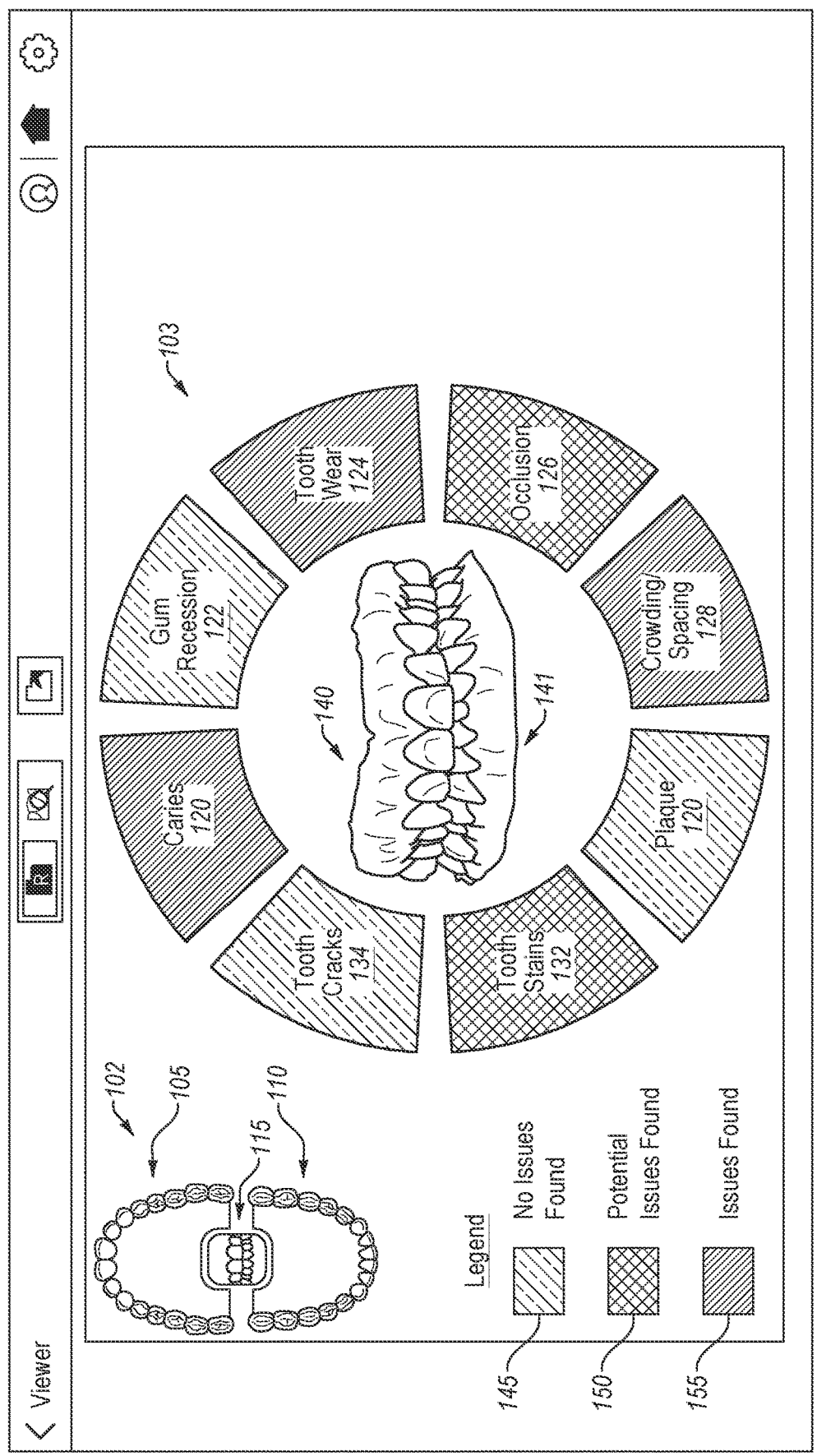
FIG. 1C illustrates a user interface of a dental diagnostics hub after diagnostics have been run on a patient's dental arches, in accordance with embodiments of the present disclosure.

FIG. 1B illustrates a user interface of a dental diagnostics hub, showing a time-lapse feature 142, in accordance with embodiments of the present disclosure. In one embodiment, the time-lapse feature is launched automatically when a user selects the diagnostics command 101 to provide the user an option to select which dental information from which points in time to use for the analyses to be performed. In one embodiment, the time lapse feature 142 shows each of the different points in time (i.e., different times stamps) at which dental information was collected along a time line. The dental information that may be selected may include at a minimum intraoral scan data (e.g., 3D models generated based on one or more intraoral scanning sessions). The dental information that may be selected may further include x-rays generated at various points in time, CBCT scan data generated at various points in time, and/or other dental information generated at various points in time. Via the time lapse feature 142, a user may select one or more past data points (e.g., for previously generated 3D models of dental arches) and/or one or more current data points or most recent data points (e.g., for a current 3D model of the dental arches). The selected data points may then be used to perform one or more time-based analyses of the patient's dentition.

In embodiments, the time-based analyses of the patient's dentition compare 3D models and/or one or more dental conditions of the patient over time, and identify dental conditions and/or determine a rate of progression of the one or more dental conditions based on the comparison. For example, 3D models of the dental arches from different points in time may be compared to one another to determine rates of progression of tooth wear, caries development, gum recession, gum swelling, malocclusions, and so on. The rates of progression may be compared to rate of progression thresholds. The rate of progression thresholds may be set by a doctor or may be set to defaults. Amount of change for dental conditions may also be determined, and may be compared to amount of change thresholds. Those dental conditions for which the rate of progression meets or exceeds a rate of progression threshold for that dental condition and/or for which amount of change meets or exceeds an amount of change threshold may be identified as dental conditions that are of clinical significance and/or dental conditions for which issues or problems have been identified.

The time-based analyses may project detected rates of progression or rates of change of one or more dental conditions into the future to predict severity levels of the dental conditions at future points in time. In embodiments, progression of one or more dental conditions may be projected into the future, and the predicted dental condition at each projected point in time may be compared to one or more criteria (e.g., such as a severity threshold). The one or more criteria may be default criteria and/or may be criteria set by a doctor (e.g., a user of the dental diagnostics hub). The criteria may also be set by aggregated data, either within the same practice or through a network of practices of similar patient traits. When the one or more criteria are satisfied, that indicates that a dental condition of clinical significance is identified. The future point in time at which a projected dental condition will satisfy the one or more criteria (e.g., pass the severity threshold) may be noted and added to the patient's record in embodiments. In embodiments, if the future point in time at which a projected dental condition will satisfy the one or more criteria for that dental condition is within a threshold amount of time from a current date, then the dental condition may be identified as of clinical importance or of potential clinical importance.

FIG. 1C illustrates a user interface of a dental diagnostics hub showing a dental diagnostics summary 103 after diagnostics have been run on a patient's dental arches, in accordance with embodiments of the present disclosure. In embodiments, the dental diagnostics summary 103 includes the scan segment selector 102 including upper dental arch segment selection 105, lower dental arch segment selection 110 and/or bite segment selection 115. In embodiments, the dental diagnostics summery 103 further includes views of the selected dental segments or modes (e.g., of the 3D model of the upper dental arch 140 and the 3D model of the lower dental arch 141 of the patient).

The dental diagnostics summary 103 provides a single view showing multiple different types of possible dental conditions and assessments as to the presence and/or severity of each of the types of dental conditions. In one embodiment, the various dental conditions are assigned one of three severity levels, including "no issues found" 145, "potential issues found" 150 and "issues found" 155. Each of the dental conditions may be coded or labeled with the severity ranking determined for that type of dental condition. In one embodiment, the dental conditions are color coded to graphically show severity levels. For example, those dental conditions for which issues were found may be coded red, those dental conditions for which potential issues were found may be coded yellow, and those dental conditions for which no issues were found may be coded green. Many other coding schemes are also possible. In one embodiment, each of the dental conditions is assigned a numeric severity level. For example, on a scale of 1 to 100, each dental condition may be assigned a severity level between 1 and 100 to indicate the severity level of that dental condition. Those dental conditions with a severity level that is below a first threshold severity level may be identified as dental conditions for which no issues were found. Those dental conditions for which the severity level is above the first threshold severity level but below a second threshold severity level may be identified as dental conditions for which potential issues were found. Those dental conditions for which the severity level is above the second severity level threshold may be identified as dental conditions for which issues were found. In embodiments, different severity level thresholds may be set for each of the different dental conditions. Alternatively, the severity levels of the different dental conditions may be normalized across the multiple types of dental conditions and the same severity level thresholds may be used for multiple dental conditions. In some embodiments, dental conditions are ranked based on their severity levels and/or based on the different between their severity levels and the associated severity level threshold for the dental conditions.

In embodiments, a doctor may set severity level thresholds for one or more of the dental conditions. Severity level thresholds that a doctor may set may be point-in-time severity level thresholds for point-in-time severity levels of dental conditions determined based on data from a single point in time. Additionally, or alternatively, severity level thresholds that a doctor may set may be time-dependent thresholds, such as amount of change thresholds and rate of change thresholds. Alerts may be set to remind the doctor when the threshold level is approaching specific criteria.

Absent such selected severity level thresholds, default severity level thresholds may be automatically set for one or more of the dental conditions. In an example, a doctor may set a caries size threshold, and any detected caries that have a size that meets or exceeds the set caries size threshold may be identified as a found issue. In another example, a doctor may set a gum recession amount threshold, and any identified gum recession that has a value that meets or exceeds the gum recession amount threshold may be identified as a found issue. A doctor may also set rate of change thresholds for one or more dental conditions and/or such rate of change thresholds may be automatically set to default values. For example, if the rate of change of tooth wear exceeds a tooth wear rate of change threshold, then the patient may be identified as having an identified tooth wear issue. A doctor may also set an amount of change threshold. If a detected amount of change is greater than the set amount of change threshold for a dental condition, then the doctor may be alerted. Multiple different units may be used to set severity level thresholds, such as units of distance (e.g., microns, millimeters, fractions of an inch, etc.), units of size (e.g., microns, millimeters, fractions of an inch, etc.), units of rates of change (e.g., microns/month, millimeters per year, etc.), units of luminance, units of volume (e.g., $mm^3$), units of area (e.g., $mm^2$), ratios, percentages (e.g., percentage of change), and so on.

In embodiments, severity level thresholds may depend at least in part on a location of an identified dental condition. For example, different caries severity thresholds may be set for different locations. Caries that are close to dentin may be more urgent because they are more likely to cause pain and/or to require a root canal than caries that are far from dentin. Accordingly, caries that are close to dentin may have a lower threshold than caries that are far from dentin, for example. In embodiments, the distance between a caries and a patient's dentin may be determined based on x-ray data, a CBCT scan and/or NIRI imaging of the intraoral cavity.

In one embodiment, the different types of dental conditions for which analyses are performed and that are included in the dental diagnostics summary 103 include tooth cracks, gum recession, tooth wear, occlusal contacts, crowding and/or spacing of teeth and/or other malocclusions, plaque, tooth stains, and caries. Additional, fewer and/or alternative dental conditions may also be analyzed and reported in the dental diagnostics summary 103. In embodiments, multiple different types of analyses are performed to determine presence and/or severity of one or more of the dental conditions. One type of analysis that may be performed is a point-in-time analysis that identifies the presence and/or severity levels of one or more dental conditions at a particular point-in-time based on data generated at that point-in-time. For example, a single 3D model of a dental arch may be analyzed to determine whether, at a particular point-in-time, a patient's dental arch included any caries, gum recession, tooth wear, problem occlusion contacts, crowding, spacing or tooth gaps, plaque, tooth stains, and/or tooth cracks. Another type of analysis that may be performed is a time-based analysis that compares dental conditions at two or more points in time to determine changes in the dental conditions, progression of the dental conditions and/or rates of change of the dental conditions, as discussed with reference to FIG. 1B. For example, in embodiments a comparative analysis is performed to determine differences between 3D models of dental arches taken at different points in time. The differences may be measured to determine an amount of change, and the amount of change together with the times at which the intraoral scans that were used to generate the 3D models were taken may be used to determine a rate of change. This technique may be used, for example, to identify an amount of change and/or a rate of change for tooth wear, staining, plaque, crowding, spacing, gum recession, caries development, tooth cracks, and so on.

In embodiments, one or more trained models are used to perform at least some of the one or more dental condition analyses. The trained models may include physics models and/or machine learning models, for example. In one embodiment, a single model may be used to perform multiple different analyses (e.g., to identify any combination of tooth cracks, gum recession, tooth wear, occlusal contacts, crowding and/or spacing of teeth and/or other malocclusions, plaque, tooth stains, and/or caries). Additionally, or alternatively, different models may be used to identify different dental conditions. For example, a first model may be used to identify tooth cracks, a second model may be used to identify tooth wear, a third model may be used to identify gum recession, a fourth model may be used to identify problem occlusal contacts, a fifth model may be used to identify crowding and/or spacing of teeth and/or other malocclusions, a sixth model may be used to identify plaque, a sixth model may be used to identify tooth stains, and/or a seventh model may be used to identify caries.

In one embodiment, intraoral data from one or more points in time are input into one or more trained machine learning models that have been trained to receive the intraoral data as an input and to output classifications of one or more types of dental conditions. In one embodiment, the trained machine learning model(s) is trained to identify areas of interest (AOIs) from the input intraoral data and to classify the AOIs based on dental conditions. The AOIs may be or include regions associated with particular dental conditions. The regions may include nearby or adjacent pixels or points that satisfy some criteria, for example. The intraoral data that is input into the one or more trained machine learning model may include three-dimensional (3D) data and/or two-dimensional (2D) data. The intraoral data may include, for example, one or more 3D models of a dental arch, one or more projections of one or more 3D models of a dental arch onto one or more planes (optionally comprising height maps), one or more x-rays of teeth, one or more CBCT scans, a panoramic x-ray, near-infrared and/or infrared imaging data, color image(s), ultraviolet imaging data, intraoral scans, and so on. If data from multiple imaging modalities are used (e.g., 3D scan data, color images, and NIRI imaging data), then the data may be registered and/or stitched together so that the data is in a common reference frame and objects in the data are correctly positioned and oriented relative to objects in other data. One or more feature vectors may be input into the trained model, where the feature vectors include multiple channels of information for each point or pixel of an image. The multiple channels of information may include color channel information from a color image, depth channel information from intraoral scan data, a 3D model or a projected 3D model, intensity channel information from an x-ray image, and so on.

The trained machine learning model(s) may output a probability map, where each point in the probability map corresponds to a point in the intraoral data (e.g., a pixel in an intraoral image or point on a 3D surface) and indicates probabilities that the point represents one or more dental classes. In one embodiment, a single model outputs probabilities associated with multiple different types of dental classes, which includes one or more dental condition classes. In an example, a trained machine learning model may output a probability map with probability values for a teeth dental class and a gums dental class. The probability map may further include probability values for tooth cracks, gum recession, tooth wear, occlusal contacts, crowding and/or spacing of teeth and/or other malocclusions, plaque, tooth stains, healthy area (e.g., healthy tooth and/or healthy gum) and/or caries. In the case of a single machine learning model that can identify each of tooth cracks, gum recession, tooth wear, occlusal contacts, crowding and/or spacing of teeth and/or other malocclusions, plaque, tooth stains, and caries, eleven valued labels may be generated for each pixel, one for each of teeth, gums, healthy area, tooth cracks, gum recession, tooth wear, occlusal contacts, crowding and/or spacing of teeth and/or other malocclusions, plaque, tooth stains, and caries. The corresponding predictions have a probability nature: for each pixel there are multiple numbers that may sum up to 1.0 and can be interpreted as probabilities of the pixel to correspond to these classes. In one embodiment, the first two values for teeth and gums sum up to 1.0 and the remaining values for healthy area, tooth cracks, gum recession, tooth wear, occlusal contacts, crowding and/or spacing of teeth and/or other malocclusions, plaque, tooth stains, and/or caries sum up to 1.0.

In some instances, multiple machine learning models are used, where each machine learning model identifies a subset of the possible dental conditions. For example, a first trained machine learning model may be trained to output a probability map with three values, one each for healthy teeth, gums, and caries. Alternatively, the first trained machine learning model may be trained to output a probability map with two values, one each for healthy teeth and caries. A second trained machine learning model may be trained to output a probability map with three values (one each for healthy teeth, gums and tooth cracks) or two values (one each for healthy teeth and tooth cracks). One or more additional trained machine learning models may each be trained to output probability maps associated with identifying specific types of dental conditions.

In case of an ML model trained to identify three classes, it is convenient to store such predictions of dental classes in an RGB format. For example, a first value for a first dental class may be stored as a red intensity value, a second value for a second dental class may be stored as a green intensity value, and a third value for a third dental class may be stored as a blue intensity value. This may make visualization of the probability map very easy. Usually, there is no need in high precision and chars can be used instead of floats—that is 256 possible values for every channel of the pixel. Further optimization can be done in order to reduce the size and improve performance (e.g., use 16 values quantization instead of 256 values).

The output of the one or more trained machine learning models may be used to update one or more versions of the 3D model of the patient's upper and/or lower dental arches. In one embodiment, a different layer is generated for each dental condition class. A layer may be turned on to graphically illustrate areas of interest on the upper and/or lower dental arch that has been identified or flagged as having a particular dental condition.

If the probability maps were generated for one or more input 2D images (e.g., such as height maps in which pixel intensity represents height or depth), the probability maps output by the ML model(s) may be projected onto the points in the virtual 3D model. Accordingly, each point in the virtual 3D model may include probability information from probability maps of one or multiple different intraoral images that map to that point. In one embodiment, the probability information from the probability map is projected onto the 3D model as a texture. The updated 3D model may then include, for one or more points, vertexes or voxels of the 3D model (e.g., vertexes on a 3D mesh that represents the surface of the 3D model), multiple sets of probabilities, where different sets of probabilities associated with probability maps generated for different input images or other intraoral data may have different probability values.

Processing logic may modify the virtual 3D model by determining, for each point in the virtual 3D model, one or more dental class for that point. This may include using a voting function to determine a dental class for each point. For example, each set of probability values from an intraoral image may indicate a particular dental class. Processing logic may determine the number of votes for each dental class for a point, and may then classify the point as having a dental class that receives the most votes. In some embodiments, points may be associated with multiple classes of dental conditions.

In embodiments, image processing and/or 3D data processing may be performed on 3D models of dental arches generated from intraoral scans and/or on the output of one or more trained models. Such image processing and/or 3D data processing may be performed using one or more algorithms, which may be generic to multiple types of dental conditions or may be specific to particular dental conditions. For example, a trained model may identify regions on a 3D model of a dental arch that include caries, and image processing may be performed to assess the size and/or severity of the identified caries. The image processing may include performing automated measurements such as size measurements, distance measurements, amount of change measurements, rate of change measurements, ratios, percentages, and so on. Accordingly, the image processing and/or 3D data processing may be performed to determine severity levels of dental conditions identified by the trained model(s). Alternatively, the trained models may be trained both to classify regions as caries and to identify a severity and/or size of the caries.

The one or more trained machine learning models that are used to identify, classify and/or determine a severity level for dental conditions may be neural networks such as deep neural networks or convolutional neural networks. Such machine learning models may be trained using supervised training in embodiments.

Artificial neural networks (e.g., deep neural networks and convolutional neural networks) generally include a feature representation component with a classifier or regression layers that map features to a desired output space. A convolutional neural network (CNN), for example, hosts multiple layers of convolutional filters. Pooling is performed, and non-linearities may be addressed, at lower layers, on top of which a multi-layer perceptron is commonly appended, mapping top layer features extracted by the convolutional layers to decisions (e.g. classification outputs). Deep learning is a class of machine learning algorithms that use a cascade of multiple layers of nonlinear processing units for feature extraction and transformation. Each successive layer uses the output from the previous layer as input. Deep neural networks may learn in a supervised (e.g., classification) and/or unsupervised (e.g., pattern analysis) manner. Deep neural networks include a hierarchy of layers, where the different layers learn different levels of representations that correspond to different levels of abstraction. In deep learning, each level learns to transform its input data into a slightly more abstract and composite representation. In an image recognition application, for example, the raw input may be a matrix of pixels; the first representational layer may abstract the pixels and encode edges; the second layer may compose and encode arrangements of edges; the third layer may encode higher level shapes (e.g., teeth, lips, gums, etc.); and the fourth layer may recognize that the image contains a face or define a bounding box around teeth in the image. Notably, a deep learning process can learn which features to optimally place in which level on its own. The "deep" in "deep learning" refers to the number of layers through which the data is transformed. More precisely, deep learning systems have a substantial credit assignment path (CAP) depth. The CAP is the chain of transformations from input to output. CAPs describe potentially causal connections between input and output. For a feedforward neural network, the depth of the CAPs may be that of the network and may be the number of hidden layers plus one. For recurrent neural networks, in which a signal may propagate through a layer more than once, the CAP depth is potentially unlimited.

In one embodiment, a U-net architecture is used. A U-net is a type of deep neural network that combines an encoder and decoder together, with appropriate concatenations between them, to capture both local and global features. The encoder is a series of convolutional layers that increase the number of channels while reducing the height and width when processing from inputs to outputs, while the decoder increases the height and width and reduces the number of channels. Layers from the encoder with the same image height and width may be concatenated with outputs from the decoder. Any or all of the convolutional layers from encoder and decoder may use traditional or depth-wise separable convolutions.

In one embodiment, the machine learning model is a recurrent neural network (RNN). An RNN is a type of neural network that includes a memory to enable the neural network to capture temporal dependencies. An RNN is able to learn input-output mappings that depend on both a current input and past inputs. The RNN will address past and future intraoral data (e.g., intraoral scans taken at different times) and make predictions based on information that spans multiple time periods and/or patient visits. RNNs may be trained using a training dataset to generate a fixed number of outputs. One type of RNN that may be used is a long short term memory (LSTM) neural network.

A common architecture for such tasks is LSTM (Long Short Term Memory). Unfortunately, LSTM is not well suited for images since it does not capture spatial information as well as convolutional networks do. For this purpose, one can utilize ConvLSTM—a variant of LSTM containing a convolution operation inside the LSTM cell. ConvLSTM is a variant of LSTM (Long Short-Term Memory) containing a convolution operation inside the LSTM cell. ConvLSTM replaces matrix multiplication with a convolution operation at each gate in the LSTM cell. By doing so, it captures underlying spatial features by convolution operations in multiple-dimensional data. The main difference between ConvLSTM and LSTM is the number of input dimensions. As LSTM input data is one-dimensional, it is not suitable for spatial sequence data such as video, satellite, radar image data set. ConvLSTM is designed for 3-D data as its input. In one embodiment, a CNN-LSTM machine learning model is used. A CNN-LSTM is an integration of a CNN (Convolutional layers) with an LSTM. First, the CNN part of the model processes the data and a one-dimensional result feeds an LSTM model. The network architecture for excess material removal may look as is shown in FIGS. 11A-B in one embodiment, which includes a ConvLSTM machine learning model.

In one embodiment, a class of machine learning model called a MobileNet is used. A MobileNet is an efficient machine learning model based on a streamlined architecture that uses depth-wise separable convolutions to build light weight deep neural networks. MobileNets may be convolutional neural networks (CNNs) that may perform convolutions in both the spatial and channel domains. A MobileNet may include a stack of separable convolution modules that are composed of depthwise convolution and pointwise convolution (conv 1×1). The separable convolution independently performs convolution in the spatial and channel domains. This factorization of convolution may significantly reduce computational cost from HWNK2M to HWNK2 (depthwise) plus HWNM (conv 1×1), HWN(K2+M) in total, where N denotes the number of input channels, K2 denotes the size of convolutional kernel, M denotes the number of output channels, and H×W denotes the spatial size of the output feature map. This may reduce a bottleneck of computational cost to conv 1×1.

In one embodiment, a generative adversarial network (GAN) is used. A GAN is a class of artificial intelligence system that uses two artificial neural networks contesting with each other in a zero-sum game framework. The GAN includes a first artificial neural network that generates candidates and a second artificial neural network that evaluates the generated candidates. The GAN learns to map from a latent space to a particular data distribution of interest (a data distribution of changes to input images that are indistinguishable from photographs to the human eye), while the discriminative network discriminates between instances from a training dataset and candidates produced by the generator. The generative network's training objective is to increase the error rate of the discriminative network (e.g., to fool the discriminator network by producing novel synthesized instances that appear to have come from the training dataset). The generative network and the discriminator network are co-trained, and the generative network learns to generate images that are increasingly more difficult for the discriminative network to distinguish from real images (from the training dataset) while the discriminative network at the same time learns to be better able to distinguish between synthesized images and images from the training dataset. The two networks of the GAN are trained once they reach equilibrium. The GAN may include a generator network that generates artificial intraoral images and a discriminator network that segments the artificial intraoral images. In embodiments, the discriminator network may be a MobileNet.

In one embodiment, the machine learning model is a conditional generative adversarial (cGAN) network, such as pix2pix. These networks not only learn the mapping from input image to output image, but also learn a loss function to train this mapping. GANs are generative models that learn a mapping from random noise vector z to output image y, G: z→y. In contrast, conditional GANs learn a mapping from observed image x and random noise vector z, to y, G: {x, z}→y. The generator G is trained to produce outputs that cannot be distinguished from "real" images by an adversarially trained discriminator, D, which is trained to do as well as possible at detecting the generator's "fakes". The generator may include a U-net or encoder-decoder architecture in embodiments. The discriminator may include a MobileNet architecture in embodiments. An example of a cGAN machine learning architecture that may be used is the pix2pix architecture described in Isola, Phillip, et al. "Image-to-image translation with conditional adversarial networks." arXiv preprint (2017).

Training of a neural network may be achieved in a supervised learning manner, which involves feeding a training dataset consisting of labeled inputs through the network, observing its outputs, defining an error (by measuring the difference between the outputs and the label values), and using techniques such as deep gradient descent and back-propagation to tune the weights of the network across all its layers and nodes such that the error is minimized. In many applications, repeating this process across the many labeled inputs in the training dataset yields a network that can produce correct output when presented with inputs that are different than the ones present in the training dataset. In high-dimensional settings, such as large images, this generalization is achieved when a sufficiently large and diverse training dataset is made available.

To train the one or more machine learning models, a training dataset (or multiple training datasets, one for each of the machine learning models to be trained) containing hundreds, thousands, tens of thousands, hundreds of thousands or more images should be used to form a training dataset. In embodiments, up to millions of cases of patient dentition that include one or more labeled dental conditions such as cracked teeth, tooth wear, caries, gum recession, gum swelling, tooth stains, healthy teeth, healthy gums, and so on are used, where each case may include a final virtual 3D model of a dental arch (or other dental site such as a portion of a dental arch). The machine learning models may be trained to automatically classify and/or segment intraoral scans after an intraoral scanning session, and the segmentation/classification may be used to automatically determine presence and/or severity of dental conditions.

For each 3D model with labeled dental classes, a set of images (e.g., height maps) may be generated. Each image may be generated by projecting the 3D model (or a portion of the 3D model) onto a 2D surface or plane. Different images of a 3D model may be generated by projecting the 3D model onto different 2D surfaces or planes in some embodiments. For example, a first image of a 3D model may be generated by projecting the 3D model onto a 2D surface that is in a top down point of view, a second image may be generated by projecting the 3D model onto a 2D surface that is in a first side point of view (e.g., a buccal point of view), a third image may be generated by projecting the 3D model onto a 2D surface that is in a second side point of view (e.g., a lingual point of view), and so on. Each image may include a height map that includes a depth value associated with each pixel of the image. For each image, a probability map or mask may be generated based on the labeled dental classes in the 3D model and the 2D surface onto which the 3D model was projected. The probability map or mask may have a size that is equal to a pixel size of the generated image. Each point or pixel in the probability map or mask may include a probability value that indicates a probability that the point represents one or more dental classes. For example, there may be three dental classes, including a first dental class representing caries, a second dental class representing healthy teeth, and a third dental class representing gums. Points that have a first dental class may have a value of (1,0,0) (100% probability of first dental class and 0% probability of second and third dental classes), points that have a second dental class may have a value of (0,1,0), and points that have a third dental class may have a value of (0,0,1), for example.

A training dataset may be gathered, where each data item in the training dataset may include an image (e.g., an image comprising a height map) and an associated probability map. Additional data may also be included in the training data items. Accuracy of segmentation can be improved by means of additional classes, inputs and multiple views support. Multiple sources of information can be incorporated into model inputs and used jointly for prediction. Multiple dental classes can be predicted concurrently from a single model. Multiple problems can be solved simultaneously: teeth/gums segmentation, dental condition classification, etc. Accuracy is higher than traditional image and signal processing approaches.

Additional data may include a color image. For example, for each image (which may be a monochrome), there may also be a corresponding color image. Each data item may include depth information (e.g., a height map) as well as color information (e.g., from a color image). Two different types of color images may be available. One type of color image is a viewfinder image, and another type of color image is a scan texture. A scan texture may be a combination or blending of multiple different viewfinder images. Each intraoral scan may be associated with a corresponding viewfinder image generated at about the same time that the intraoral image was generated. If blended scans are used, then each scan texture may be based on a combination of viewfinder images that were associated with the raw scans used to produce a particular blended scan.

Another type of additional data may include an image generated under specific lighting conditions (e.g., an image generated under ultraviolet, near infrared or infrared lighting conditions). The additional data may be a 2D or 3D image, and may or may not include depth information (e.g., a height map).

The result of this training is a function that can predict dental classes directly from intraoral data (e.g., height maps of intraoral objects). In particular, the machine learning model(s) may be trained to generate a probability map, where each point in the probability map corresponds to a pixel of an input image and/or other input intraoral data and indicates one or more of a first probability that the pixel represents a first dental class, a second probability that the pixel represents a second dental class, a third probability that the pixel represents a third dental class, a fourth probability that the pixels represents a fourth dental class, a fifth probability that the pixel represents a fifth dental class, and so on.

From the dental diagnostics summary 103, a dentist may select any of the types of dental classes. For example, the dentist may select any one of tooth cracks 134, caries 120, gum recession 122, tooth wear 124, occlusion 126, crowding/spacing 128, plaque 130 and/or tooth stains 132. As discussed, multiple different types of dental conditions may be displayed, and for each type of dental condition a severity level for that dental condition may be shown. In the illustrated example, caries 120, tooth wear 124 and crowding/spacing 128 are shown to have issues found 155. Accordingly, as a result of performing a caries analysis, a tooth wear analysis and a crowding and/or spacing analysis, severity levels for tooth crowding and/or spacing 128, tooth wear 124 and caries 120 exceeded respective severity level thresholds. In the illustrated example, tooth stains 132 and occlusion 126 (e.g., poor occlusal contacts) are shown to have potential issues found 150, and tooth cracks 134, gum recession 122 and plaque 130 are shown to have no issues found 145.

A dentist, after a quick glance at the dental diagnostics summary 103, may determine that a patient has carries, clinically significant tooth wear, and crowding/spacing and/or other malocclusions 128. Accordingly, the dentist may select the caries 120 view option, the tooth wear 124 view option and/or the crowding/spacing 128 view option to quickly review the areas on the patient's dental arches at which caries, tooth wear and/or crowding (and/or spacing) were detected. The dentist may determine not to review gum recession, tooth cracks or plaque for the patient due to these dental conditions being classified as having no issues found. The dentist may or may not review the tooth stains and occlusion information due to these dental conditions having been classified as having potential issues found. Each of the illustrated dental conditions may be shown with an icon, button, link, or selectable option that a user can select via a graphical user interface of the dental diagnostics hub. Clicking on or otherwise selecting a particular dental condition may enable one or more tools associated with that specific dental condition.

The tools available to assess a selected dental condition may depend on the dental condition selected. For example, different assessment tools may be available for tooth stains 132 than for caries 120. In general, one of the available tools associated with a selected dental condition includes a simulation of a prognosis of the dental condition. Via the simulation, a doctor may determine what the area of interest (or areas of interest) exhibiting the dental condition looked like in the past and what they are predicted to look like in the future.

In embodiments, the dental diagnostics hub, and in particular the dental diagnostics summary 103, helps a doctor to quickly detect dental conditions and their respective severity levels, helps the doctor to make better judgments about treatment of dental conditions, and further helps the doctor in communicating with a patient that patient's dental conditions and possible treatments. This makes the process of identifying, diagnosing, and treating dental conditions easier and more efficient. The doctor may select any of the dental conditions to determine prognosis of that condition as it exists in the present and how it will likely progress into the future. Additionally, the dental diagnostics hub may provide treatment simulations of how the dental conditions will be affected or eliminated by one or more treatments.

In embodiments, a doctor may customize the dental conditions and/or areas of interest by adding emphasis or notes to specific dental conditions and/or areas of interest. For example, a patient may complain of a particular tooth aching. The doctor may highlight that particular tooth on the 3D model of the dental arches. Dental conditions that are found that are associated with the particular highlighted or selected tooth may then be shown in the dental diagnostics summary. In a further example, a doctor may select a particular tooth (e.g., lower left molar), and the dental diagnostics summary may be updated by modifying the severity results to be specific for that selected tooth. For example, if for the selected tooth an issue was found for caries and a possible issue was found for tooth stains, then the dental diagnostics summary 103 would be updated to show no issues found for tooth wear 124, occlusion 126, crowding/spacing 128, plaque 130, tooth cracks 134, and gum recession 122, to show a potential issue found for tooth stains 132 and to show an issue found for caries 120. This may help a doctor to quickly identify possible root causes for the pain that the patient complained of for the specific tooth that was selected. The doctor may then select a different tooth to get a summary of dental issues for that other tooth. Additionally, the doctor may select a dental arch, a quadrant of a dental arch, or a set of teeth, and the dental diagnostics summary 103 may be updated to show the dental conditions associated with the selected set of teeth, quadrant of a dental arch, and/or dental arch.

Figure 1D:
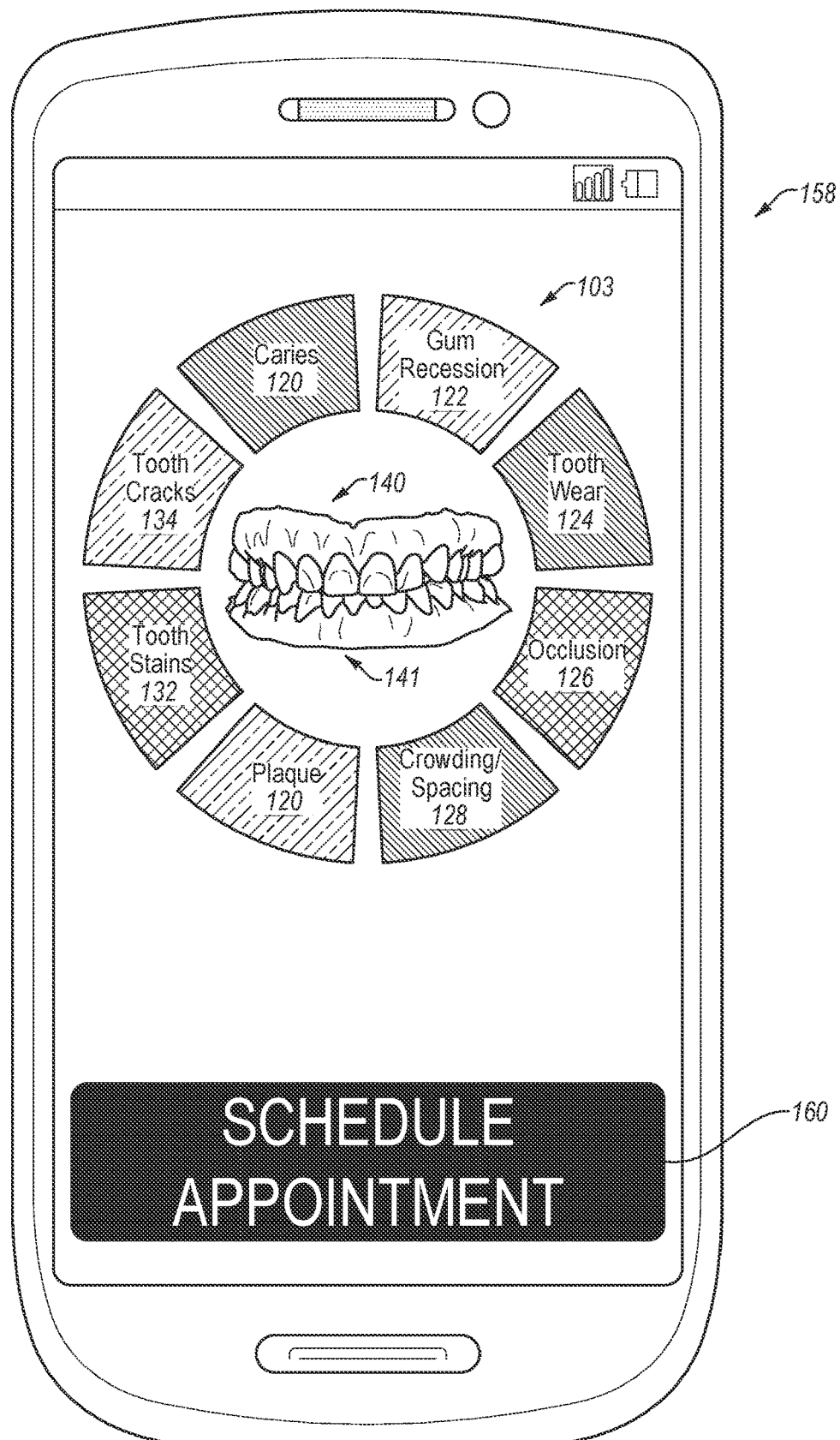
FIG. 1D illustrates a user interface for navigating diagnostics results provided to a mobile device by a dental diagnostics hub, in accordance with embodiments of the present disclosure.

FIG. 1D illustrates a user interface for navigating diagnostics results provided to a mobile device 158 by a dental diagnostics hub, in accordance with embodiments of the present disclosure. The dental diagnostics summary 103 generated by a dental diagnostics hub may be sent to a device of a patient, which may be a mobile device 158 or a traditionally stationary device. Examples of mobile devices include mobile phones, tablet computers, laptops, and so on. Examples of traditionally stationary devices include desktop computers, server computers, smart televisions, set top boxes, and so on. In embodiments, a link to the dental diagnostics summary 103 may be sent to the device of the patient, and the patient may activate the link (e.g., click on the link) to access the dental diagnostics summary 103. In embodiments, the underlying information that is summarized in the dental diagnostics summary 103 may also be accessible by the patient by selecting on one or more of the dental conditions in the dental diagnostics summary 103. This may show the patient which teeth exhibit specific dental conditions, for example. The patient's version of the dental diagnostics summary 103 may further include or be associated with a schedule appointment option or function 160. The patient may click on or otherwise select the schedule appointment option or function 160 to schedule an appointment. This may cause a mobile phone to call a dentist office for example, or may cause the patient's device to navigate to a calendar view showing available appointment times. The patient may click on or otherwise select an available appointment time to schedule an appointment with their dentist.

Figure 1E:
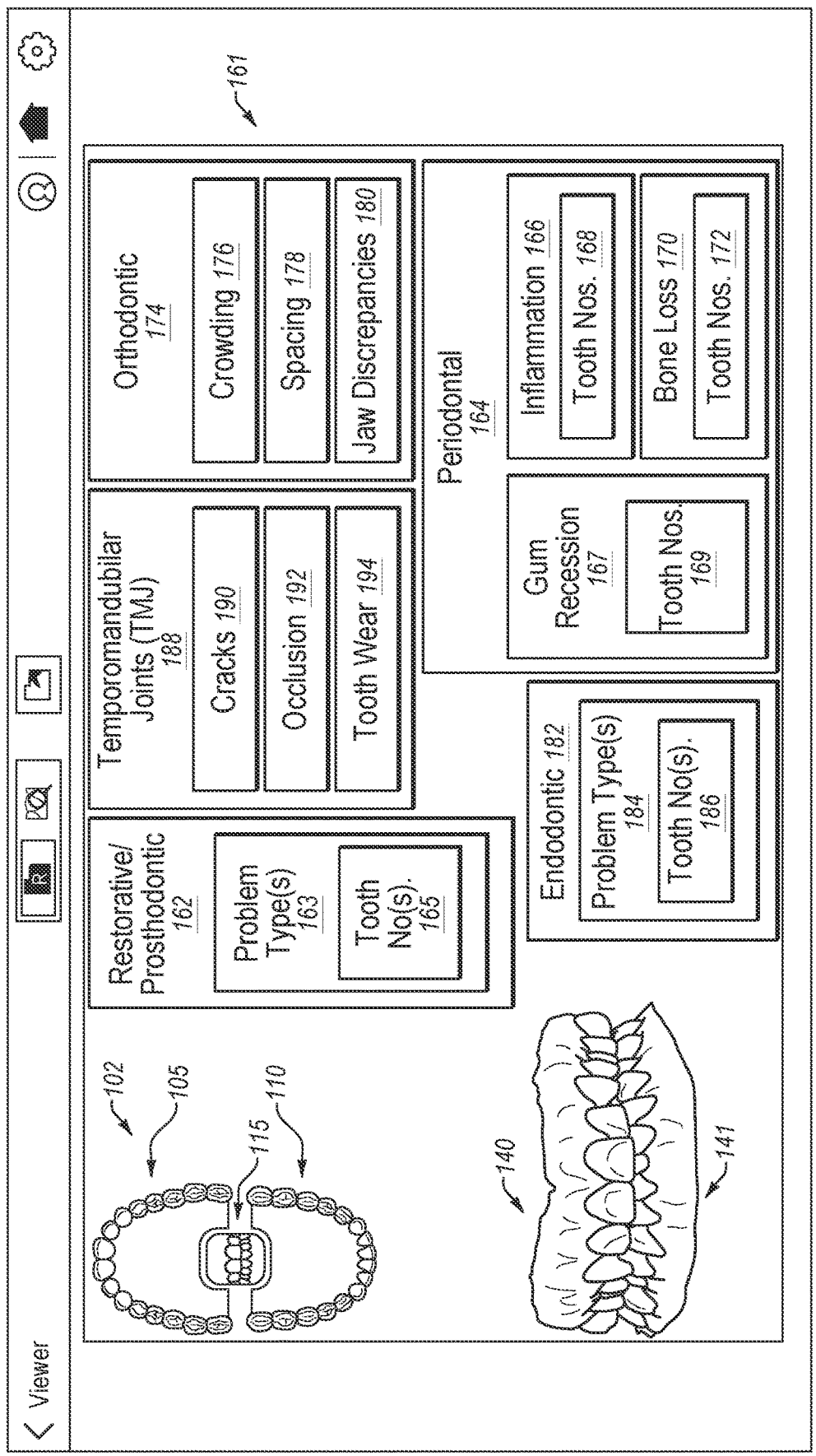
FIG. 1E illustrates a user interface of a dental diagnostics hub after diagnostics have been run on a patient's dental arches, in accordance with embodiments of the present disclosure.

FIG. 1E illustrates a user interface of a dental diagnostics hub showing a dental diagnostics summary 161 after diagnostics have been run on a patient's dental arches, in accordance with embodiments of the present disclosure. The dental diagnostics summary 161 presents dental information about a patient organized in a different manner than is shown in dental diagnostics summary 103. For dental diagnostics summary 103, summary information for many different types of dental conditions are shown together, without grouping the summary information based on dental categories. Dental diagnostics summary 161, on the other hand, groups dental conditions based on dental categories, and indicates specific types of dental conditions or problems within each of the dental categories. The dental condition information may also be arranged and presented in many other ways than the few examples shown herein.

In one embodiment, dental diagnostics summary 161 includes multiple high level dental categories or groups, including a restorative/prosthodontic category 162, a temporomandibular joints (TMJ) category 188, an orthodontic category 174, a periodontal category 164 and an endodontic category 182. All restorative and/or prosthodontic dental conditions may be displayed under restorative/prosthodontic category 162, all dental conditions associated with or caused by problems with TMJ may be displayed under TMJ category 188, all orthodontic dental conditions may be displayed under orthodontic category 174, all periodontal dental conditions may be displayed under periodontal category 164, and all endodontic dental conditions may be displayed under the endodontic category 182. Each of the high level dental categories may be coded (e.g., color coded) or otherwise include indicators to show whether or not dental conditions falling under those high level categories have been detected and/or severity levels of such dental conditions.

In embodiments, one or more of the high level dental categories (e.g., restorative/prosthodontic 162, temporomandibular joints (TMJ) 188, orthodontic 174, periodontal 164 and endodontic 182) include summary information for subcategories and/or particular dental conditions falling within the respective high level dental categories. In one embodiment, TMJ category 188 includes a cracks dental condition 190, an occlusion dental condition 192 and a tooth wear dental condition 194, which may correspond to tooth cracks 134, occlusion 126 and tooth wear 124, respectively, of FIG. 10. For each of the cracks dental condition 190, occlusion dental condition 192 and tooth wear dental condition 194, the dental diagnostics summary 161 may indicate whether teeth of the patient are affected by the respective dental condition, which teeth are affected by the respective dental condition and/or a severity of the respective dental condition. Each of dental conditions within the TMJ category 188 may be coded (e.g., color coded) or otherwise include indicators to show whether or not the respective dental conditions fa have been detected and/or severity levels of such dental conditions.

In one embodiment, orthodontic category 174 includes a crowding dental condition 176, a spacing dental condition 178 and a jaw discrepancies dental condition 180. Crowding dental condition 176 may correspond to crowding 128 of FIG. 10. Spacing dental condition 178 may provide information on gaps or spaces between teeth of a patient. Jaw discrepancies dental condition 180 may include information on problems with a patient's jaw, such as how the jaw closes, overbite, underbite, overjet, and so on. For each of the crowding dental condition 176, spacing dental condition 178 and jaw discrepancies dental condition 180, the dental diagnostics summary 161 may indicate whether teeth of the patient are affected by the respective dental condition, which teeth are affected by the respective dental condition and/or a severity of the respective dental condition. Each of dental conditions within the orthodontic category 188 may be coded (e.g., color coded) or otherwise include indicators to show whether or not the respective dental conditions have been detected and/or severity levels of such dental conditions. Selection of any of the spacing dental category 178, jaw discrepancies dental category 180 or crowding dental category 176 may launch a dental analysis tool illustrating the respective dental condition that was selected on the patient's dentition. From any of those dental analysis tools, an orthodontics tool may be launched, as discussed with reference to FIG. 5 below.

In one embodiment, periodontal category 164 includes an inflammation dental condition 166, a bone loss dental condition 170 and a gum recession dental condition 167. Gum swelling dental condition 167 may correspond to gum recession 122 of FIG. 10. Inflammation dental condition 166 may include information on gum swelling or inflammation for one or more teeth and/or a degree of swelling. Bone loss dental condition 170 may include information on bone density loss for one or more regions of a patient's jaw. For each of the gum recession dental condition 167, inflammation dental condition 166 and bone loss dental condition 170, the dental diagnostics summary 161 may indicate whether teeth of the patient are affected by the respective dental condition, which teeth are affected by the respective dental condition (e.g., tooth nos. 168, 169, 172) and/or a severity of the respective dental condition. Each of the dental conditions within the periodontal category 164 may be coded (e.g., color coded) or otherwise include indicators to show whether or not the respective dental conditions have been detected and/or severity levels of such dental conditions. Selection of any of the gum recession dental category 167, inflammation dental category 166 or bone loss dental category 170 may launch a dental analysis tool illustrating the respective dental condition that was selected on the patient's dentition.

In one embodiment, endodontic category 182 includes one or more types of endodontic problems. Endodontic problems may include problems relating to tooth roots and the soft tissues inside a tooth, such as dental pulp in a tooth. Endodontic category 182 may include endodontic conditions for one or more problem types 184, such as a first problem type for problems with dental pulp and a second problem type for problems with tooth roots. For each problem type 184, one or more affected tooth numbers 186 may be indicated. Each of dental conditions within the endodontic category 182 may be coded (e.g., color coded) or otherwise include indicators to show whether or not the respective dental conditions have been detected and/or severity levels of such dental conditions. Selection of any of the problem types 184 may launch a dental analysis tool illustrating the respective dental condition that was selected on the patient's dentition.

In one embodiment, restorative/prosthodontic category 162 includes one or more types of restorative and/or prosthodontic conditions. The term prosthodontic procedure refers, inter alia, to any procedure involving the oral cavity and directed to the design, manufacture or installation of a dental prosthesis at a dental site within the oral cavity, or a real or virtual model thereof, or directed to the design and preparation of the dental site to receive such a prosthesis. A prosthesis may include any restoration such as crowns, veneers, inlays, onlays, and bridges, for example, and any other artificial partial or complete denture. Prosthodontic dental conditions or issues may include a failing, failed or broken/cracked prosthesis, a worn prosthesis, a loose prosthesis, an ill-fitting prosthesis, and so on. Prosthodontic dental conditions may also include conditions that can be corrected by a prosthesis, such as a missing tooth, an edentulous dental arch, and so on. Restorative/prosthodontic category 162 may include conditions with existing prosthodontics, which may constitute a first problem type 163, and conditions that can be resolved using prosthodontics, which may constitute a second problem type 163. For each problem type 163, one or more affected tooth numbers 165 may be indicated. Each of the dental conditions within the restorative/prosthodontic category 162 may be coded (e.g., color coded) or otherwise include indicators to show whether or not the respective dental conditions have been detected and/or severity levels of such dental conditions. Selection of any of the problem types 163 may launch a dental analysis tool illustrating the respective dental condition that was selected on the patient's dentition.

In embodiments, the dental diagnostics summary 161 includes the scan segment selector 102 including upper dental arch segment selection 105, lower dental arch segment selection 110 and/or bite segment selection 115. In embodiments, the dental diagnostics summery 103 further includes views of the selected dental segments or modes (e.g., of the 3D model of the upper dental arch 140 and the 3D model of the lower dental arch 141 of the patient).

The dental diagnostics summary 161 provides a single view showing multiple different types of possible dental conditions at both a high level and at a lower level, and assessments as to the presence and/or severity of each of the types of dental conditions. In one embodiment, the various dental conditions are assigned one of three severity levels, including "no issues found", "potential issues found" and "issues found". Each of the dental conditions and/or dental categories (e.g., high level categories that may include multiple underlying conditions) may be coded or labeled with the severity ranking determined for that type of dental condition. In one embodiment, the dental conditions and/or categories are color coded to graphically show severity levels. For example, those dental conditions and/or categories for which issues were found may be coded red, those dental conditions and/or categories for which potential issues were found may be coded yellow, and those dental conditions and/or categories for which no issues were found may be coded green. Many other coding schemes are also possible. In one embodiment, each of the dental conditions and/or categories is assigned a numeric severity level. For example, on a scale of 1 to 100, each dental condition and/or category may be assigned a severity level between 1 and 100 to indicate the severity level of that dental condition. Those dental conditions and/or categories with a severity level that is below a first threshold severity level may be identified as dental conditions for which no issues were found. Those dental conditions and/or categories for which the severity level is above the first threshold severity level but below a second threshold severity level may be identified as dental conditions/categories for which potential issues were found. Those dental conditions and/or categories for which the severity level is above the second severity level threshold may be identified as dental conditions/categories for which issues were found.

Figure 2:
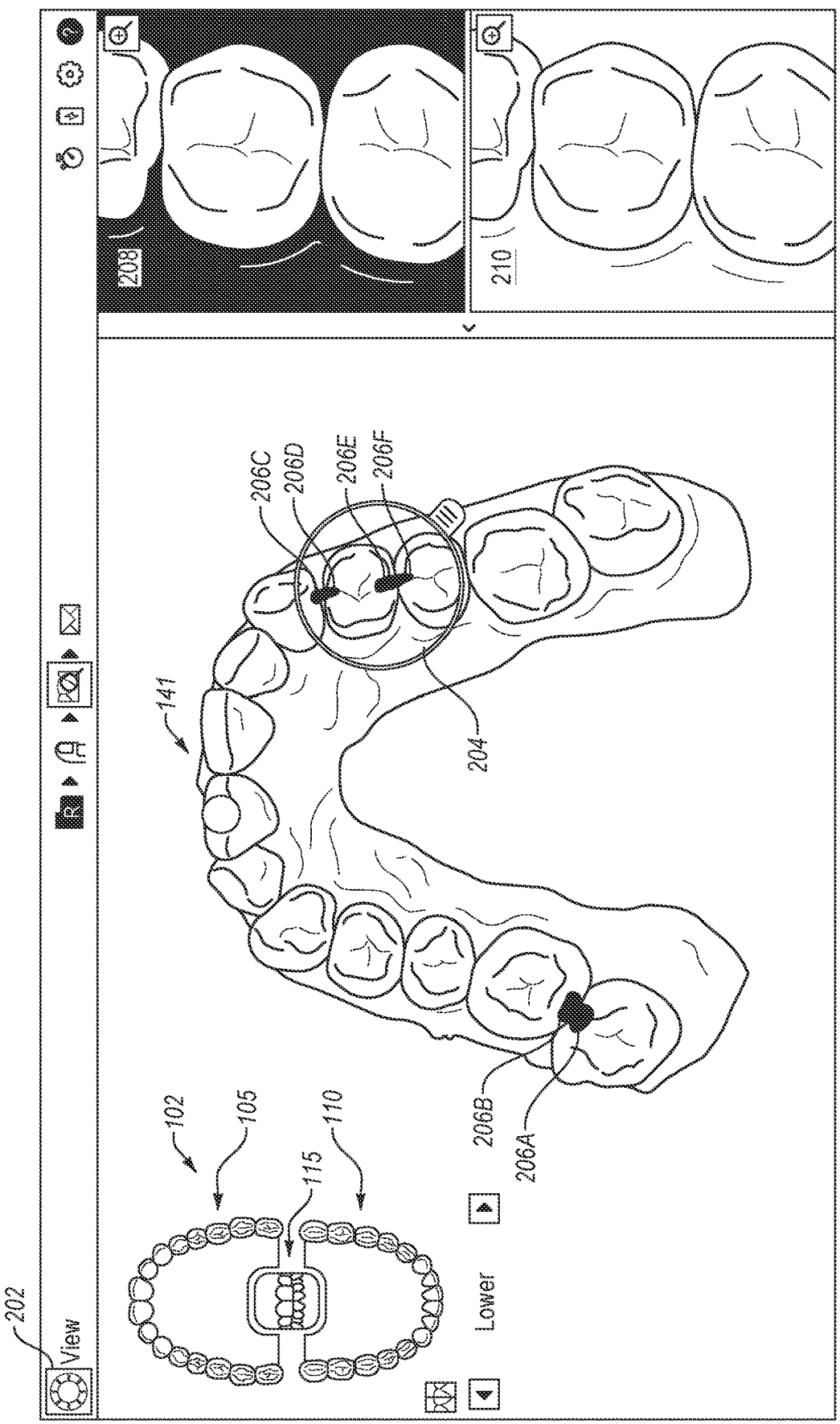
FIG. 2 illustrates a user interface for a caries analysis of a dental diagnostics hub, in accordance with embodiments of the present disclosure.

FIG. 2 illustrates a user interface for a caries analysis of a dental diagnostics hub, in accordance with embodiments of the present disclosure. The user interface for caries analysis may be provided responsive to a doctor selecting caries from the dental diagnostics summary 103. In embodiments, the caries analysis user interface includes the scan segment selector 102 including upper dental arch segment selection 105, lower dental arch segment selection 110 and/or bite segment selection 115. In some embodiments, each tooth that has an area of interest associated with the selected dental condition is highlighted or otherwise emphasized or marked in the scan segment selector 102. Accordingly, a quick glance at the scan segment selector 102 may show a doctor where to look further to review the AOIs with the selected dental condition. In some embodiments, individual teeth may be selected in the scan segment selector 102 to view just those selected teeth. For example, a doctor may select one or a few teeth having AOIs to show a 3D model with just those teeth.

In embodiments, the user interface for caries analysis further includes views of the selected dental segments or modes. In the illustrated example, a lower dental arch is selected, and the 3D model of the lower dental arch 141 of the patient is shown. An overlay of areas of interest (AOIs) that reflect detected caries is shown on the 3D model of the lower dental arch. For example, areas of interest 206A-F representing detected caries are shown on the 3D model of the lower dental arch 141. The upper dental arch segment may be selected to view AOIs representing caries in the upper dental arch. Additionally, both the upper and lower dental arch may be selected to show caries on both the upper and lower dental arches.

A doctor may change a view of the displayed 3D model or 3D models (e.g., of the 3D model of the lower dental arch 141) via the user interface so as to better view identified AOIs. Such changes to the view may include changing a zoom setting (e.g., by zooming in or out), rotating the 3D model(s), panning left, right, up, down, etc., and so on. A doctor may additionally use a focus tool to move a focus window 204 anywhere on the 3D model to focus in on a region of the 3D model of the dental arch(es). Additional information from one or more additional imaging modalities may be shown for a region that is within the focus window 204. For example, NIRI data for the region may be shown in a NIRI window 208, and color data for the region may be shown in a color window 210. For both the NIRI window 208 and the color window 210 the doctor may zoom in or out and/or change a view of the region.

The doctor may select a time-based simulation function to launch a time-based simulation for the selected dental condition (e.g., for caries). The time-based simulation may use information about AOIs as they existed at different points in time from the patient's record history (e.g., intraoral scans, NIRI images, color images, x-rays, etc. from different points in time) to project progression of the dental condition into the future and/or into the past. The time-based simulation may generate a video showing the start of the dental condition and progression of the dental condition over time to the present status of the dental condition and into the future. The time-based simulation may further include one or more treatment options, and may show what the areas of interest into the future after one or more selected treatments are performed.

The user interface for the caries analysis may indicate, for each of the detected caries 206A-F, a severity level of the caries. The severity level may be based on a size of the caries, on a location of the caries and/or on a distance between the caries and a patient's dentin and/or pulp.

In some embodiments, a secure share mode may be provided in which doctors can collaborate securely with other care providers and/or can communicate securely with patients (or parents of patients) via a remote connection.

A doctor may select a learn mode option (not shown) to bring up educational information on the difference between healthy teeth and teeth having caries, and the difference between different severity levels of caries. The patient's current dentition with currently detected caries may be shown, and further tooth decay may be projected. The educational information may show what happens when the tooth decay reaches the patient's dentin and/or pulp, indicating an amount of pain that the patient can expect at various stages of tooth decay. The educational information may be shown to a patient to show that patient the stages of tooth decay for their teeth and what will happen if they don't treat the tooth decay.

Once the doctor is done reviewing the caries information for the patient, the doctor may select a dental diagnostics summary view icon or navigation option 202 to navigate back to the dental diagnostic summary 103.

Figure 3:
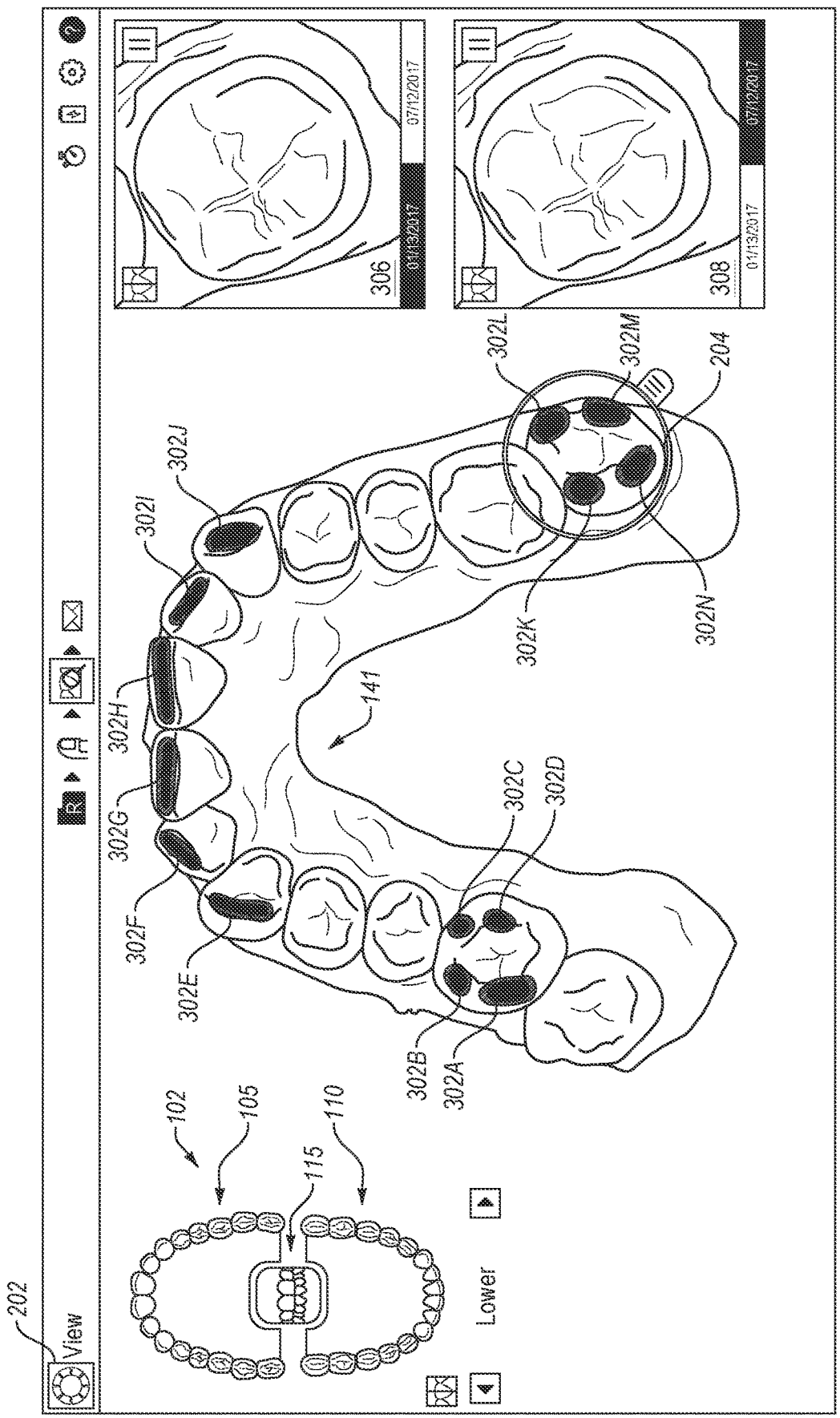
FIG. 3 illustrates a user interface for a tooth wear analysis of a dental diagnostics hub, in accordance with embodiments of the present disclosure.

FIG. 3 illustrates a user interface for a tooth wear analysis of a dental diagnostics hub, in accordance with embodiments of the present disclosure. The user interface for tooth wear analysis may be provided responsive to a doctor selecting tooth wear from the dental diagnostics summary 103. In embodiments, the tooth wear analysis user interface includes the scan segment selector 102 including upper dental arch segment selection 105, lower dental arch segment selection 110 and/or bite segment selection 115. In some embodiments, each tooth that has an area of interest associated with the selected dental condition is highlighted or otherwise emphasized or marked in the scan segment selector 102. Accordingly, a quick glance at the scan segment selector 102 may show a doctor where to look further to review the AOIs with the selected dental condition. In some embodiments, individual teeth may be selected in the scan segment selector 102 to view just those selected teeth. For example, a doctor may select one or a few teeth having AOIs to show a 3D model with just those teeth.

In embodiments, the user interface for tooth wear analysis further includes views of the selected dental segments or modes. In the illustrated example, a lower dental arch is selected, and the 3D model of the lower dental arch 141 of the patient is shown. An overlay of areas of interest (AOIs) that reflect detected tooth wear is shown on the 3D model of the lower dental arch. For example, areas of interest 302A-N representing detected regions of tooth wear are shown on the 3D model of the lower dental arch 141. The upper dental arch segment may be selected to view AOIs representing tooth wear in the upper dental arch. Additionally, both the upper and lower dental arch may be selected to show tooth wear on both the upper and lower dental arches.

A doctor may change a view of the displayed 3D model or 3D models (e.g., of the 3D model of the lower dental arch 141) via the user interface so as to better view identified AOIs. Such changes to the view may include changing a zoom setting (e.g., by zooming in or out), rotating the 3D model(s), panning left, right, up, down, etc., and so on. A doctor may additionally use a focus tool to move a focus window 204 anywhere on the 3D model to focus in on a region of the 3D model of the dental arch(es). Additional information from one or more additional imaging modalities may be shown for a region that is within the focus window 404. For example, a 3D surface of the region within the focus window 204 may be shown for a first time period in a first point-in-time snapshot window 306 and for a second time period in a second point-in-time snapshot window 308. For each of the point-in-time snapshot windows 306, 308, a doctor may select a specific point-in-time snapshot to view. The point-in-time snapshots may show scanned surfaces for points-in-time at which scans were performed and/or may show interpolated or extrapolated surfaces for points-in-time at which no scans were performed. For each of the point-in-time snapshot windows, a doctor may press a play or pause icon or button to show a progression of the 3D surfaces from the current selected point-of-time into the future and/or into the past.

The doctor may select the time-based simulation function to launch a time-based simulation for the selected dental condition (e.g., for tooth wear). The time-based simulation may use information about AOIs as they existed at different points in time from the patient's record history (e.g., intraoral scans, NIRI images, color images, x-rays, etc. from different points in time) to project progression of the dental condition into the future and/or into the past. The time-based simulation may generate a video showing the start of the dental condition and progression of the dental condition over time to the present status of the dental condition and into the future. The time-based simulation may further include one or more treatment options, and may show what the areas of interest into the future after one or more selected treatments are performed.

Once the doctor is done reviewing the tooth wear information for the patient, the doctor may select the dental diagnostics summary view icon or navigation option 202 to navigate back to the dental diagnostic summary 103.

No user interfaces are shown for gum swelling, plaque, tooth cracks or gum recession. However, similar views for gum swelling, plaque, tooth cracks and/or gum recession may be shown to a dentist as are shown with regards to caries and tooth wear. Additionally, similar dental condition analysis tools may be provided for gum swelling, plaque, tooth cracks and/or gum recession as are provided for caries and/or tooth wear. A gum swelling analysis tool, for example, may project an amount of gum swelling into the future, and show inflammation of the gums, gum bleeding, and so on. Similarly, a gum recession analysis tool may project an amount of gum recession into the future, showing exposed portions of tooth roots, and so on.

Figure 4:
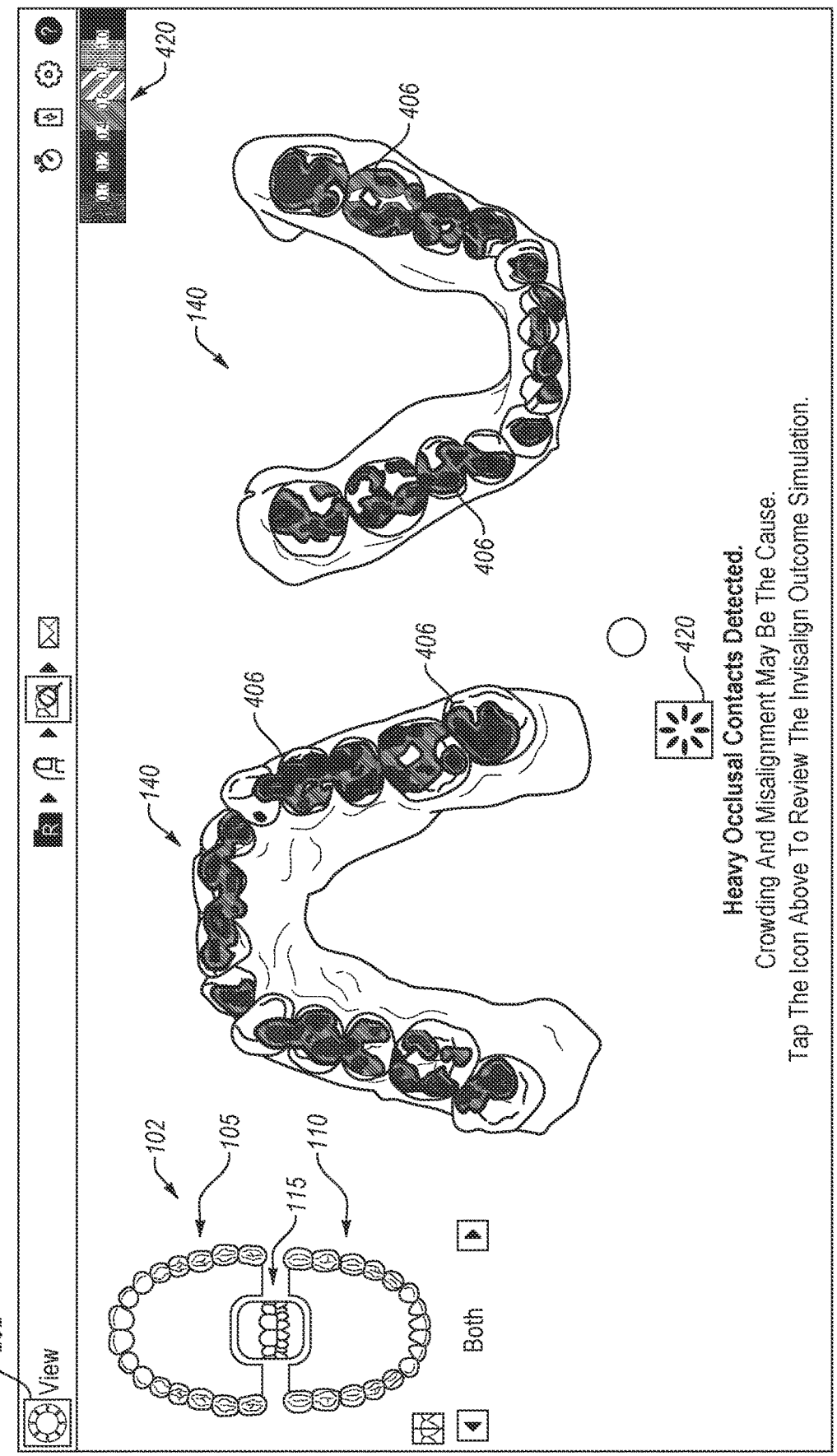
FIG. 4 illustrates a user interface for an occlusal contact analysis of a dental diagnostics hub, in accordance with embodiments of the present disclosure.

FIG. 4 illustrates a user interface for an occlusal contact analysis of a dental diagnostics hub, in accordance with embodiments of the present disclosure. The user interface for occlusal contact analysis may be provided responsive to a doctor selecting occlusal contacts from the dental diagnostics summary 103. In embodiments, the occlusal contact analysis user interface includes the scan segment selector 102 including upper dental arch segment selection 105, lower dental arch segment selection 110 and/or bite segment selection 115. In some embodiments, each tooth that has an area of interest associated with the selected dental condition is highlighted or otherwise emphasized or marked in the scan segment selector 102. Areas of interest for occlusal contacts may be tooth regions for which heavy occlusal contacts are identified, for example. Accordingly, a quick glance at the scan segment selector 102 may show a doctor where to look further to review the AOIs with the selected dental condition. In some embodiments, individual teeth may be selected in the scan segment selector 102 to view just those selected teeth. For example, a doctor may select one or a few teeth having AOIs to show a 3D model with just those teeth.

In embodiments, the user interface for occlusal contact analysis further includes views of the selected dental segments or modes. In the illustrated example, both an upper dental arch segment and a lower dental arch are selected, and the 3D models of the lower dental arch 141 and of the upper dental arch 140 of the patient are shown. An overlay of areas of interest (AOIs) 406 that reflect detected occlusal contact is shown on the 3D models of the lower dental arch 141 and of the upper dental arch 140. The occlusal contact overlay 406 may be coded in some way (e.g., color coded) to show the severity or amount of occlusal contact for one or more regions of the teeth on the dental arches. The coding may indicate a distance from 0 to 1, where 0 represents full contact with the opposing dental arch (e.g., in which the AOI is in contact for multiple different relative positions of the upper and lower jaws) and 1 represents full separation from the opposing dental arch (e.g., in which the AOI is not in contact for any of the multiple different relative positions of the upper and lower jaws). A legend 420 for the coding may be shown in the user interface, showing different colors or other graphical indicators for each of the occlusal contact ratings.

The user interface for the occlusal contact analysis may include information on possible underlying causes of problematic occlusal contacts, such as crowding and misalignment of teeth. From the user interface for the occlusal contact analysis, the doctor may select an orthodontic treatment 420 icon or button to launch an orthodontic treatment simulator and/or orthodontic treatment plan generator.

A doctor may change a view of the displayed 3D model or 3D models (e.g., of the 3D model of the lower dental arch 141 and upper dental arch 140) via the user interface so as to better view identified AOIs. Such changes to the view may include changing a zoom setting (e.g., by zooming in or out), rotating the 3D model(s), panning left, right, up, down, etc., and so on.

The doctor may select the time-based simulation function to launch a time-based simulation for the selected dental condition (e.g., for occlusal contacts). The time-based simulation may use information about AOIs as they existed at different points in time from the patient's record history (e.g., intraoral scans, NIRI images, color images, x-rays, etc. from different points in time) to project progression of the dental condition into the future and/or into the past. The time-based simulation may generate a video showing the start of the dental condition and progression of the dental condition over time to the present status of the dental condition and into the future. The time-based simulation may further include one or more treatment options, and may show what the areas of interest into the future after one or more selected treatments are performed.

Once the doctor is done reviewing the occlusal contact information for the patient, the doctor may select the dental diagnostics summary view icon or navigation option 202 to navigate back to the dental diagnostic summary 103.

Figure 5A:
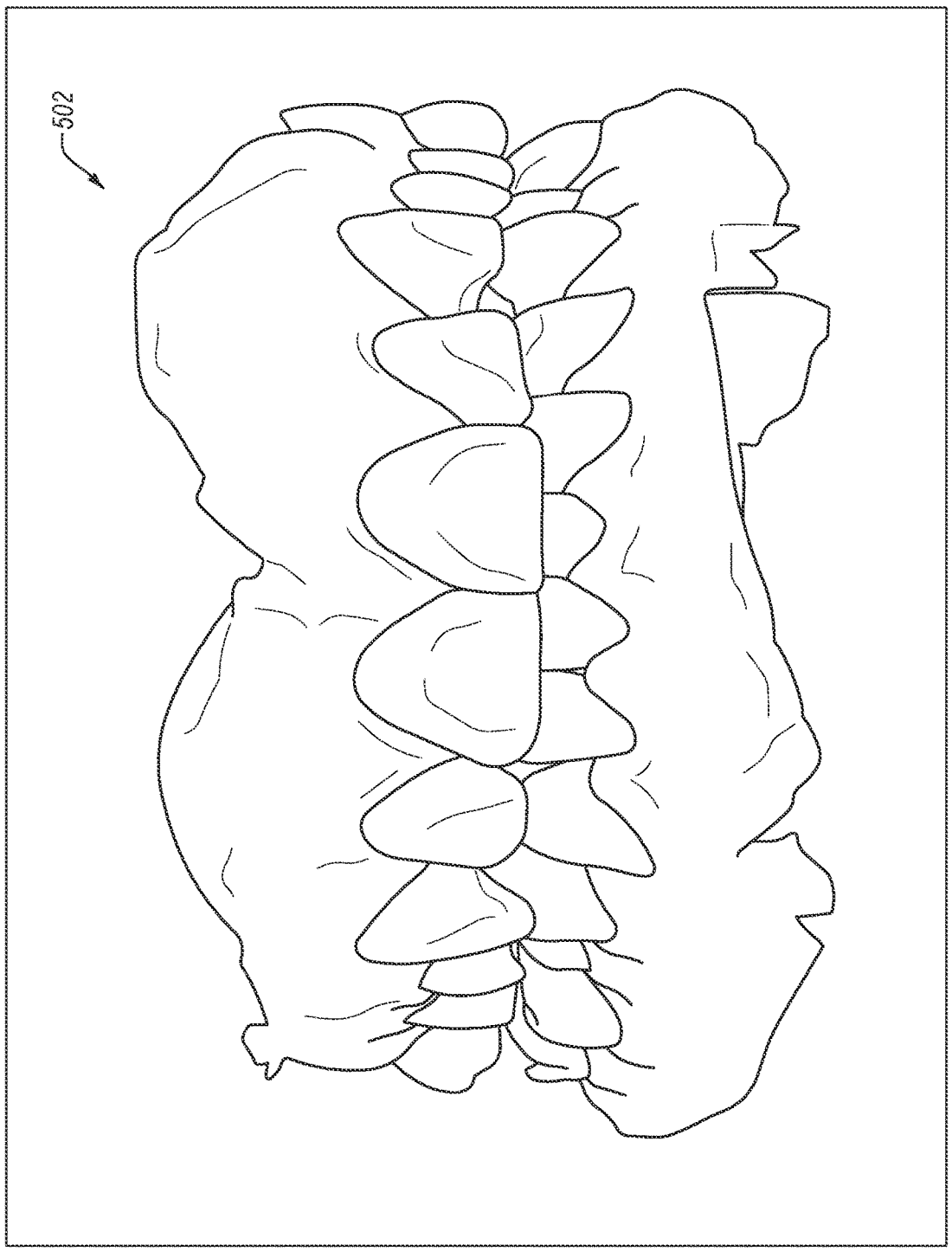
FIG. 5A illustrates a user interface for a malocclusion analysis of a dental diagnostics hub, in accordance with embodiments of the present disclosure.

FIG. 5A illustrates a user interface for malocclusion analysis of a dental diagnostics hub, in accordance with embodiments of the present disclosure. The user interface for malocclusion analysis may be provided responsive to a doctor selecting crowding from the dental diagnostics summary 103. In embodiments, the malocclusion analysis user interface includes the scan segment selector 102 including upper dental arch segment selection 105, lower dental arch segment selection 110 and/or bite segment selection 115. In some embodiments, each tooth that has an area of interest associated with the selected dental condition is highlighted or otherwise emphasized or marked in the scan segment selector 102. Areas of interest for occlusal contacts may be tooth regions for which heavy occlusal contacts are identified, for example. Accordingly, a quick glance at the scan segment selector 102 may show a doctor where to look further to review the AOIs with the selected dental condition. In some embodiments, individual teeth may be selected in the scan segment selector 102 to view just those selected teeth. For example, a doctor may select one or a few teeth having AOIs to show a 3D model with just those teeth.

AOIs showing tooth crowding 501 may be shown on the 3D models of the upper dental arch 140 and/or lower dental arch 141.

From the user interface for the malocclusion analysis, the doctor may select an orthodontic treatment 420 icon or button to launch an orthodontic treatment simulator and/or orthodontic treatment plan generator.

A doctor may change a view of the displayed 3D model or 3D models (e.g., of the 3D model of the lower dental arch 141 and upper dental arch 140) via the user interface so as to better view identified AOIs. Such changes to the view may include changing a zoom setting (e.g., by zooming in or out), rotating the 3D model(s), panning left, right, up, down, etc., and so on.

The doctor may select the time-based simulation function to launch a time-based simulation for the selected dental condition (e.g., for malocclusion).

Once the doctor is done reviewing the malocclusion information for the patient, the doctor may select the dental diagnostics summary view icon or navigation option 202 to navigate back to the dental diagnostic summary 103.

Figure 5B:
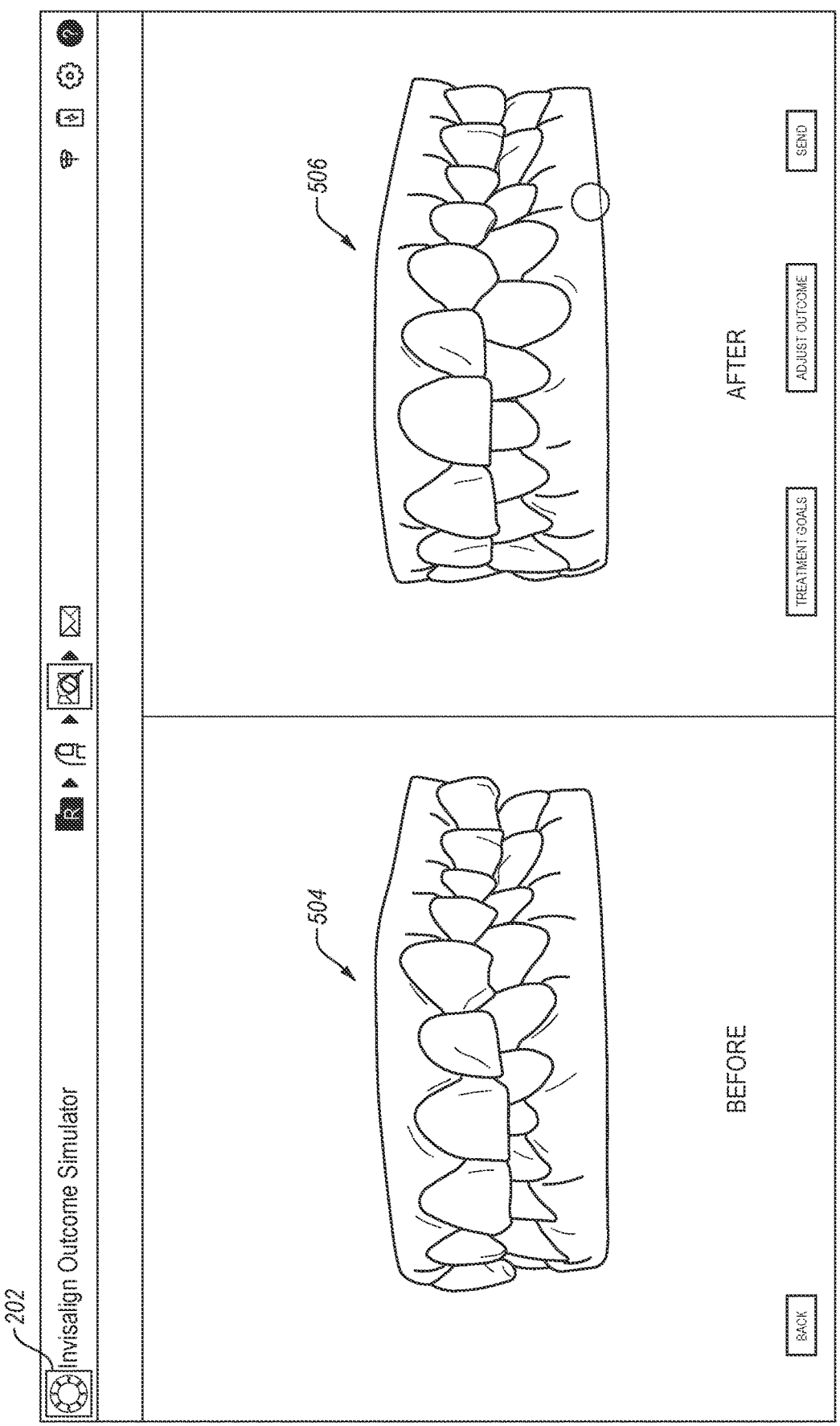
FIG. 5B illustrates pre-treatment and post-treatment models of a dental arch in a user interface for an orthodontic treatment analysis of a dental diagnostics hub, in accordance with embodiments of the present disclosure.

FIG. 5B illustrates an orthodontic treatment simulator user interface showing pre-treatment and post-treatment models of a dental arch, in accordance with embodiments of the present disclosure. The orthodontic treatment simulator may be launched responsive to a doctor selecting an orthodontic treatment 420 icon or button, such as from the user interface for malocclusion analysis and/or the user interface for occlusal contact analysis.

The orthodontic treatment simulator may determine a movement path to move one or more teeth from an initial arrangement of teeth 504 as determined from 3D models of a patient's current dental arches to a target arrangement of teeth 506 for the patient's dental arches. The target arrangement of the teeth (e.g., a desired and intended end result of orthodontic treatment) can be received from a clinician in the form of a prescription, can be calculated from basic orthodontic principles, and/or can be extrapolated computationally from a clinical prescription. In embodiments, a target arrangement for the patient's teeth is automatically determined based on aesthetic principles and/or ideal occlusion principles.

A doctor may adjust treatment goals via option 510, which may cause the target arrangement of the teeth 506 to change. Additionally, the doctor may directly or manually adjust the simulated treatment outcome via option 515.

With a specification of the desired final positions of the teeth and a digital representation of the teeth themselves, the final position and surface geometry of each tooth can be specified to form a complete model of the tooth arrangement at the desired end of treatment.

Having both an initial position and a target position for each tooth, a movement path can be defined for the motion of each tooth. In some embodiments, the movement paths are configured to move the teeth in the quickest fashion with the least amount of round-tripping to bring the teeth from their initial positions to their desired target positions. The tooth paths can optionally be segmented, and the segments can be calculated so that each tooth's motion within a segment stays within threshold limits of linear and rotational translation. In this way, the end points of each path segment can constitute a clinically viable repositioning, and the aggregate of segment end points can constitute a clinically viable sequence of tooth positions, so that moving from one point to the next in the sequence does not result in a collision of teeth.

A force system to produce movement of the one or more teeth along the movement path may be determined. A force system can include one or more forces and/or one or more torques. Different force systems can result in different types of tooth movement, such as tipping, translation, rotation, extrusion, intrusion, root movement, etc. Biomechanical principles, modeling techniques, force calculation/measurement techniques, and the like, including knowledge and approaches commonly used in orthodontia, may be used to determine the appropriate force system to be applied to the tooth to accomplish the tooth movement. In determining the force system to be applied, sources may be considered including literature, force systems determined by experimentation or virtual modeling, computer-based modeling, clinical experience, minimization of unwanted forces, etc.

The initial arrangement of teeth 504 and/or target arrangement of teeth 506 for the patient's dental arches may be sent to a patient for their review via option 520. A doctor may navigate back to a previous interface, such as to the malocclusion analysis user interface or to the user interface for occlusal contact analysis, via the back option 525. Additionally, once the doctor is done reviewing the simulated orthodontic treatment results, the doctor may select the dental diagnostics summary view icon or navigation option 202 to navigate back to the dental diagnostic summary 103.

Figure 6A:
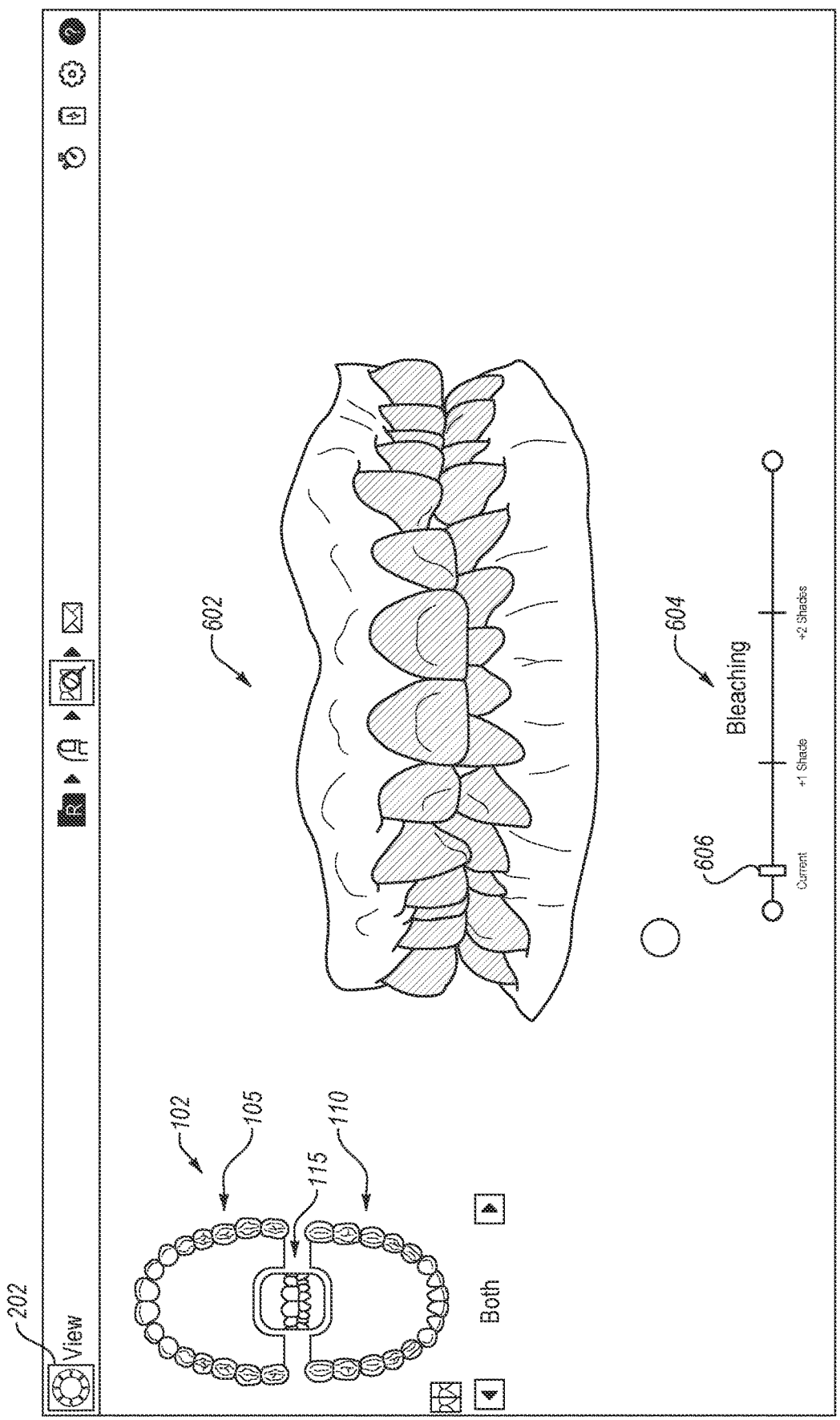
FIG. 6A illustrates a user interface for a tooth stain analysis of a dental diagnostics hub, in accordance with embodiments of the present disclosure.
Figure 6B:
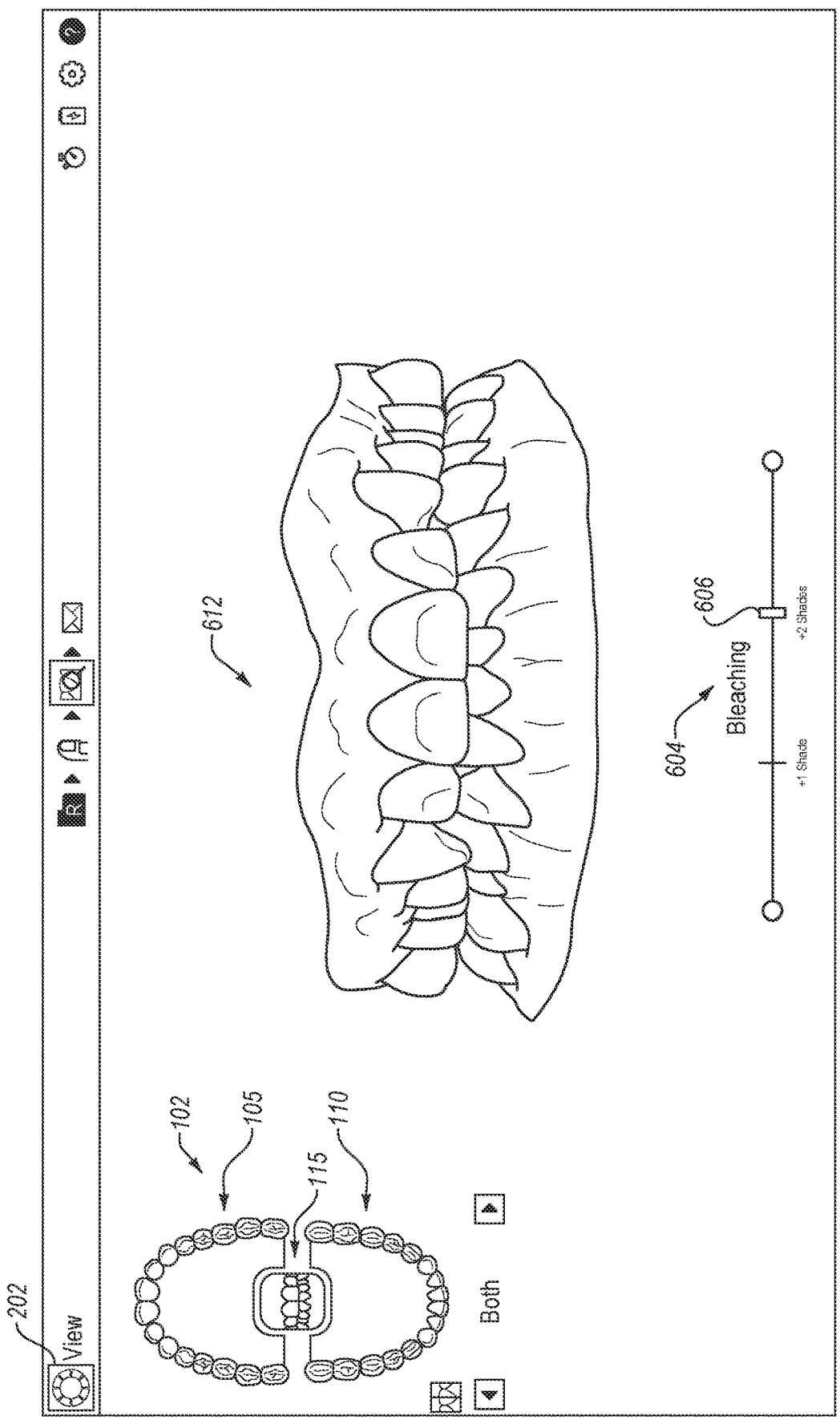
FIG. 6B illustrates a user interface for a post-bleaching tooth stain analysis of a dental diagnostics hub, in accordance with embodiments of the present disclosure.

FIGS. 6A-B illustrate a user interface for a tooth stain analysis of a dental diagnostics hub, in accordance with embodiments of the present disclosure. The user interface for tooth stains analysis may be provided responsive to a doctor selecting tooth stains from the dental diagnostics summary 103. In embodiments, the tooth stains analysis user interface includes the scan segment selector 102 including upper dental arch segment selection 105, lower dental arch segment selection 110 and/or bite segment selection 115.

In embodiments, the user interface for tooth stains analysis further includes views of the selected dental segments or modes. In the illustrated example, both an upper dental arch segment and a lower dental arch are selected, and the 3D models of the lower dental arch 141 and of the upper dental arch 140 of the patient are shown. The 3D models of the upper dental arch 140 and/or lower dental arch 141 are shown with accurate color information showing the current color of the patient's teeth (which may include staining).

The user interface for the tooth staining analysis includes a tooth bleaching selector 604, which may be a slide bar in embodiments. In FIG. 6A, the tooth bleaching selector 604 indicates a current shade indicator 606 for the teeth. The current shade indicator 606 shows the current tooth shade on a tooth shade spectrum. As shown, the tooth shade indicator 606 shows that the patient's teeth are significantly stained. The doctor may adjust the current shade indicator 606 to one or more different tooth shades. In response to the current shade indicator 606 being adjusted along the tooth bleaching slide bar, processing logic determines updated color information for the teeth, and displays the teeth with the updated color information. FIG. 6B illustrates the user interface for the tooth stain analysis showing updated shading of the patient's teeth after the doctor has moved the tooth shade indicator 606 to +2 shades.

A doctor may change a view of the displayed 3D model or 3D models (e.g., of the 3D model of the lower dental arch 141 and upper dental arch 140) via the user interface so as to better view identified AOIs. Such changes to the view may include changing a zoom setting (e.g., by zooming in or out), rotating the 3D model(s), panning left, right, up, down, etc., and so on.

The doctor may select the time-based simulation function to launch a time-based simulation for the selected dental condition (e.g., for tooth staining). The time-based simulation may use information about AOIs as they existed at different points in time from the patient's record history (e.g., intraoral scans, NIRI images, color images, x-rays, etc. from different points in time) to project progression of the dental condition into the future and/or into the past. The time-based simulation may generate a video showing the start of the dental condition and progression of the dental condition over time to the present status of the dental condition and into the future. The time-based simulation may further include one or more treatment options, and may show what the areas of interest into the future after one or more selected treatments are performed.

Once the doctor is done reviewing the occlusal contact information for the patient, the doctor may select the dental diagnostics summary view icon or navigation option 202 to navigate back to the dental diagnostic summary 103.

Figure 7:
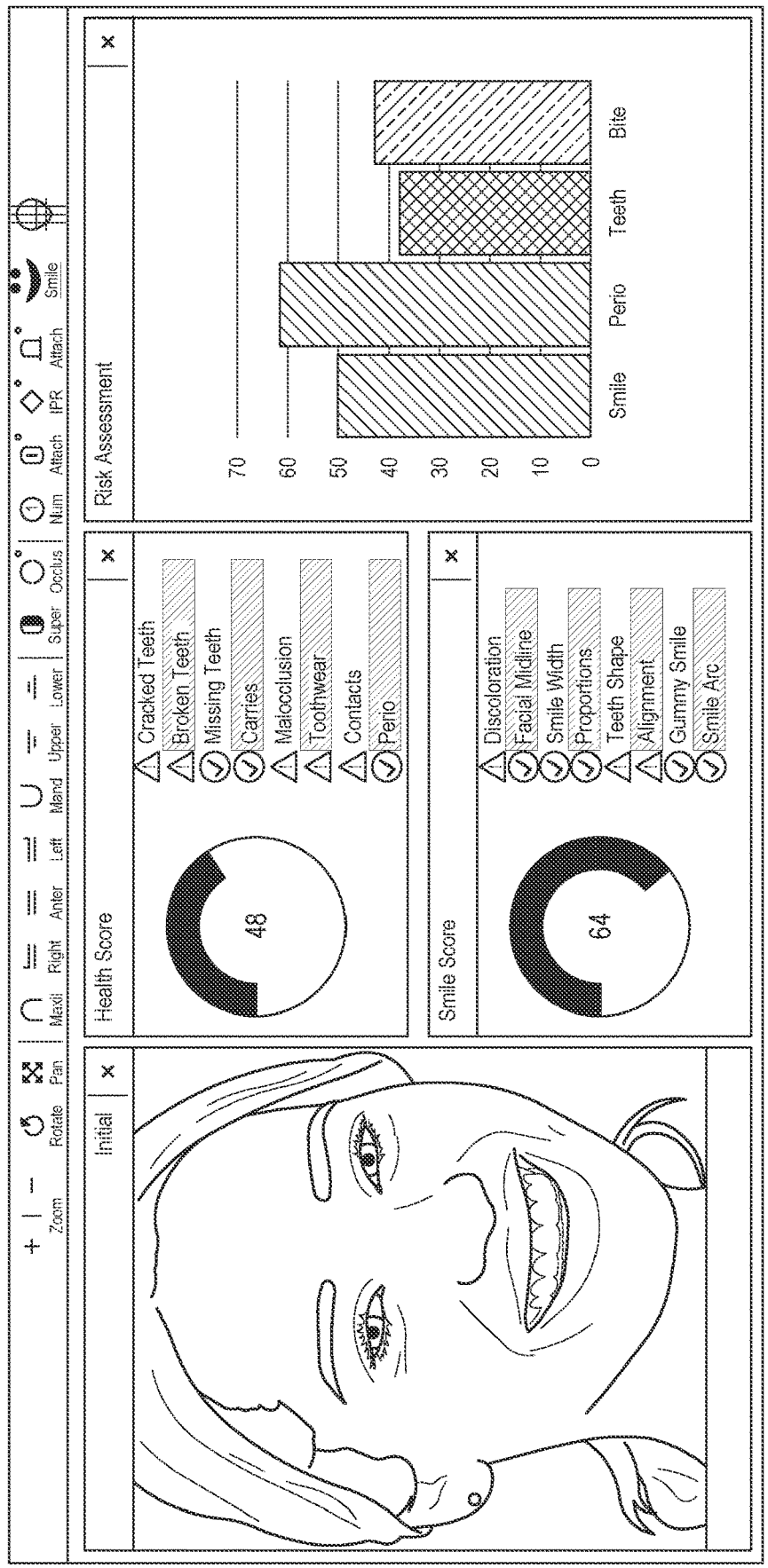
FIG. 7 illustrates a patient dental score card of a dental diagnostics hub, in accordance with embodiments of the present disclosure.

FIG. 7 illustrates a patient dental score card 700 of a dental diagnostics hub, in accordance with embodiments of the present disclosure. The patient dental score card 700 may include an image of the patient's smile 702, a dental health score 704, a dental smile score 706 and a dental risk assessment 708. The dental health score 704 may be based on a result of the multiple dental condition analyses performed by the dental diagnostics hub, and may be a global score reflective of patient dental health based on a combination of the various types of identified dental conditions and the severity levels of the identified dental conditions. For example, the dental health score 704 may be based on one or more of an assessment of cracked teeth, broken teeth, missing teeth, caries, malocclusion, tooth wear, occlusal contacts, periodontal issues, and so on. Selection of the dental health score 704 may cause the dental diagnostics hub to navigate to the dental diagnostic summary 103 in embodiments. The smile score 706 may be based on one or more of an assessment of tooth staining or discoloration, a facial midline, smile width, dental and/or facial proportions, tooth shape, tooth alignment, amount of gums that show in smile and/or an arc of the smile. The risk assessment may show a smile score (associated with tooth staining and so on), a periodontal score associated with gum recession and/or gum swelling), a teeth score (associated with tooth cracks, tooth breaks, missing teeth and/or caries) and a bite score (associated with occlusal contacts).

Figure 8:
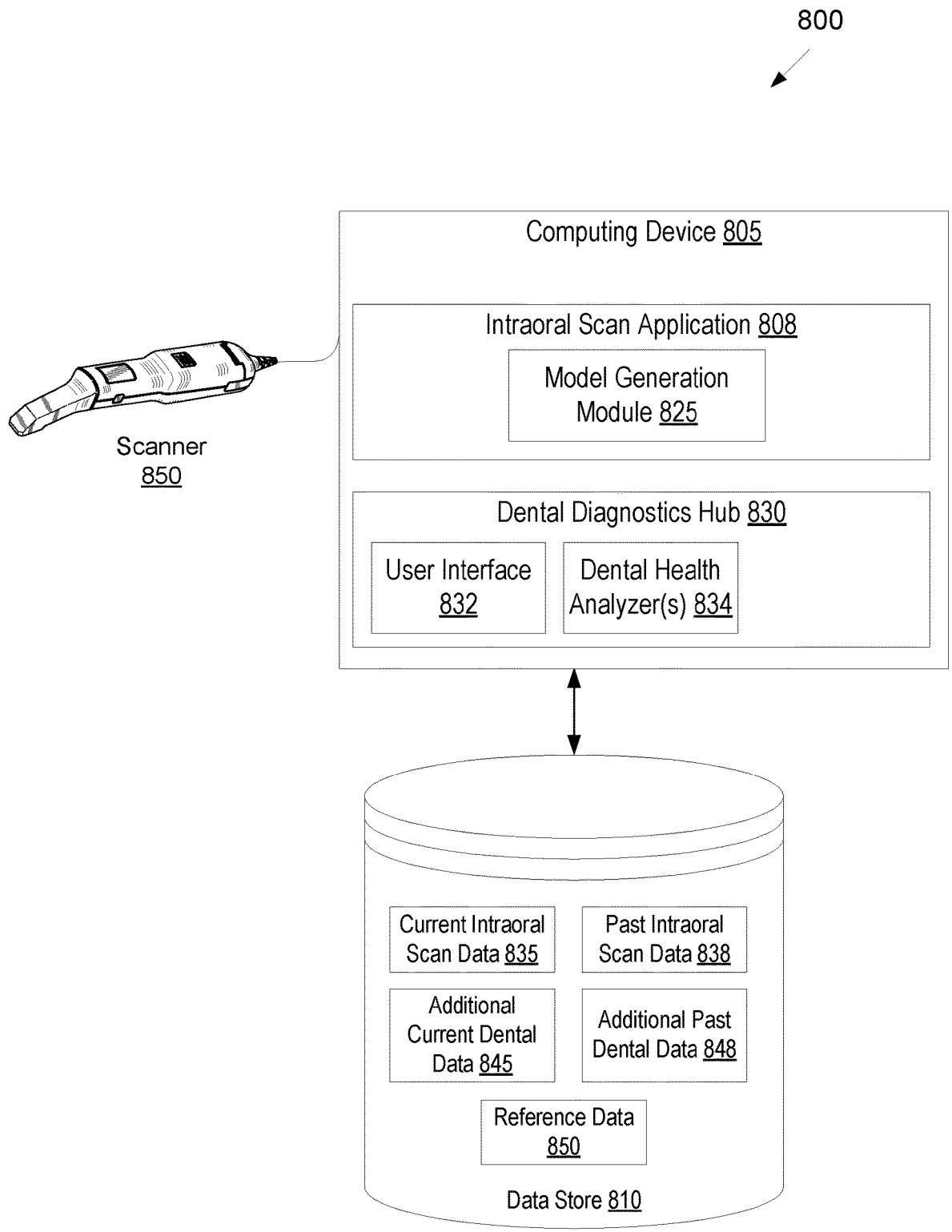
FIG. 8 illustrates an intraoral scanning system, in accordance with embodiments of the present disclosure.

FIG. 8 illustrates one embodiment of a system 800 for performing intraoral scanning, generating a virtual three dimensional model of a dental site and/or performing dental diagnostics. In one embodiment, system 800 carries out one or more operations of below described with reference to FIGS. 1A-7 and 9A-12. System 800 includes a computing device 805 that may be coupled to a scanner 850 and/or a data store 810.

Computing device 805 may include a processing device, memory, secondary storage, one or more input devices (e.g., such as a keyboard, mouse, tablet, and so on), one or more output devices (e.g., a display, a printer, etc.), and/or other hardware components. Computing device 805 may be connected to a data store 810 either directly or via a network. The network may be a local area network (LAN), a public wide area network (WAN) (e.g., the Internet), a private WAN (e.g., an intranet), or a combination thereof. The computing device 805 may be integrated into the scanner 850 in some embodiments to improve performance and mobility.

Data store 810 may be an internal data store, or an external data store that is connected to computing device 805 directly or via a network. Examples of network data stores include a storage area network (SAN), a network attached storage (NAS), and a storage service provided by a cloud computing service provider. Data store 810 may include a file system, a database, or other data storage arrangement.

In some embodiments, a scanner 850 for obtaining three-dimensional (3D) data of a dental site in a patient's oral cavity is operatively connected to the computing device 805. Scanner 850 may include a probe (e.g., a hand held probe) for optically capturing three dimensional structures (e.g., by confocal focusing of an array of light beams). One example of such a scanner 850 is the iTero® intraoral digital scanner manufactured by Align Technology, Inc. Other examples of intraoral scanners include the 8M™ True Definition Scanner and the Apollo DI intraoral scanner and CEREC AC intraoral scanner manufactured by Sirona®.

The scanner 850 may be used to perform an intraoral scan of a patient's oral cavity. An intraoral scan application 808 running on computing device 805 may communicate with the scanner 850 to effectuate the intraoral scanning. A result of the intraoral scanning may be a sequence of intraoral images or scans that have been generated. Each intraoral scan may include x, y and z position information for one or more points on a surface of a scanned object. In one embodiment, each intraoral scan includes a height map of a surface of a scanned object. An operator may start a scanning operation with the scanner 850 at a first position in the oral cavity, move the scanner 850 within the oral cavity to a second position while the scanning is being performed, and then stop recording of intraoral scans. In some embodiments, recording may start automatically as the scanner identifies either teeth. The scanner 850 may transmit the intraoral scans to the computing device 805. Computing device 805 may store the current intraoral scan data 835 from a current scanning session in data store 810. Data store 810 may additionally include past intraoral scan data 838, additional current dental data 845 generated during a current patient visit (e.g., x-ray images, CBCT scan data, panoramic x-ray images, ultrasound data, color photos, and so on), additional past dental data generated during one or more prior patient visits (e.g., x-ray images, CBCT scan data, panoramic x-ray images, ultrasound data, color photos, and so on), and/or reference data 850. Alternatively, scanner 850 may be connected to another system that stores data in data store 810. In such an embodiment, scanner 850 may not be connected to computing device 805.

According to an example, a user (e.g., a practitioner) may subject a patient to intraoral scanning. In doing so, the user may apply scanner 850 to one or more patient intraoral locations. The scanning may be divided into one or more segments (e.g., upper dental arch, lower dental arch, and bite). Via such scanner application, the scanner 850 may provide the current intraoral scan data 835 to computing device 805. The current and/or past intraoral scan data 835, 838 may include 3D surface data (e.g., in the form of 3D images or images with height information), 2D or 3D color image data, NIRI image data, ultraviolet image data, and so on. Such scan data may be provided from the scanner to the computing device 805 in the form of one or more points (e.g., one or more pixels and/or groups of pixels). For instance, the scanner 850 may provide a 3D image as one or more point clouds.

In one embodiment, intraoral scan application 808 includes a model generation module 825. When a scan session is complete (e.g., all images for a dental site have been captured), model generation module 825 may generate a virtual 3D model of the scanned dental site. To generate the virtual model, model generation module 825 may register and "stitch" together the intraoral scans generated from the intraoral scanning session. In one embodiment, performing registration includes capturing 3D data of various points of a surface in multiple scans (views from a camera), and registering the scans by computing transformations between the images, as discussed herein above.

In one embodiment, computing device 805 includes a dental diagnostics hub 830, which may include a user interface 832, one or more dental health analyzers 834 and/or one or more dental condition assessment tools 835. The user interface 132 may be a graphical user interface and may include icons, buttons, graphics, menus, windows and so on for controlling and navigating the dental diagnostics hub 839.

Each of the dental health analyzers may be responsible for performing an analysis associated with a different type of dental condition. For example, dental health analyzers 834 may include separate dental health analyzers 834 for tooth cracks, gum recession, tooth wear, occlusal contacts, crowding of teeth and/or other malocclusions, plaque, tooth stains, and/or caries. In one embodiment, a single dental health analyzer 834 performs each of the different type of dental health analyses associated with each of the types of dental conditions discussed herein. In some embodiments, there are multiple dental health analyzers, some of which perform dental health analysis for multiple different dental conditions. As discussed above, current intraoral scan data 835, past intraoral scan data 838, additional current dental data 845, additional past dental data 848 and/or reference data 850 may be used to perform one or more dental analysis. For example, the data regarding an at-hand patient may include X-rays, 2D intraoral images, 3D intraoral images, 2D models, and/or virtual 3D models corresponding to the patient visit during which the scanning occurs. The data regarding the at-hand patient may additionally include past X-rays, 2D intraoral images, 3D intraoral images, 2D models, and/or virtual 3D models of the patient (e.g., corresponding to past visits of the patient and/or to dental records of the patient).

Reference data 850 may include pooled patient data, which may include X-rays, 2D intraoral images, 3D intraoral images, 2D models, and/or virtual 3D models regarding a multitude of patients. Such a multitude of patients may or may not include the at-hand patient. The pooled patient data may be anonymized and/or employed in compliance with regional medical record privacy regulations (e.g., the Health Insurance Portability and Accountability Act (HIPAA)). The pooled patient data may include data corresponding to scanning of the sort discussed herein and/or other data. Reference data may additionally or alternatively include pedagogical patient data, which may include X-rays, 2D intraoral images, 3D intraoral images, 2D models, virtual 3D models, and/or medical illustrations (e.g., medical illustration drawings and/or other images) employed in educational contexts.

One or more Dental condition analyzers 834 may perform one or more types of dental condition analyses using intraoral data (e.g., current intraoral scan data 835, past intraoral scan data 838, additional current dental data 845, additional past dental data 848 and/or reference data 850), as discussed herein above. As a result, dental diagnostics hub 830 may determine multiple different dental conditions and severity levels of each of those types of identified dental conditions. In embodiments, dental health analyzers 834 additionally use information of multiple different types of identified dental conditions and/or associated severity levels to determine correlations and/or cause and effect relationships between two or more of the identified dental conditions. Multiple dental conditions may be caused by the same underlying root cause. Additionally, some dental conditions may serve as an underlying root cause for other dental conditions. Treatment of the underlying root cause dental conditions may mitigate or halt further development of other dental conditions. For example, malocclusion (e.g., tooth crowding and/or tooth spacing or gaps), tooth wear and caries may all be identified for the same tooth or set of teeth. Dental diagnostics hub 830 may analyze these identified dental conditions that have a common, overlapping or adjacent area of interest, and determine a correlation or causal link between one or more of the dental conditions. In example, dental diagnostics hub 830 may determine that the caries and tooth wear for a particular group of teeth is caused by tooth crowding for that group of teeth. By performing orthodontic treatment for that group of teeth, the malocclusion may be corrected, which may prevent or reduce further caries progression and/or tooth wear for that group of teeth. In another example, plaque, tooth staining, and gum recession may be identified for a region of a dental arch. The tooth staining and gum recession may be symptoms of excessive plaque. The dental diagnostics hub 830 may determine that the plaque is an underlying cause for the tooth staining and/or gum recession.

In embodiments, currently identified dental conditions may be used by the dental diagnostics hub 830 to predict future dental conditions that are not presently indicated. For example, a heavy occlusal contact may be assessed to predict tooth wear and/or a tooth crack in an area associated with the heavy occlusal contact. Such analysis may be performed by inputting intraoral data (e.g., current intraoral data and/or past intraoral data) and/or the dental conditions identified from the intraoral data into a trained machine learning model that has been trained to predict future dental conditions based on current dental conditions and/or current dentition (e.g., current 3D surfaces of dental arches). The machine learning model may be any of the types of machine learning models discussed elsewhere herein. The machine learning model may output a probability map indicating predicted locations of dental conditions and/or types of dental conditions. Alternatively, the machine learning model may output a prediction of one or more future dental conditions without identifying where those dental conditions are predicted to be located.

Dental condition assessment tools 835 may enable doctors to view and perform assessments of various types of dental conditions. Each type of dental condition may be associated with its own unique dental condition assessment tool or set of dental condition assessment tools.

FIGS. 9A-12 illustrate flow diagrams of methods performed by a dental diagnostics hub, in accordance with embodiments of the present disclosure. These methods may be performed by processing logic that comprises hardware (e.g., circuitry, dedicated logic, programmable logic, microcode, etc.), software (such as instructions run on a processing device), or a combination thereof. In one embodiment, processing logic corresponds to computing device 805 of FIG. 8 (e.g., to a computing device 805 executing an intraoral scan application 808 and/or a dental diagnostics hub 830).

Figure 9A:
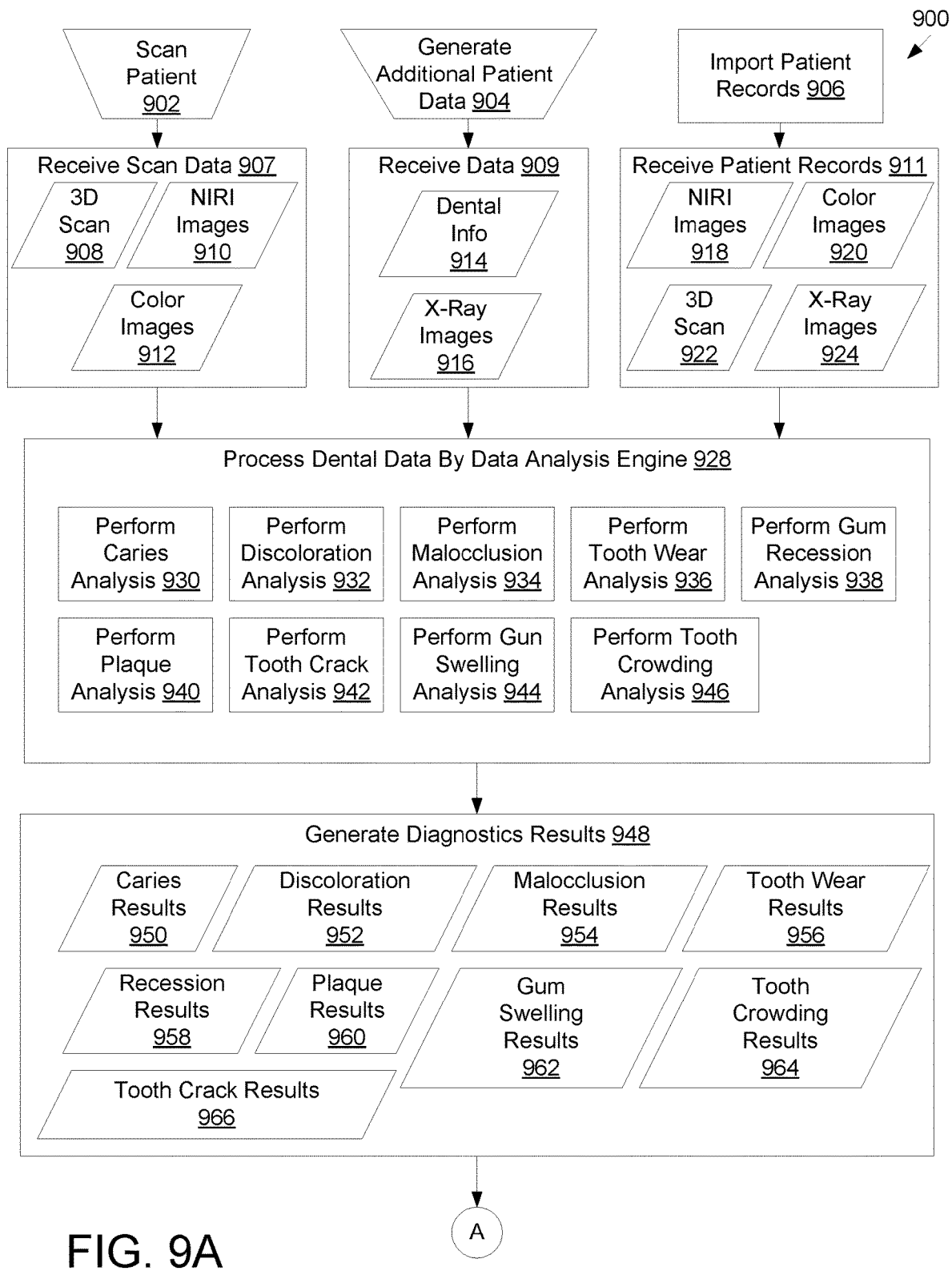
FIGS. 9A-B illustrate a flow diagram for a method of analyzing a patient's teeth and gums, in accordance with embodiments of the present disclosure.
Figure 9B:
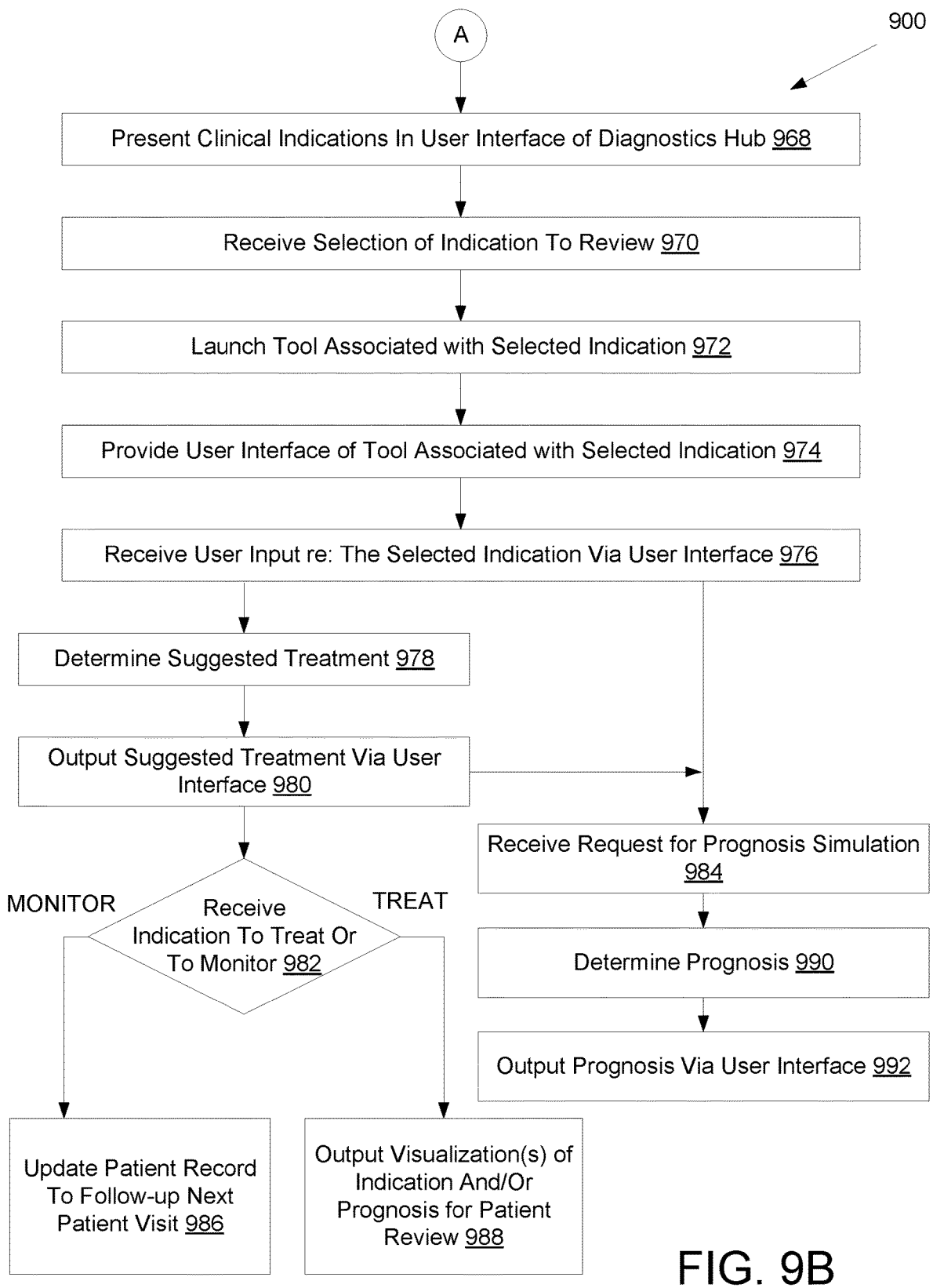

FIGS. 9A-B illustrate a flow diagram for a method 900 of analyzing a patient's teeth and gums, in accordance with embodiments of the present disclosure. At block 902, a doctor or dental practitioner scans a patient's intraoral cavity. At block 907, processing logic receives the scan data from the scan performed at block 902. The scan data may include 3D scan data (e.g., color or monochrome 3D scan data 908, which may be received in the form of point clouds, height maps, images, or other data types) and/or one or more 3D models of the patient's dental arches generated based on the scan data. The scan data may further include NIRI images 910 and/or color images 912. The 3D scan data 908, NIRI images 910 and/or color images 912 may all be generated by an intraoral scanner. At block 904, a doctor or dental practitioner may generate additional patient data. At bock 909, processing logic receives the additional patient data. The additional patient data may include x-ray images 916 (e.g., bitewing x-ray images and/or panoramic x-ray images) and/or dental information 914 (e.g., such as observations of the dental practitioner, biopsy results, CBCT scan data, ultrasound data, etc.). At block 906, processing logic may import patient records for the patient being scanned. At block 911, processing logic may receive the imported patient records. The imported patient records may include historical patient data such as historical NIRI images 918, color images 920, 3D scan data or 3D models generated from such 3D scan data 922, x-ray images 924 and/or other information.

At block 928, processing logic processes the received dental data (including the data received at blocks 908, 909 and/or 911) using one or more data analysis engine (e.g., dental health analyzer(s) 834 of FIG. 8) to identify the presence of one or more types of dental conditions and/or severity levels for the one or more detected dental conditions. Processing logic may perform a caries analysis 930, a discoloration analysis 932, a malocclusion analysis 934, a tooth wear analysis 936, a gum recession analysis 938, a plaque analysis 940, a tooth crack analysis 942, a gum swelling analysis 944 and/or a tooth crowding analysis 946 (and/or tooth spacing analysis), as discussed herein above. The various analyses may include point-in-time analyses as well as time-dependent analyses that are based on data from multiple different times. For example, older scan data may be compared to recent scan data to determine whether dental conditions have improved, stayed the same, worsened, etc. Additionally, trajectories for the various dental conditions at various areas of interest where the dental conditions were identified may be determined and projected into the future and/or past. In some embodiments, the outputs of one or more dental health analyzers are used (alone or together with intraoral data) as inputs to other dental health analyzers. For example, the presence or absence of malocclusion may be used as in input into a dental health analyzer that performs the caries analysis 930 and/or the dental health analyzer that performs plaque analysis 940.

At block 948, processing logic generates diagnostics results based on an outcome of the dental condition analyses performed at block 928. Processing logic may generate caries results 950, discoloration results 952, malocclusion results 954, tooth wear results 956, gum recession results 958, plaque results 960, gum swelling results 962, tooth crowding and/or spacing results 964 and/or tooth crack results 966. The diagnostics results may include detected AOIs associated with each of the types of dental conditions, and severity levels of the dental conditions for the AOIs. The diagnostics results may include qualitative measurements, such as size of an AOI, an amount of recession for a gum region, an amount of wear for a tooth region, and amount of change (e.g., for a caries, tooth wear, gum swelling, gum recession, tooth discoloration, etc.), a rate of change (e.g., for a caries, tooth wear, gum swelling, gum recession, tooth discoloration, etc.), and so on. The diagnostics results may further include qualitative results, such as indications as to whether a dental condition at an AOI has improved, has stayed the same, or has worsened, indications as to the rapidity with which the dental condition has improved or worsened, an acceleration in the improvement or worsening of the dental condition, and so on. An expected rate of change may have been determined (e.g., automatically or with doctor input), and the measured rate of change for a dental condition at an AOI may be compared to the expected rate of change. Differences between the expected rate of change and the measured rate of change may be recorded and included in the diagnostics results. Each of the diagnostics results may be automatically assigned a code on dental procedures and nomenclature (CDT) code or other procedural code for health and adjunctive services provided in dentistry. Each of the diagnostics results may automatically be assigned an appropriate insurance code and related financial information.

In embodiments, image documentation of one or more identified procedures may be exported from scan data (e.g., intraoral images) and associated with specific treatment codes (e.g., CDT codes) for justification of a procedure performed or to be performed, such as for insurance coverage purposes. In an example, images of gingival inflammation and/or calculus (supragingival or subgingival if detectable) can go with (or be user configured to be attached to) periodontal procedure codes. In another example, images of caries can go with or be attached to restorative codes, images of fractures or abfractions can go with or be attached to occlusion and prosthodontic codes, images of crowding/spacing can go with or be attached to orthodontic codes, and so on. This may satisfy the requirements of some insurance companies, which may require documentation prior to authorizing certain procedures.

At block 968, processing logic presents clinical indications of the dental condition analysis results in a user interface of a dental diagnostics hub, such as shown in FIG. 1C. The clinical indications may additionally be automatically added to a patient chart. For example, a patient chart may automatically be updated to identify each identified dental condition, a tooth and/or gum region affected by the dental condition, a severity level of the dental condition, and/or other information about an AOI at which the dental condition was identified. The doctor may add notes about the dental conditions as well, which may also be added to the patient chart.

The information presented in the user interface may include qualitative results and/or quantitative results of the various analyses. In embodiments, a dental diagnostics summary is shown that includes high level results, but that does not include low level details or detailed information underlying the high level results. All of the results of the analyses may be presented together in a unified view that improves clinical efficiency and provides for improved communication between the doctor and patient about the patient's oral health and how best to treat dental conditions. The summary of the dental condition results may not include or display specifics on where AOIs associated with particular dental conditions were identified and/or how many such AOIs were identified. Instead, in embodiments a minimum amount of information that is necessary to enable a doctor to formulate an initial impression about the patient's oral health may be presented. The dental conditions may be ranked based on severity level in embodiments. In embodiments, the dental conditions are grouped into multiple classifications, where one classification may indicate that no issues were found (indicating that there is no need for the doctor to review those dental conditions), one classification may indicate that potential issues were found (indicating that the doctor might want to review those dental conditions, but that such review is not urgent), and/or one classification may indicate that issues were found (indicating that the doctor is recommended to immediately review those dental conditions).

The information presented in the user interface may include information identifying one or more new dental conditions that were detected in the current or most recent patient visit but not in the prior patient visit. The information presented in the user interface may include information identifying one or more preexisting dental conditions that have improved between the prior patient visit and the current or most recent patient visit. The information presented in the user interface may include information identifying one or more preexisting dental conditions that have worsened between the prior patient visit and the current or most recent patient visit. The information presented in the user interface may include information identifying one or more preexisting dental conditions that have not changed between the prior patient visit and the current or most recent patient visit.

At block 970, processing logic receives a selection of an indication to review. For example, a doctor may select caries indications to review. At block 972, processing logic launches one or more tools associated with the selected indication. At block 974, processing logic provides a user interface for the tool or tools associated with the selected indication 974, as shown with examples in FIGS. 2-6. Via the user interface, the doctor may review detailed information about the type of dental condition that was selected.

At block 976, processing logic may receive user input (e.g., from the doctor) regarding a selected indication via the user interface. The user input may include a user input defining one or more case specific areas of interest and/or issues (e.g., dental conditions) of interest for follow-up in future scans. In a future patient visit, the dentist may generate new intraoral data for the patient, and that new intraoral data may be used along with the definition of the AOIs and/or issues of interest when performing future analysis of the patient's dental health. The user input may additionally or alternatively include a user input defining customization for AOIs and/or issues (e.g., dental conditions) of interest for all patients. For example, the doctor may define criteria (e.g., thresholds) for detecting dental conditions and/or for assessing the severity of dental conditions. The doctor may additionally or alternatively override analysis results, such as by manually updating an AOI that was indicated as being an issue for a particular class of dental condition so that it is not labeled as an issue. The dental diagnostics hub may be customized for and/or by a doctor to enable that doctor to develop their own workflows to help walk a patient through their oral health, detected dental conditions, and options for addressing the dental conditions.

At block 978, processing logic determines a suggested treatment. Each of the types of dental conditions may be associated with one or more standard treatments that are performed in dentistry and/or orthodontics to treat that type of dental condition. Based on the locations of identified AOIs, the dental conditions for the identified AOIs, the number of AOIs having dental conditions and/or the severity levels of the dental conditions, a treatment plan may be suggested. A doctor may review the treatment plan and/or adjust the treatment plan based on their practice and/or preferences. In some embodiments, the doctor may customize the dental diagnostics hub to give preference to some types of treatment options over other types of treatment options based on the doctor's preferences. Treatments may be determined for each of the identified dental conditions that are determined to have clinical significance.

At block 980, processing logic may output the suggested treatment or treatments via the user interface. In embodiments, at block 984 processing logic may receive a request for a prognosis simulation. At block 990, processing logic simulates a prognosis of the dental condition with and/or without treatment. The prognosis simulation may be based on the determined AOIs and a selected dental condition. If a treatment was selected and/or suggested at block 980, then the suggested and/or selected treatment option may be used in determining the prognosis. In embodiments, a first prognosis without treatment may be generated to show a likely course of the dental condition without treatment and a second prognosis with treatment may be generated to show a likely course of the dental condition with treatment. At block 992, the generated prognosis (or multiple prognoses) are output via the user interface. The prognosis or prognoses may be shown to a patient and/or may be sent to the patient for consideration (e.g., a link to the prognosis may be sent to the computing device of the patient).

The prognosis may include automatically generated patient communication data (also referred to as educational information) that facilitates the doctor communicating with the patient about the prognosis and possible treatments. Patient communication data may be generated for each of the types of detected dental conditions, and may be presented to the patient together via a unified presentation or separately as discrete presentations for one or more types of dental conditions. The patient communication data may include textual and/or graphical information explaining and highlighting the findings and prognoses in an easy way to understand for non-clinicians. The patient communication data may show prognoses of the patient using the patient's own dentition, projected into the future with and/or without treatment. The patient communication data may include data for one or a number of selected AOIs and/or dental conditions, or may include data for each of the AOIs and/or dental conditions or for each of the AOIs and/or dental conditions that exceed a particular severity level threshold or thresholds. In embodiments, the patient wears an augmented reality (AR) or virtual reality (VR) display, and the findings and/or prognosis are shown via augmented reality and/or virtual reality.

In an example, the patient communication data may include some or all of the dental conditions that were identified that the doctor agreed should be addressed and/or monitored. The patient communication data may further include a comparison to dental conditions and/or AOIs of the patient at prior visits, and indications of how the AOIs and/or dental conditions have changed between visits. The patient communication data may include indications as to whether an AOI and/or dental condition was discussed previously, and a decision that was made about the AOI and/or dental condition. For example, the patent communication data may indicate that the patient already has been informed of a problem and that the doctor and/or patient are keeping an eye on the problem but are not planning on treating the problem at the present time.

Educational information may be presented, which may or may not be tailored based on the patient's dentition (e.g., using 3D models of the patient's dental arches). The educational information may show progression of the patient through different severity levels of a dental condition, using that patient's own dentition. In embodiments, the dental condition analysis tools may be used to segment the patient's dental arches into teeth and gingiva, to identify dental conditions in the teeth and in the gingiva, and to predict and provide animations for progression of the various dental conditions for the patient's dental arches. Educational information may also show how the progression of dental conditions may be stopped or reversed with treatment options and/or with changes in patient behavior (e.g., brushing twice daily, flossing, wearing a night guard, etc.). Such educational information may be shown for each of the types of dental conditions discussed herein.

The information about dental conditions and/or AOIs to monitor, and the information about dental conditions and/or AOIs to treat, may be used to generate a customized report for the patient in an automated manner, with little or no doctor input. The patient communication data may further include sequencing information identifying first treatments to be performed and/or dental conditions to be addressed, subsequent treatments to be performed and/or dental conditions to be addressed, and so on. The patient communication data may indicate which treatments are optional and which treatments are necessary for the patient's dental health, and may further indicate urgency associated with each of dental conditions and associated treatments. For example, dental conditions that are emergencies may be identified, those dental conditions that should be addressed in the near future (e.g., next few months) may be identified, and those dental conditions that are not urgent but that should be addressed eventually may be identified. This enables the doctor and patient to prioritize treatment options. The patient communication data may further include information on the percentage of doctors that treat specific dental conditions, the types of treatments for those dental conditions that are performed and the rates at which those treatments are performed, and so on.

At block 982, processing logic receives an indication of one or more AOIs and/or dental conditions to monitor and/or to treat. For indications to treat an AOI and/or dental condition, the method proceeds to block 992. For indications to monitor an AOI and/or dental condition, the method proceeds to block 986.

At block 986, processing logic updates a patient record to follow-up regarding the AOIs and/or dental conditions that were identified for monitoring. At a next patient visit, processing logic will flag those AOIs and/or dental conditions that were marked for follow-up.

At block 992, processing logic may output visualizations of the indications and/or prognosis for patient review, as discussed above. The presented information may include information regarding insurance information (e.g., whether insurance covers a treatment) and/or cost. For example, the presented information may include a cost breakdown of the costs for each of the treatments to be performed to treat the one or more dental conditions. The patient may accept or decline one or more treatment options. Responsive to acceptance of a treatment option (or multiple treatment options), processing logic may automatically populate insurance paperwork with information about the dental condition(s) and/or treatment(s), and may automatically deliver the filled out insurance paperwork to an insurance company (e.g., via a discretionary portfolio management solution (DPMS) system) and/or obtain pre-authorizations from the insurance company (e.g., via a response received from the insurance company) prior to commencement of one or more treatments.

Figure 10:
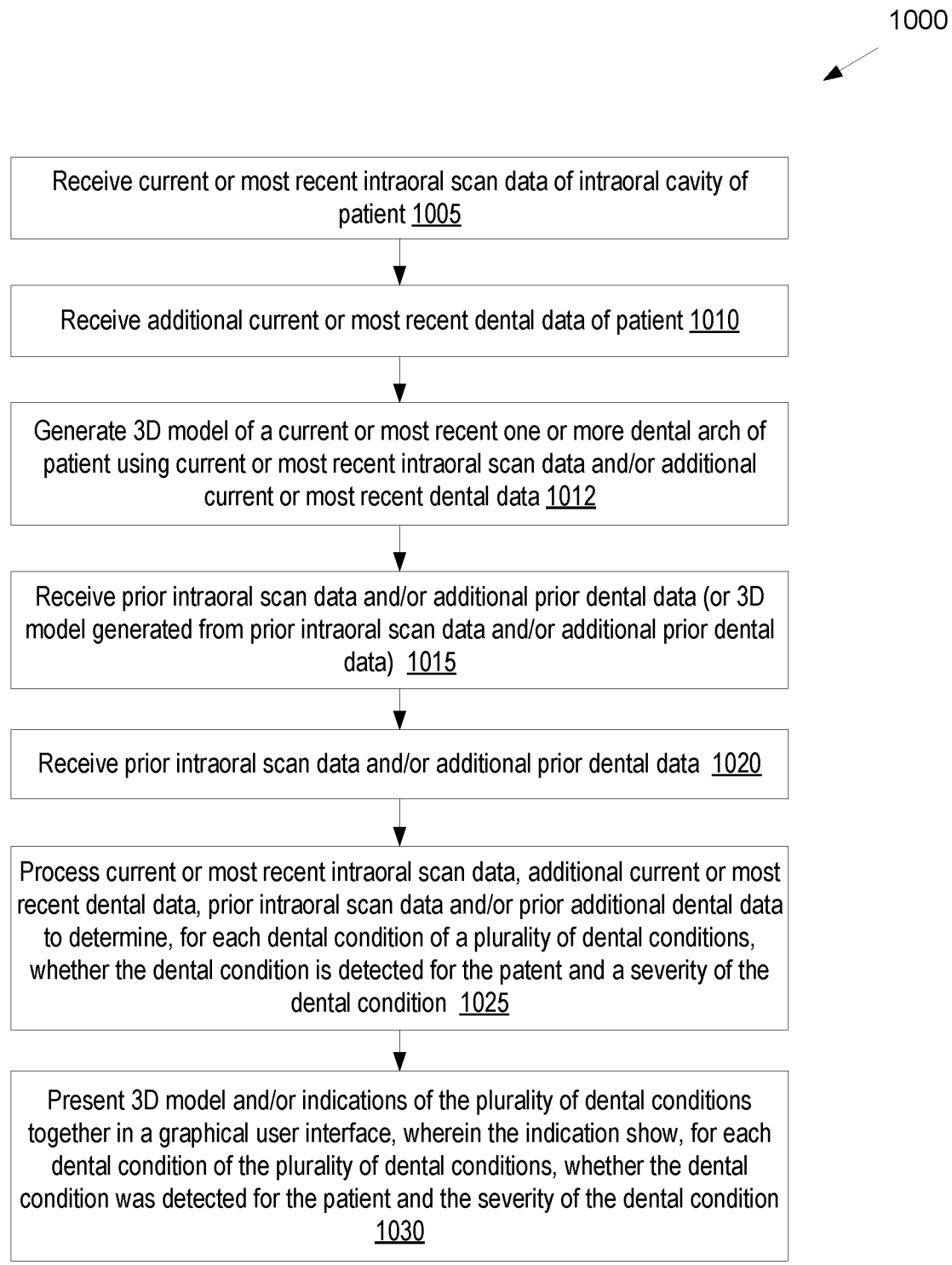
FIG. 10 illustrates a flow diagram for a method of analyzing a patient's dentition, in accordance with embodiments of the present disclosure.

FIG. 10 illustrates a flow diagram for a method 1000 of analyzing a patient's dentition, in accordance with embodiments of the present disclosure. At block 1005 of FIG. 10, processing logic receives current or most recent intraoral scan data of a patient's intraoral cavity. At block 1010, processing logic may receive additional current or most recent dental data of the patient, such as color images, NIRI images, x-ray images, and so on. At block 1012, processing logic may generate a 3D model of a current or more recent version of one or more dental arch of the patient using the current or most recent scan data and/or additional current or most recent dental data. Alternatively, the 3D model may already have been generated, and the current or most recent scan data received at block 1005 may include the 3D model of the dental arch(es).

At block 1015, processing logic At receives prior intraoral scan data of a patient's intraoral cavity. At block 1020, processing logic may receive additional prior dental data of the patient, such as color images, NIRI images, x-ray images, and so on. At block 1025, processing logic may generate a 3D model of a prior version of one or more dental arch of the patient using the prior scan data and/or additional prior dental data. Alternatively, the 3D model may already have been generated, and the prior scan data received at block 1015 may include the prior 3D model of the dental arch(es).

At block 1025, processing logic processes the current or most recent scan data, additional current or most recent dental data, current or most recent 3D model(s), prior intraoral scan data, prior dental data, and/or prior 3D model(s) to determine, for each dental condition of a plurality of dental conditions, whether the dental condition is detected for the patient and a severity of the dental condition for the patient. The operations of block 1025 may be performed by inputting data associated with the current or most recent scan data, additional current or most recent dental data, current or most recent 3D model(s), prior intraoral scan data, prior dental data, and/or prior 3D model(s) into one or more trained machine learning models. The data input into the trained machine learning model(s) may include images (which may be cropped), 3D surface data and/or projections of 3D models onto 2D planes in embodiments. The one or more trained machine learning models may be trained to receive the input data and to output classifications of AOIs and associated dental conditions for those AOIs. In one embodiment, the output of the one or more trained machine learning models includes one or more probability maps or classification maps that indicate, for each point or pixel from the input data, a probability of that point or pixel belonging to one or more dental condition classifications and forming part of an AOI associated with a dental condition. The trained machine learning models may additionally be trained to output severity levels of the dental conditions associated with the AOIs. Alternatively, processing logic may perform additional processing using the output of the one or more trained machine learning models (and optionally the data that was input into the trained machine learning models) to determine severity levels of the dental conditions at the AOIs.

At block 1030, processing logic presents indications of the plurality of dental conditions together in a graphical user interface or other display (e.g., in a dental diagnostics summary, such as shown in FIG. 1C). The indications may show, for each dental condition, whether the dental condition was detected for the patient and the severity of the dental condition. For example, for each dental condition there may be an indication showing that there is an issue detected for that dental condition, that there is a potential issue detected for that dental condition, or that there is an issue detected for that dental condition. A 3D model of the current or most recent one or more dental arch may also be presented together with the indications of dental conditions.

Figure 11:
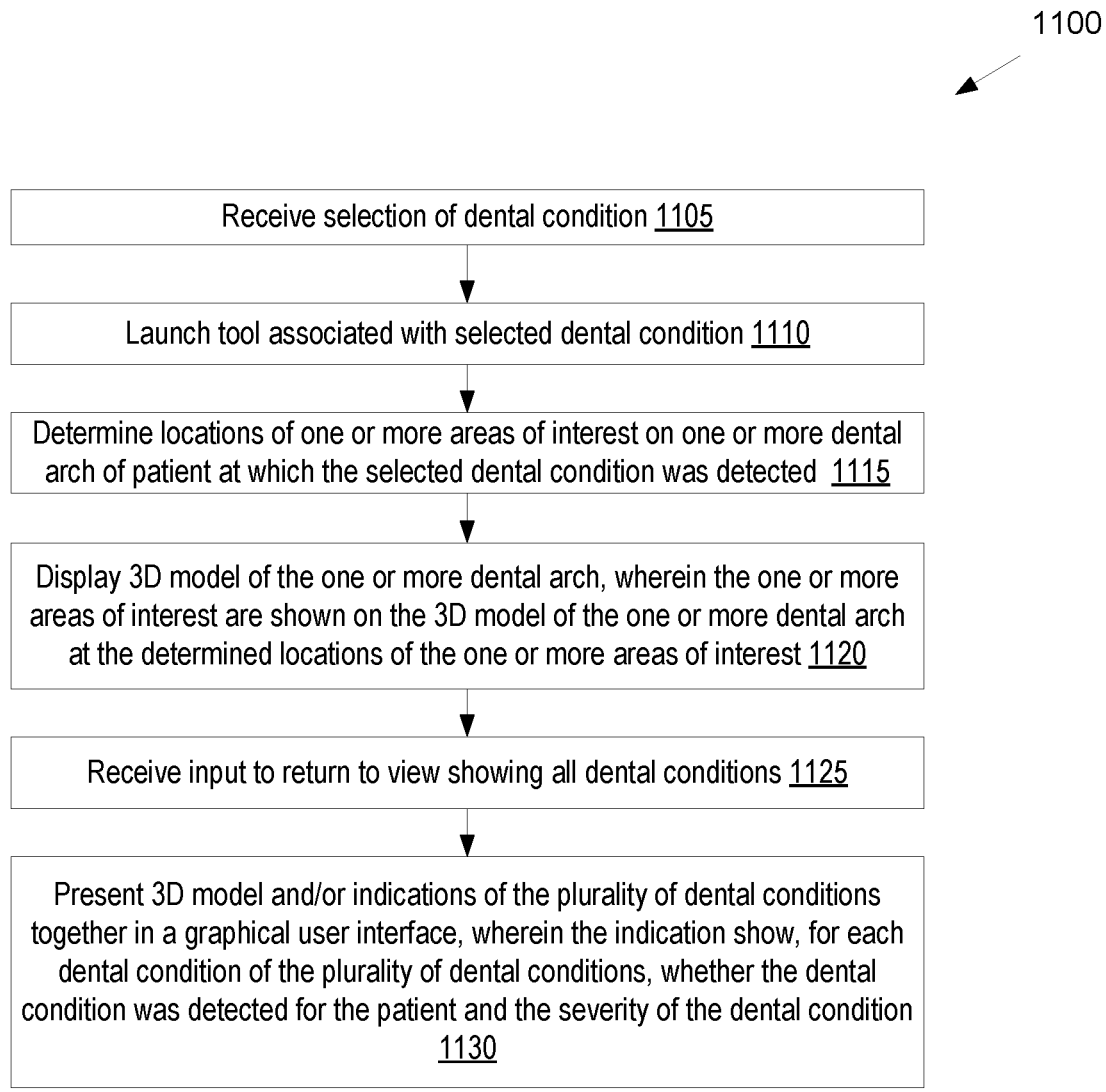
FIG. 11 illustrates a flow diagram for a method of navigating a dental diagnostics hub, in accordance with embodiments of the present disclosure.

FIG. 11 illustrates a flow diagram for a method 1100 of navigating a dental diagnostics hub, in accordance with embodiments of the present disclosure. Method 1100 may be performed after method 1000 has been performed in embodiments. At block 1105 of method 1100, processing logic receives a selection of a dental condition. The selection may be received responsive to presenting the indications of the dental conditions together at block 1030 of method 1000. At block 1110, processing logic launches one or more tools associated with the selected dental condition. The tools may include, for example, caries analysis and review tools, orthodontic treatment tools, tooth stain assessment tools, occlusal contact assessment tools, and so on.

At block 1115, processing logic determines locations of one or more AOIs on the one or more dental arch of the patient at which the selected dental condition was detected. At block 1120, processing logic displays the 3D models of the one or more dental arches along with the AOIs shown at the determined locations on the 3D models. The doctor may review the AOIs to make their own assessment as to the existence and/or severity of the dental condition. This may include zooming in or out on the AOIs, panning, rotating the view of the AOIs, looking at additional data regarding the AOIs such as NIRI imaging data, ultraviolet imaging data, color data, x-ray data, and so on.

At block 1125, once the doctor is finished assessing the AOIs associated with the selected dental condition, processing logic may receive an input to return to the view showing all of the dental conditions (e.g., to a dental diagnostics summary). At block 1130, processing logic presents the 3D model and/or indications of the dental conditions together in the GUI. For example, processing logic may return to a view of the dental diagnostics summary.

Figure 12:
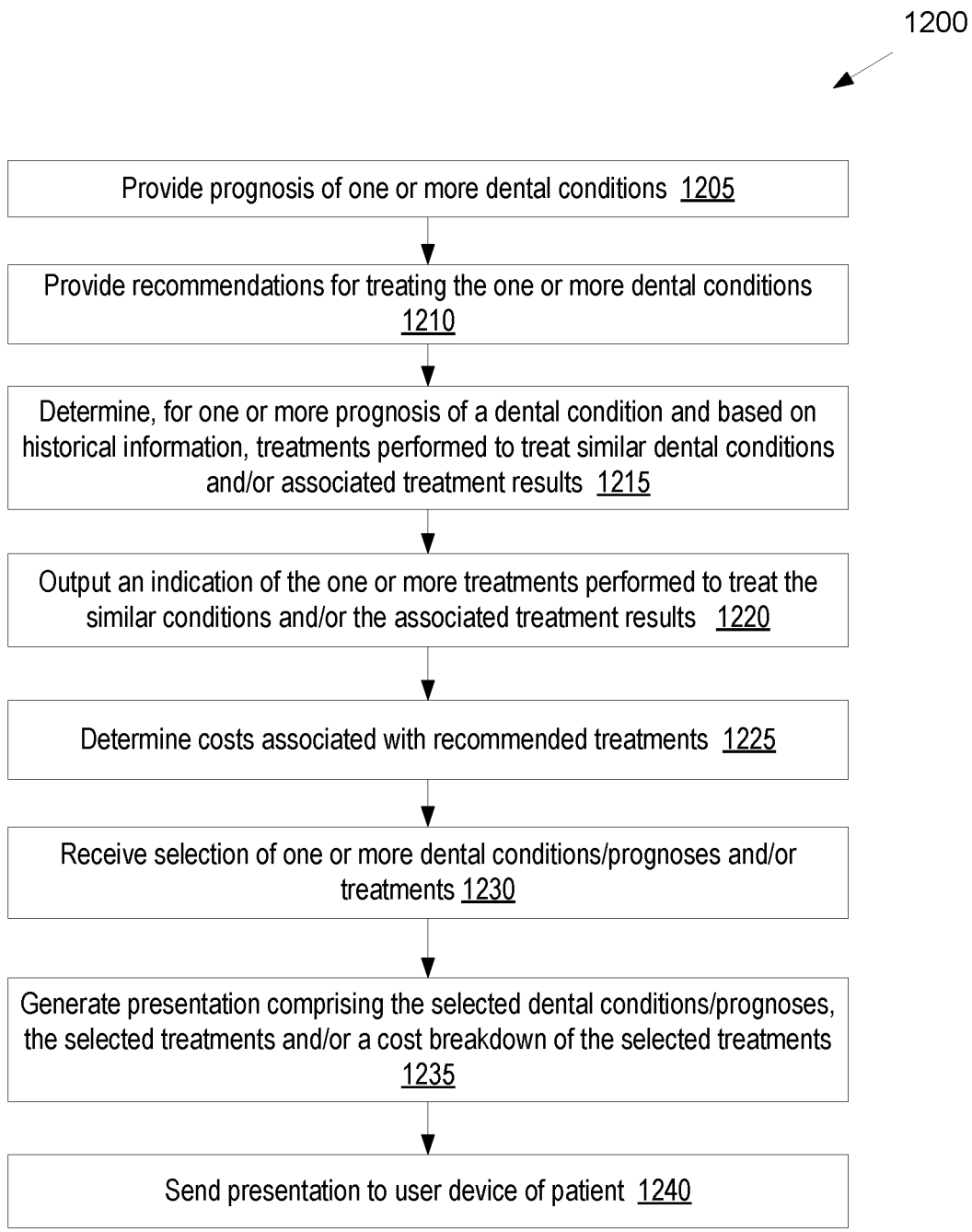
FIG. 12 illustrates a flow diagram for a method of generating a presentation of identified dental and/or gum conditions of a patient, in accordance with embodiments of the present disclosure.

FIG. 12 illustrates a flow diagram for a method 1200 of generating a presentation of identified dental and/or gum conditions of a patient, in accordance with embodiments of the present disclosure. Method 1200 may be performed after method 1000 and/or method 1100 in embodiments. At block 1205 of method 1200, processing logic provides a prognosis of one or more detected dental conditions at one or more AOIs on the patient's dental arch(es). As part of providing the prognosis, processing logic may determine the prognosis, such as by using machine learning and/or by projecting a detected progression and/or rate of change of each of the dental conditions into the future. At block 1210, processing logic provides one or more recommendations for treating the one or more dental conditions. The recommendations may be based on data gathered from many doctors over many patients, and may indicate for dental conditions similar to those detected for the current patient, specific treatment(s) that was performed. For example, at block 1215 processing logic may determine, for the one or more prognosis and the dental condition (and optionally based on historical information about the patient at hand), treatments that were performed to treat similar dental conditions as well as associated treatment results. Processing logic may determine, based on historical information, at least one of one or more treatments performed to treat similar dental conditions or associated treatment results. At block 1220, processing logic may output an indication of the one or more treatments performed to treat the similar conditions and/or the associated treatment results.

At block 1225, processing logic may determine the costs associated with the recommended treatments. At block 1230, processing logic receives a selection of one or more dental conditions and/or treatments. At block 1235, processing logic automatically generates a presentation comprising the selected dental conditions, the associated prognoses for the selected dental conditions, the selected treatments and/or a cost breakdown of the selected treatments. At block 1240, the generated presentation may be shown to the patient and/or may be sent to a user device of the patient (e.g., to a mobile computing device or a traditionally stationary computing device of the patient). This may include sending a link to access the presentation to the user device of the patient.

Figure 13:
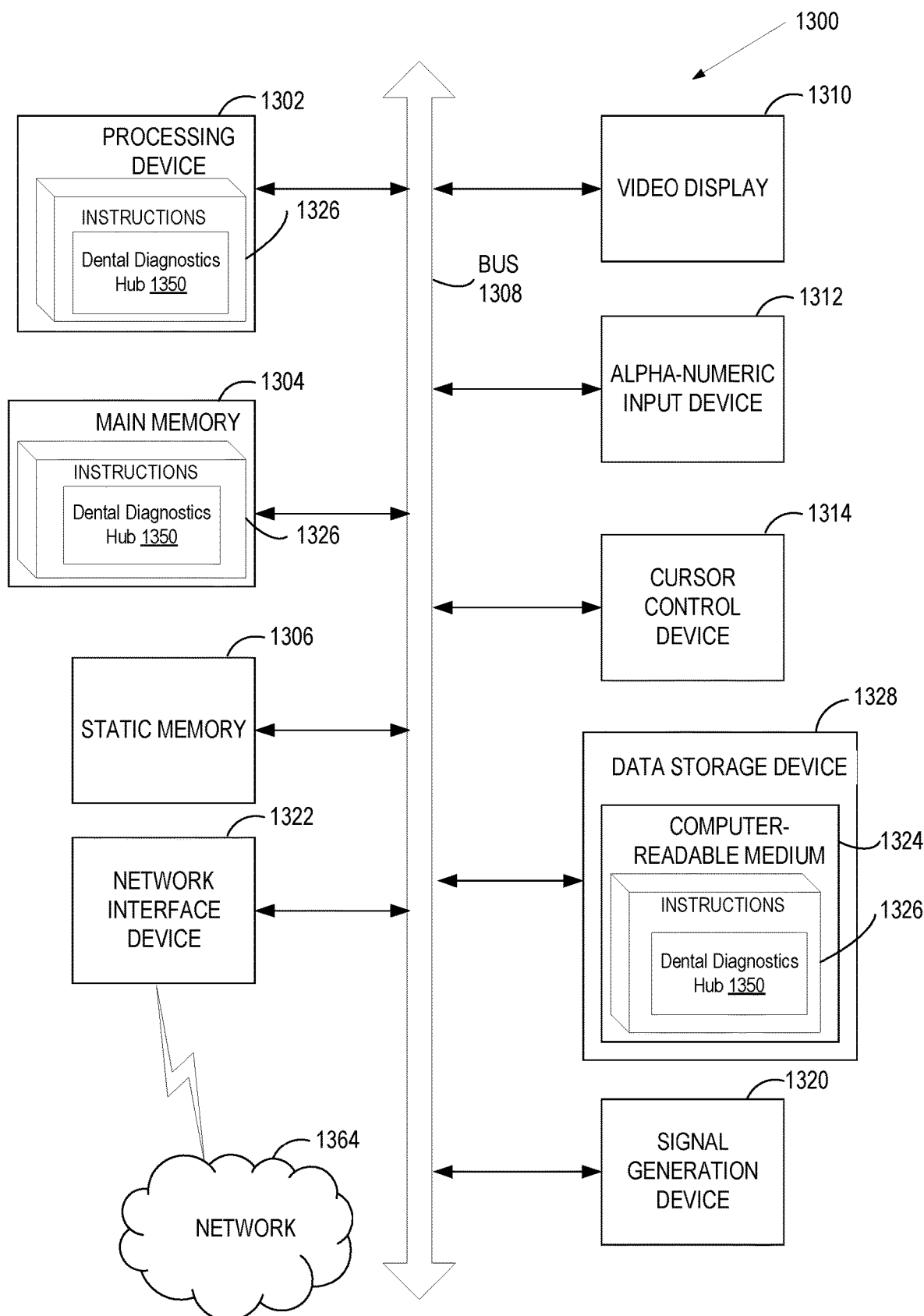
FIG. 13 illustrates a block diagram of an example computing device, in accordance with embodiments of the present disclosure.

FIG. 13 illustrates a diagrammatic representation of a machine in the example form of a computing device 1300 within which a set of instructions, for causing the machine to perform any one or more of the methodologies discussed herein, may be executed. In alternative embodiments, the machine may be connected (e.g., networked) to other machines in a Local Area Network (LAN), an intranet, an extranet, or the Internet. The machine may operate in the capacity of a server or a client machine in a client-server network environment, or as a peer machine in a peer-to-peer (or distributed) network environment. The machine may be a personal computer (PC), a tablet computer, a set-top box (STB), a Personal Digital Assistant (PDA), a cellular telephone, a web appliance, a server, a network router, switch or bridge, or any machine capable of executing a set of instructions (sequential or otherwise) that specify actions to be taken by that machine. Further, while only a single machine is illustrated, the term "machine" shall also be taken to include any collection of machines (e.g., computers) that individually or jointly execute a set (or multiple sets) of instructions to perform any one or more of the methodologies discussed herein. In one embodiment, the computing device 1300 corresponds to computing device 805 of FIG. 8.

The example computing device 1300 includes a processing device 1302, a main memory 1304 (e.g., read-only memory (ROM), flash memory, dynamic random access memory (DRAM) such as synchronous DRAM (SDRAM), etc.), a static memory 1306 (e.g., flash memory, static random access memory (SRAM), etc.), and a secondary memory (e.g., a data storage device 1328), which communicate with each other via a bus 1308.

Processing device 1302 represents one or more general-purpose processors such as a microprocessor, central processing unit, or the like. More particularly, the processing device 1302 may be a complex instruction set computing (CISC) microprocessor, reduced instruction set computing (RISC) microprocessor, very long instruction word (VLIW) microprocessor, processor implementing other instruction sets, or processors implementing a combination of instruction sets. Processing device 1302 may also be one or more special-purpose processing devices such as an application specific integrated circuit (ASIC), a field programmable gate array (FPGA), a digital signal processor (DSP), network processor, or the like. Processing device 1302 is configured to execute the processing logic (instructions 1326) for performing operations and steps discussed herein.

The computing device 1300 may further include a network interface device 1322 for communicating with a network 1364. The computing device 1300 also may include a video display unit 1310 (e.g., a liquid crystal display (LCD) or a cathode ray tube (CRT)), an alphanumeric input device 1312 (e.g., a keyboard), a cursor control device 1314 (e.g., a mouse), and a signal generation device 1320 (e.g., a speaker).

The data storage device 1328 may include a machine-readable storage medium (or more specifically a non-transitory computer-readable storage medium) 1324 on which is stored one or more sets of instructions 1326 embodying any one or more of the methodologies or functions described herein. A non-transitory storage medium refers to a storage medium other than a carrier wave. The instructions 1326 may also reside, completely or at least partially, within the main memory 1304 and/or within the processing device 1302 during execution thereof by the computer device 1300, the main memory 1304 and the processing device 1302 also constituting computer-readable storage media.

The computer-readable storage medium 1324 may also be used to store a dental diagnostics hub 1350, which may correspond to the similarly named component of FIG. 8. The computer readable storage medium 1324 may also store a software library containing methods for a dental diagnostics hub 1350. While the computer-readable storage medium 1324 is shown in an example embodiment to be a single medium, the term "computer-readable storage medium" should be taken to include a single medium or multiple media (e.g., a centralized or distributed database, and/or associated caches and servers) that store the one or more sets of instructions. The term "computer-readable storage medium" shall also be taken to include any non-transitory medium (e.g., a medium other than a carrier wave) that is capable of storing or encoding a set of instructions for execution by the machine and that cause the machine to perform any one or more of the methodologies of the present disclosure. The term "computer-readable storage medium" shall accordingly be taken to include, but not be limited to, solid-state memories, and optical and magnetic media.

It is to be understood that the above description is intended to be illustrative, and not restrictive. Many other embodiments will be apparent upon reading and understanding the above description. Although embodiments of the present disclosure have been described with reference to specific example embodiments, it will be recognized that the disclosure is not limited to the embodiments described, but can be practiced with modification and alteration within the spirit and scope of the appended claims. Accordingly, the specification and drawings are to be regarded in an illustrative sense rather than a restrictive sense. The scope of the disclosure should, therefore, be determined with reference to the appended claims, along with the full scope of equivalents to which such claims are entitled.

What is claimed is:

1. A non-transitory computer readable medium comprising instructions that, when executed by a processing device, cause the processing device to perform operations comprising:
    receiving intraoral scan data of an oral cavity of a patient;
    performing a plurality of automated analyses of the intraoral scan data to determine, for each dental condition of a plurality of dental conditions, whether the dental condition is detected for the patient and a severity level of the dental condition;
    generating a dental diagnostics summary based on results of the plurality of automated analyses, the dental diagnostics summary comprising indications of the plurality of dental conditions, wherein the indications show, for each dental condition of the plurality of dental conditions, whether the dental condition was detected for the patient and the severity level of the dental condition;
    presenting the dental diagnostics summary in a graphical user interface (GUI);
    receiving a selection of a dental condition that was detected for the patient from the plurality of dental conditions in the dental diagnostics summary;
    launching a tool associated with the selected dental condition; and
    providing more detailed information about the selected dental condition, wherein providing the more detailed information comprises:
        determining locations of one or more areas of interest on a dental arch of the patient at which the selected dental condition was detected; and
        displaying a three-dimensional (3D) model of the dental arch in the GUI, wherein the one or more areas of interest are shown on the 3D model of the dental arch at the determined locations of the one or more areas of interest.

2. The non-transitory computer readable medium of claim 1, wherein performing the plurality of automated analyses of the intraoral scan data comprises processing the intraoral scan data using a plurality of trained machine learning models, wherein the plurality of trained machine learning models comprises a first trained machine learning model trained to identify a first subset of the plurality of dental conditions and a second trained machine learning model trained to identify a second subset of the plurality if dental conditions.

3. The non-transitory computer readable medium of claim 2, wherein the first trained machine learning model is trained to output locations of areas of interest in the oral cavity of the patient at which the first subset of the plurality of dental conditions were detected.

4. The non-transitory computer readable medium of claim 1, wherein the plurality of dental conditions comprises one or more prosthodontic dental conditions, one or more temporomandibular joint dental conditions, one or more orthodontic dental conditions, one or more periodontal dental conditions, and one or more endodontic dental conditions.

5. The non-transitory computer readable medium of claim 1, the operations further comprising:
    generating the 3D model of the dental arch of the patient based on the intraoral scan data.

6. The non-transitory computer readable medium of claim 1, wherein the intraoral scan data comprises three-dimensional scan data, two-dimensional near infrared scan data and two-dimensional color scan data, and wherein at least two of the three-dimensional scan data, the two-dimensional near infrared scan data or the two-dimensional color scan data are processed together to determine one or more of the plurality of dental conditions.

7. The non-transitory computer readable medium of claim 1, wherein the intraoral scan data was generated by an intraoral scanner, the operations further comprising:
    receiving at least one of a plurality of x-ray images of the oral cavity of the patient, a panoramic x-ray of the oral cavity of the patient, a cone-beam computed tomography (CBCT) scan of the oral cavity of the patient, or one or more color two-dimensional images of the oral cavity of the patient, wherein the at least one of the plurality of x-ray images, the panoramic x-ray, the CBCT scan or the one or more color two-dimensional images were generated by one or more device other than an intraoral scanner;
    wherein processing the intraoral scan data comprises processing the intraoral scan data together with at least one of the plurality of x-ray images, the panoramic x-ray, the CBCT scan or the one or more color two-dimensional images.

8. The non-transitory computer readable medium of claim 1, wherein the intraoral scan data comprises a first time stamp associated with a current or most recent patient visit, the operations further comprising:
    receiving second intraoral scan data of the oral cavity of the patient, wherein the second intraoral scan data was generated during a prior patient visit and comprises a second time stamp that predates the first time stamp;

comparing the second intraoral scan data to the intraoral scan data to determine differences therebetween; and determining, for one or more dental conditions of the plurality of dental conditions, rates of change for the one or more dental conditions;

wherein the severity levels for the one or more dental conditions are determined based on current states of the one or more dental conditions and the rates of change for the one or more dental conditions.

9. The non-transitory computer readable medium of claim 8, wherein the operations further comprise performing at least one of:

identifying one or more new dental conditions that were detected in the current or most recent patient visit but not in the prior patient visit;

identifying one or more preexisting dental conditions that have improved between the prior patient visit and the current or most recent patient visit;

identifying one or more preexisting dental conditions that have worsened between the prior patient visit and the current or most recent patient visit; or identifying one or more preexisting dental conditions that have not changed between the prior patient visit and the current or most recent patient visit.

10. The non-transitory computer readable medium of claim 1, wherein for at least one dental condition of the plurality of dental conditions, the determination of whether the dental condition is detected is based on comparison of the severity level to a threshold, wherein responsive to determining that the severity level meets or exceeds the threshold, the dental condition is classified as having been detected, and wherein responsive to determining that the severity level is below the threshold, the dental condition is classified as not having been detected, the operations further comprising:

receiving an input setting a value for the threshold.

11. The non-transitory computer readable medium of claim 1, the operations further comprising:

ranking the plurality of dental conditions based at least in part on severity level.

12. The non-transitory computer readable medium of claim 1, the operations further comprising:

providing, for one or more dental conditions of the plurality of dental conditions that were detected for the patient, a prognosis of the one or more dental conditions and a recommended treatment of the one or more dental conditions based at least in part on the severity levels for the one or more dental conditions;

receiving a selection of one or more recommended treatments; and generating a presentation comprising the one or more selected recommended treatments and associated prognoses of the one or more selected recommended treatments.

13. The non-transitory computer readable medium of claim 12, the operations further comprising:

determining a cost breakdown associated with performing the one or more recommended treatments, wherein the presentation comprises the cost breakdown.

14. The non-transitory computer readable medium of claim 12, the operations further comprising:

sending the presentation to a user device of the patient.

15. The non-transitory computer readable medium of claim 1, the operations further comprising:

for the selected dental condition, performing the following comprising:

determining a prognosis of the selected dental condition;

determining, based on historical information, at least one of one or more treatments performed to treat similar dental conditions or associated treatment results; and outputting an indication of the at least one of the one or more treatments performed to treat the similar dental conditions or the associated treatment results.

16. The non-transitory computer readable medium of claim 1, wherein determining whether a dental condition is detected for the patient and the severity level of the dental condition comprises assigning one of a plurality of dental condition classifiers for the dental condition, wherein the plurality of dental condition classifiers comprise a first dental condition classifier indicating that the dental condition is present, a second dental condition classifier indicating that the dental condition may be present, and a third dental condition classifier indicating that the dental condition is not present.

17. A system for assessing dental conditions of a patient, comprising:

an intraoral scanner configured to generate intraoral scan data of an oral cavity of the patient; and a computing device, wherein the computing device is configured to:

receive the intraoral scan data;

perform a plurality of automated analyses of the intraoral scan data to determine, for each dental condition of a plurality of dental conditions, whether the dental condition is detected for the patient and a severity level of the dental condition;

generate a dental diagnostics summary based on results of the plurality of automated analyses, the dental diagnostics summary comprising indications of the plurality of dental conditions, wherein the indications show, for each dental condition of the plurality of dental conditions, whether the dental condition was detected for the patient and the severity level of the dental condition;

present the dental diagnostics summary in a graphical user interface (GUI);

receive a selection of a dental condition that was detected for the patient from the plurality of dental conditions in the dental diagnostics summary;

launch a tool associated with the selected dental condition; and provide more detailed information about the selected dental condition, wherein providing the more detailed information comprises:

determining locations of one or more areas of interest on a dental arch of the patient at which the selected dental condition was detected; and displaying a three-dimensional (3D) model of the dental arch in the GUI, wherein the one or more areas of interest are shown on the 3D model of the dental arch at the determined locations of the one or more areas of interest.

18. The system of claim 17, wherein performing the plurality of automated analyses of the intraoral scan data comprises processing the intraoral scan data using a plurality of trained machine learning models, wherein the plurality of trained machine learning models comprise a first trained machine learning model trained to identify a first subset of the plurality of dental conditions and a second trained machine learning model trained to identify a second subset of the plurality of dental conditions.

19. The system of claim 18, wherein the first trained machine learning model is trained to output locations of areas of interest in the oral cavity of the patient at which the first subset of the plurality of dental conditions were detected.

20. The system of claim 17, wherein the plurality of dental conditions comprises one or more prosthodontic dental conditions, one or more temporomandibular dental conditions, one or more orthodontic dental conditions, one or more periodontal dental conditions, and one or more endodontic dental conditions.

21. The system of claim 17, wherein the computing device is further to:
generate the 3D model of the dental arch based on the intraoral scan data.

22. The system of claim 17, wherein the intraoral scan data comprises three-dimensional scan data, two-dimensional near infrared scan data and two-dimensional color scan data, and wherein at least two of the three-dimensional scan data, the two-dimensional near infrared scan data or the two-dimensional color scan data are processed together to determine one or more of the plurality of dental conditions.

23. The system of claim 17, wherein the intraoral scan data was generated by an intraoral scanner, and wherein the computing device is further to:
receive at least one of a plurality of x-ray images of the oral cavity of the patient, a panoramic x-ray of the oral cavity of the patient, a cone-beam computed tomography (CBCT) scan of the oral cavity of the patient, or one or more color two-dimensional images of the oral cavity of the patient, wherein the at least one of the plurality of x-ray images, the panoramic x-ray, the CBCT scan or the one or more color two-dimensional images were generated by one or more device other than an intraoral scanner;
wherein processing the intraoral scan data comprises processing the intraoral scan data together with at least one of the plurality of x-ray images, the panoramic x-ray, the CBCT scan or the one or more color two-dimensional images.

24. The system of claim 17, wherein the intraoral scan data comprises a first time stamp associated with a current or most recent patient visit, and wherein the computing device is further to:
receive second intraoral scan data of the oral cavity of the patient, wherein the second intraoral scan data was generated during a prior patient visit and comprises a second time stamp that predates the first time stamp;
compare the second intraoral scan data to the intraoral scan data to determine differences therebetween; and
determine, for one or more dental conditions of the plurality of dental conditions, rates of change for the one or more dental conditions;
wherein the severity levels for the one or more dental conditions are determined based on current states of the one or more dental conditions and the rates of change for the one or more dental conditions.

25. The system of claim 17, wherein for at least one dental condition of the plurality of dental conditions, the determination of whether the dental condition is detected is based on comparison of the severity level to a threshold, wherein responsive to determining that the severity level meets or exceeds the threshold, the dental condition is classified as having been detected, and wherein responsive to determining that the severity level is below the threshold, the dental condition is classified as not having been detected, wherein the computing device is further to:
receive an input setting a value for the threshold.

26. The system of claim 17, wherein the computing device is further to:
provide a prognosis of the selected dental condition and a recommended treatment of the selected dental condition based at least in part on a severity level for the selected dental condition;
receive a selection of one or more recommended treatments; and
generate a presentation comprising the one or more selected recommended treatments and associated prognoses of the one or more selected recommended treatments.

27. A method comprising:
receiving intraoral scan data of an oral cavity of a patient;
performing a plurality of automated analyses of the intraoral scan data to determine, for each dental condition of a plurality of dental conditions, whether the dental condition is detected for the patient and a severity level of the dental condition;
generating a dental diagnostics summary based on results of the plurality of automated analyses, the dental diagnostics summary comprising indications of the plurality of dental conditions, wherein the indications show, for each dental condition of the plurality of dental conditions, whether the dental condition was detected for the patient and the severity level of the dental condition;
presenting the dental diagnostics summary in a graphical user interface (GUI);
receiving a selection of a dental condition that was detected for the patient from the plurality of dental conditions in the dental diagnostics summary;
launching a tool associated with the selected dental condition; and
providing more detailed information about the selected dental condition, wherein providing the more detailed information comprises:
determining locations of one or more areas of interest on a dental arch of the patient at which the selected dental condition was detected; and
displaying a three-dimensional (3D) model of the dental arch in the GUI, wherein the one or more areas of interest are shown on the 3D model of the dental arch at the determined locations of the one or more areas of interest.

* * * * *